US009108183B2

(12) United States Patent
Dalai et al.

(10) Patent No.: US 9,108,183 B2
(45) Date of Patent: Aug. 18, 2015

(54) CATALYSTS FOR THE CONVERSION OF SYNTHESIS GAS TO ALCOHOLS

(75) Inventors: Ajay Kumar Dalai, Saskatoon (CA); Venkateswara Rao Surisetty, Saskatoon (CA)

(73) Assignee: University of Saskatchewan, Saskatoon (CA)

( * ) Notice: Subject to any disclaimer, the term of this patent is extended or adjusted under 35 U.S.C. 154(b) by 454 days.

(21) Appl. No.: 13/457,893

(22) Filed: Apr. 27, 2012

(65) Prior Publication Data
US 2012/0283342 A1 Nov. 8, 2012

Related U.S. Application Data

(60) Provisional application No. 61/482,669, filed on May 5, 2011.

(51) Int. Cl.
| | |
|---|---|
| *C07C 27/00* | (2006.01) |
| *B01J 21/18* | (2006.01) |
| *B01J 23/89* | (2006.01) |
| *B01J 35/00* | (2006.01) |
| *B01J 35/02* | (2006.01) |
| *B01J 35/10* | (2006.01) |
| *B01J 37/02* | (2006.01) |
| *B01J 37/20* | (2006.01) |
| *C07C 29/157* | (2006.01) |
| *C07C 29/158* | (2006.01) |
| *B82Y 30/00* | (2011.01) |

(52) U.S. Cl.
CPC ............ *B01J 21/185* (2013.01); *B01J 23/8993* (2013.01); *B01J 35/002* (2013.01); *B01J 35/0066* (2013.01); *B01J 35/023* (2013.01); *B01J 35/1014* (2013.01); *B01J 35/1038* (2013.01); *B01J 35/1061* (2013.01); *B01J 37/0205* (2013.01); *B01J 37/0207* (2013.01); *B01J 37/20* (2013.01); *B82Y 30/00* (2013.01); *C07C 29/157* (2013.01); *C07C 29/158* (2013.01)

(58) Field of Classification Search
CPC .... C07C 29/157; C07C 31/08; C07C 29/158; B01J 21/185; B01J 35/002; B01J 35/0066; B01J 35/023
USPC .......................... 518/700, 714, 715, 716, 717
See application file for complete search history.

(56) References Cited

U.S. PATENT DOCUMENTS

| | | | |
|---|---|---|---|
| 4,752,622 A | | 6/1988 | Stevens |
| 4,980,380 A | * | 12/1990 | Wong et al. .................... 518/714 |
| 2010/0331581 A1 | * | 12/2010 | Kharas et al. ................. 568/840 |

OTHER PUBLICATIONS

Surisetty, V.R., et al., "Higher Alcohols Synthesis from Syngas over K/MoS2 Catalysts Supported on Multi-Walled Carbon Nanotubes", 58th Canadian Chemical Engineering Conference, Ottawa, Ontario, Canada, Oct. 19-22, 2008.

Surisetty V.R., et al., "Higher Alcohol syntheses from Syngas over Co or Rh Promoted Alkali Modified Molybdenum Sulfide Catalysts", 2009 AiChE Annual Meeting, Nashville, Tennessee, USA, Nov. 12, 2009.
Ma, Chun-Hui, et al., "MWCNT-Supported Ni—Mo—K Catalyst for Higher Alcohol Synthesis from Syngas", Catalysis Letters, vol. 137, p. 171-179, 2010.
Matsumoto, Takeshi, et al., "Catalytic hydrogenation of carbon monoxide over silica-supported Ir—Mo—Rh catalyst", Catalysis Letters, vol. 24, p. 391-394, 1994.
Surisetty, V.R., et al., "Synthesis of Higher Alcohols from Synthesis Gas Using Various CNT Supported Catalysts", AIBN, London, Ontario, Jan. 9-11, 2011.
Surisetty, V.R., et al., "Higher Alcohols Synthesis Using Alkali Promoted Trimetallic Co—Rh—Mo Sulfide Catalysts Supported on MWCNT and Activated Carbon", 21st Canadian Symposium on Catalysis, May 9-12, 2010, Banff Alberta, Canada.
Storm, D.A., "The Production of higher alcohols from syngas using potassium promoted Co/Mo/Al2O3 and Rh/Co/Mo/ Al2O3", Topics in Catalysis 2 (1995) 91-101.
Surisetty, V.R., et al., "Synthesis of higher alcohols from syngas over alkali prmoted MoS2 catalysts supported on multi-walled carbon nanotubes", Applied Catalysis A: General 365 (2009), 243-251.
Surisetty, V.R., et al., "Effect of Rh promoter on MWCNT-supported alkali-modified MoS2 catalysts for higher alcohols synthesis from CO hydrogenation", Applied Catalysis A: General 381 (2010) 282-288.
Surisetty, V.R., et al., "Alkali-Promoted Trimetallic Co—Rh—Mo Sulfide Catalysts for Higher Alcohols Synthesis from Synthesis Gas: Comparison of MWCNT and Activated Carbon Supports", Ind. Eng. Chem. Res. 2010, 49, 6956-6963.
Surisetty, V.R., et al., Intrinsic Reaction Kinetics of Higher Alcohol Synthesis from Synthesis Gas over a Sulfided Alkali-Promoted Co—Rh—Mo Trimetallic Catalys Supported on Multiwalled Carbon Nanotubes (MWCNTs), Energy Fuels, 2010, 24, 4130-4137.
Surisetty, V.R., et al., Synthesis of higher alcohols from synthesis gas over Co-promoted alkali-modified MoS2 catalysts supported on MWCNTs, Applied Catalysis A: General 385 (2010) 153-162.
Surisetty, V.R., et al., "Structural characterization and catalytic performance of alkali (K) and metal (Co and Rh)-promoted MoS2 catalysts for higher alcohols synthesis", Applied Catalysis A: General 392 (2011) 166-172.
Surisetty, V.R., et al., "Influence of porous characteristics of the carbon support on alkali-modified trimetallic Co—Rh—Mo sulfided catalysts for higher alcohols synthesis from synthesis gas", Applied Catalysis A: General 393 (2011) 50-58.
Surisetty, V.R., et al., "Deactiviation Studies of Alkali-Promoted Trimetallic Co—Rh—Mo Sulfide Catalysts for Higher Alcohols Synthesis from Synthesis Gas", Energy Fuels, 2011, 25, 580-590.
Ma, Xiaoming, et al., "Co—Mo—K Sulfide-Based Catalyst Promoted by Multiwalled Carbon Nanotubes for Higher Alcohol Synthesis from Syngas", Chinese Journal of Catalysis: vol. 27, Issue 11, Nov. 2006, 1019-1027.

(Continued)

*Primary Examiner* — Jafar Parsa
(74) *Attorney, Agent, or Firm* — Bereskin & Parr LLP/S.E.N.C.R.L., s.r.l.; Patricia Folkins

(57) ABSTRACT

The present application includes alkali metal-promoted trimetallic catalysts for higher alcohol synthesis from synthesis gas, the catalyst comprising a catalyst of Formula (1):

$A-M^1-M^2-M^3$.

15 Claims, 51 Drawing Sheets

(56) References Cited

OTHER PUBLICATIONS

Surisetty, V.R., et al, "Higher Alcohols synthesis from Synthesis gas over Co, and/or Rh modified Alkali Promoted MoS2 Catalysts", presentation, Sep. 21, 2009.

Surisetty, V.R., et al., "XANES Characterization and Catalytic Performance of Alkali and Metal (Co and Rh)-promoted MoS2 Catalysts for Higher Alcohols Synthesis", 60th Canadian Chemical Engineering Conference (CSChE2010), Saskatoon, Canada, Oct. 24-27, 2010.

Surisetty, V.R., et al, "Effect of Textural Properties of Carbon Supports on Alkali-promoted Trimetallic Co—Rh—Mo Sulfide catalysts for Higher Alcohols Synthesis from Synthesis Gas", 60th Canadian Chemical Engineering Conference (CSCE2010), Saskatoon, Saskatchewan, Canada, Oct. 24-27, 2010.

Surisetty, et al, "An intrensic kinetic model for higher alcohols synthesis from synthesis gas using sulfided alkali-promoted Co—Rh—Mo trimetallic catalyst supported on MWCNTs", CHEMCON, 2010, Annamalinager, Tamil Nadu, India, Dec. 27-29, 2010.

Surisetty, V.R. et al., "Structural Characterization and Catalytic Performance of Alkali and Metal Promoters (Co and Rh) on MoS2 Catalysts for Higher Alcohols Synthesis Reaction", Canadian Light Source 13th Annual User's Meeting, Jun. 17-18, 2010, Saskatoon, Saskatchewan, Canada.

* cited by examiner

Figure 11

(a) Chain initiation $$CO \updownarrow s \quad 0.5H_2 \updownarrow s$$
$$CO_s + H_s \underset{s}{\overset{}{\leftrightarrow}} CHO_s \underset{s}{\overset{H_s}{\leftrightarrow}} CH_2O_s \underset{s}{\overset{H_s}{\leftrightarrow}} R_1O_s$$

(b) Chain propagation $$R_iO_s \xrightarrow[-(H_2O + 2s)]{2H_s} R_{is} \xrightarrow[-s]{CO_s} R_iCO_s \xrightarrow[-2s]{2H_s} R_{i+1}O_s$$

(c) Chain termination $$R_1O_s \underset{-s}{\overset{H_s}{\leftrightarrow}} CH_3OH$$

$$R_{i+1}O_s \xrightarrow[-2s]{H_s} R_{i+1}OH$$

$$R_{is} \xrightarrow[-2s]{H_s} C_iH_{2i+2}$$

$$R_{is} \xrightarrow[-H_s]{} C_iH_{2i}$$

Figure 20
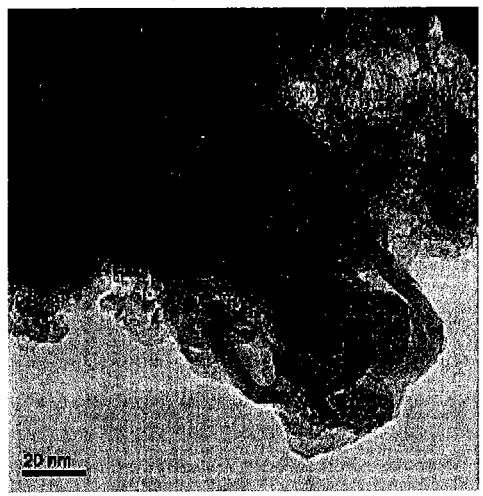
a.
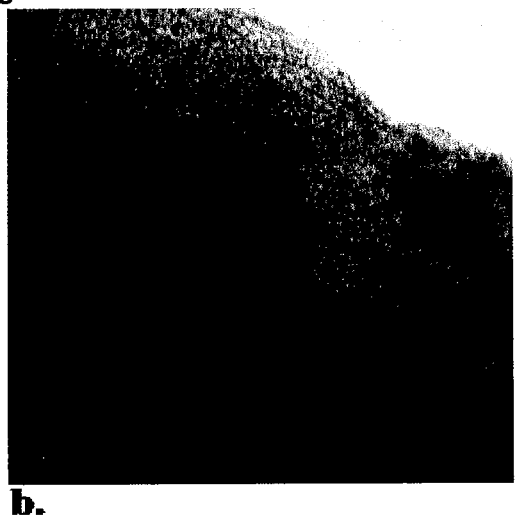
b.
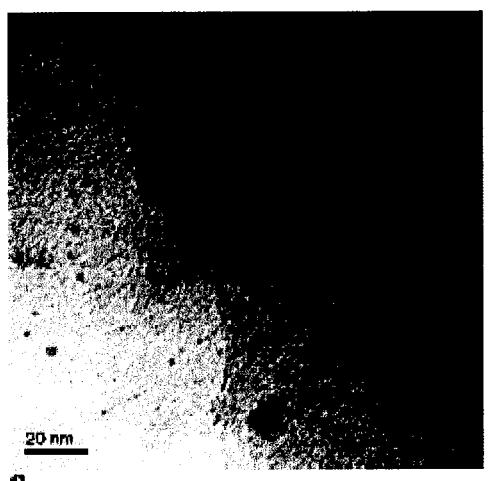
c.
d.
e.

Figure 40
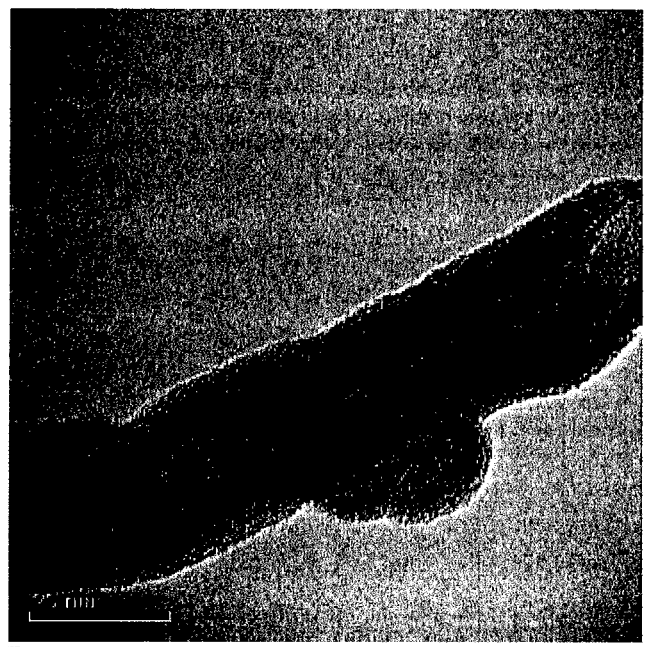

Figure 41
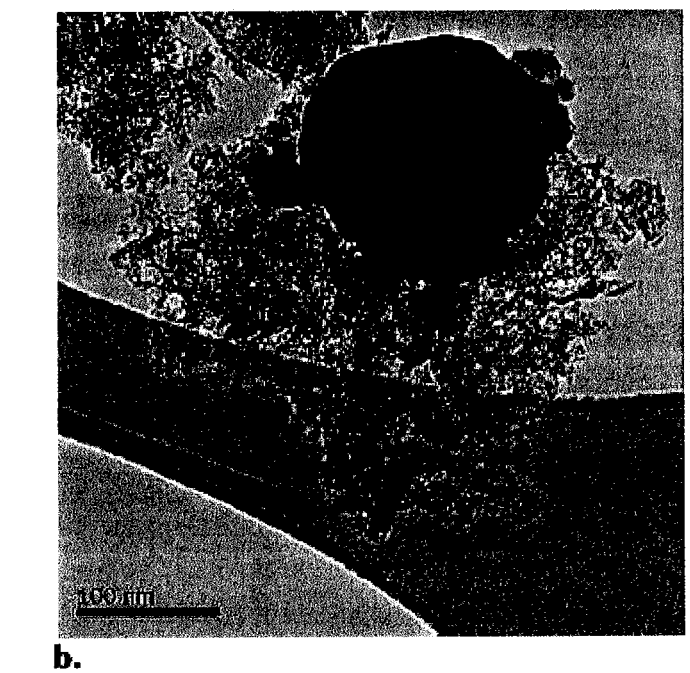

CATALYSTS FOR THE CONVERSION OF SYNTHESIS GAS TO ALCOHOLS

RELATED APPLICATIONS

This application claims the benefit under 35 USC §119(e) of U.S. provisional application No. 61/482,669 filed on May 5, 2011, which is incorporated herein by reference in its entirety.

FIELD OF THE APPLICATION

The present application generally relates to the field of catalysts for the chemical conversion of synthesis gas to alcohols.

BACKGROUND OF THE APPLICATION

The synthesis of higher alcohols from synthesis gas by direct catalysis was recognized in 1923 by Frans Fischer and Hans Tropsch. They reported that a mixture of alcohols, aldehydes, ketones, fatty acids, and esters were formed when the reaction between CO and $H_2$ was performed at pressures ranging from 10 to 14 MPa and at temperatures of 400 to 500° C. in the presence of an alkalized iron oxide catalyst. They named the mixture as synthol and the process as the synthol process.[1] In 1930, Frolich and Cryder reported the formation of alcohols higher than methanol by passing syngas over a Zn:Mn:Cr, 1:1.1:1.03 catalyst. They reported that methanol forms from a formaldehyde intermediate and that the higher alcohols form from the methanol through a stepwise condensation reaction.[2] In the 1940s, Du Pont developed an alkalized Mn—Cr catalyst to synthesize methanol and higher alcohols from syngas for commercial purposes.[3] In the late 1940s, Farbenindustrie et al. introduced the Synol process for the manufacture of alcohols from syngas. This process uses low pressures around 2 MPa with higher productivity of alcohols by modifying the Fischer-Tropsch alkalized iron catalyst.[4] Natta et al. reviewed the synthesis of higher alcohols from CO and $H_2$, in 1957 and reported that the synthesis of higher alcohols was always related to the presence of strongly basic substances.[5]

Higher alcohols synthesis from CO hydrogenation is of interest as the alcohol mixture is an effective octane number enhancer for motor fuels.[6,7] The catalytic systems used for the higher alcohols synthesis reaction from synthesis gas are divided into two groups, based on the product distribution.[8] Alkali-doped high temperature ZnCrO-based and low temperature Cu-based catalytic systems produce mainly methanol and higher branched alcohols.[9] The second group developed from Fe, Ni, or Co modified low temperature and low pressure methanol synthesis catalysts and alkali-modified $MoS_2$-based catalysts yields a series of linear primary alcohols and gaseous hydrocarbons with Anderson-Schulz-Flory (ASF) carbon number distributions.[10]

Alkali-modified $MoS_2$-based catalysts are commercially attractive among different higher alcohols synthesis catalysts, due to their excellent sulfur resistance and high activity for water-gas shift (WGS) reactions.[11] The promotion of Pt group metals, especially Rh in Mo-based catalysts, improved activity toward the formation of higher alcohols.[12] The Mo promotion over the $Rh/Al_2O_3$ catalyst increased its activity favoring the formation of oxygenates.[13] Li et al.[14] explained that a strong interaction occurred between the rhodium modifiers with the supported K—Mo—O species in the oxidic Rh modified Mo—$K/Al_2O_3$ samples and concluded that the coexistence of cationic and metallic Rh stabilized by this interaction may be responsible for the increased selectivity toward higher alcohols ($C_{2+}OH$). Foley et al.[15] suggested that the interaction between Rh and Mo leads to the formation of electron-poor sites that are responsible for the formation of alcohols. Shen et al.[16] investigated the promotion effect of Mo in Rh—$Mo/SiO_2$ catalysts in an oxided state and suggested that Mo promotion either leads to the oxidation of Rh and consequent stabilization $Rh^{1+}$ ions or the coverage of Rh sites by Mo oxides, depending on the interaction between Rh and Mo. Depending on the status of the rhodium species, properties of alkali promoters, nature of the support, and reaction conditions, the rhodium species are capable of catalyzing dissociation, insertion, and CO hydrogenation.[17]

The addition of 3d transition metals, such as Co and Ni to $MoS_2$, has a strong promotion effect on the CO hydrogenation reaction.[18,19] The promotion of Co (or Ni) on $MoS_2$ leads to the formation of three different phases: $MoS_2$, $Co_9S_8$ ($Ni_3S_2$), and a mixed Co (Ni)—Mo—S phase.[20] The formation of the Co (Ni)—Mo—S phase is related to the electron donation from Co (Ni) to Mo decreasing the Mo—S bond strength to an optimum range, thus significantly increasing the activity of the catalyst.[21] The Co-promoted alkali-modified molybdenum sulfide catalysts showed better activity and selectivity of higher alcohols compared to that of Ni.[22] The Ni promotion on alkali-modified $MoS_2$ catalysts favors the formation of hydrocarbon as Ni is a methanation component.[23] Fujumoto et al.[24] found that equal amounts of hydrocarbons and alcohols resulted from the CO hydrogenation reaction over the $K/Co/Mo/Al_2O_3$ and $K/Co/Mo/SiO_2$ catalysts. Li et al.[10] introduced Co as a promoter to activated carbon-supported K—$MoS_2$ catalysts and found that Co exists mainly in the form of the Co—Mo—S phase at low Co loading and partly in a $Co_9S_8$-like structure at high Co content. The addition of Co to alkali-modified $MoS_2$ catalysts enhanced the $C_1 \rightarrow C_2$ homologation step that leads to the formation of ethanol as the dominant product.[25] Wong et al.[26] investigated the incorporation of Rh into reduced $K/Co/Mo/Al_2O_3$ catalysts and found that the activity and selectivity of alcohols improved significantly due to the interaction of cationic Rh species with the Mo species.

Catalyst support plays an important role for reactions involving hydrogen as a reactant or product. Supports such as activated carbon,[27] clay,[28] $Al_2O_3$,[29] $SiO_2$,[30] $CeO_2$,[31] $ZrO_2$,[32] and combinations of different metal oxides[33] have been studied in detail as supports to different catalyst systems for higher alcohols synthesis reactions from synthesis gas. Acidic metal oxide supports, such as $Al_2O_3$ and $ZrO_2$, favor the formation of hydrocarbons by suppressing the reaction rate of alcohols and their surface acidity causes deactivation by coke formation.[34,35] Concha et al.[36] compared the effects of different supports ($SiO_2$, $Al_2O_3$, activated carbon, and $CeO_2$) on reduced and sulfided molybdenum catalysts and found that hydrocarbon selectivity on activated carbon-supported catalysts was much less than that of others. Murchison et al.[37] found that $MoS_2$ supported on activated carbon showed alcohol selectivity about six times higher than that of the alumina-supported catalyst. Activated carbon has many advantages as a catalyst support because of its large surface area, limited interaction between the support and the active material due to the inertness of the graphitic surface, resistance to acidic or basic media, and stability at high temperatures and pressures.[38] However, activated carbon supported catalysts have a microporous structure (pore size<2 nm) that causes pore plugging due to the formation of coke and deactivation of the catalyst, which results in transport limitation in the reaction.[39] Also, activated carbons have 10-15% ash content, depending on the nature of the precursor used.[40]

Carbon, in the form of multiwalled carbon nanotubes (MWCNTs), is an alternative heterogeneous catalyst support having an inert graphite nature and high temperature stability.[41,42,43]

SUMMARY OF THE APPLICATION

In the present application, it has been demonstrated that the addition of Co and Rh metal promoters to alkali-promoted $MoS_2$ catalysts supported on, for example MWCNTs, display improved catalytic performance towards higher alcohols formation from synthesis gas. The alkali-promoted trimetallic Co—Rh—Mo catalyst system is representative of a class of trimetallic catalysts that are advantageous as they have increased activity and selectivity for the formation of higher alcohols, especially ethanol.

Accordingly, the present application includes a catalyst comprising the Formula (I):

$$A\text{-}M^1\text{-}M^2\text{-}M^3 \qquad (I)$$

wherein A is an alkali metal;
$M^1$ is selected from Co, Ni and Fe;
$M^2$ is selected from Rh, Ru and Pd; and
$M^3$ is selected from Mo;
wherein the catalyst is supported on a carbon-based material.

In an embodiment the catalyst comprises the Formula A-Co—Rh—Mo, wherein A is an alkali metal, for example K, and the catalyst is supported on a carbon-based support selected from activated carbon and multi-walled carbon nano-tubes (MWCNTs).

In a further embodiment, the present application includes an alkali metal-promoted trimetallic catalyst for higher alcohol synthesis from synthesis gas, the catalyst comprising Co, Rh and Mo. In an embodiment of the application the alkali metal is K and is present in an amount of about 8 wt % to about 10 wt %. In a further embodiment, the trimetallic catalyst comprises about 3.5 wt % to about 7 wt % Co, about 0.5 wt % to about 2.5 wt % Rh and about 14 wt % to about 16 wt % Mo. In a further embodiment, the catalyst of the present application, comprises about 9 wt % K, about 4.5% Co, about 1.5 wt % Rh and about 15 wt % Mo, the remainder being substantially the carbon-based support.

In an embodiment of the application, the catalyst comprises, consists essentially of, or consists of, K, Co, Rh and Mo, on a carbon based support.

It is an embodiment of the application that the carbon-based support is MWCNTs. MWCNTs display unique properties such as meso/macroporous structures that mitigate transport limitations, and provide uniform and straight pores that allow greater metal dispersion, high mechanical strength, and thermal conductivity.

In another embodiment, the catalysts of the application are prepared by impregnation using an incipient wetness impregnation method. For example, metal precursors dissolved in aqueous solutions are used to impregnate the support, followed by drying and stabilizing. In an embodiment, the support is first impregnated with an aqueous solution of the alkali metal salt, followed by drying and stabilizing. Then the support is further impregnated with precursors for $M^1$, $M^2$ and $M^3$ followed by drying and stabilizing. It is an embodiment of the application that the catalyst is used in its sulfided state for higher alcohol synthesis from synthesis gas. Sulfidation of the catalyst is performed, for example by treating the catalyst with an $H_2S/H_2$ gas mixture.

In an embodiment of the present application, the particle size of the catalysts is about 140 μm to about 220 μm.

The present application also includes a process for producing higher alcohols from synthesis gas, the method comprising reacting the gas with a catalyst of the present application under conditions for the formation of higher alcohols.

Other features and advantages of the present application will become apparent from the following detailed description. It should be understood, however, that the detailed description and the specific examples while indicating preferred embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings in which:

FIG. 11 shows a reaction scheme for higher alcohols synthesis using the CO insertion mechanism.

FIG. 20 shows TEM images of exemplary supported catalysts a. AC-Darco; b. AC-$RX_3$ extra; c. AC-Fluid; d. AC-CGP super; e. MWCNT.

FIG. 40 shows a TEM image of an exemplary MWCNT-supported catalyst; a. Fresh catalyst, b. Spent catalyst.

FIG. 41 shows a TEM image of an exemplary activated carbon-supported catalyst; a. Fresh catalyst, b. Spent catalyst.

DETAILED DESCRIPTION OF THE APPLICATION

I. Definitions

Figure 1:
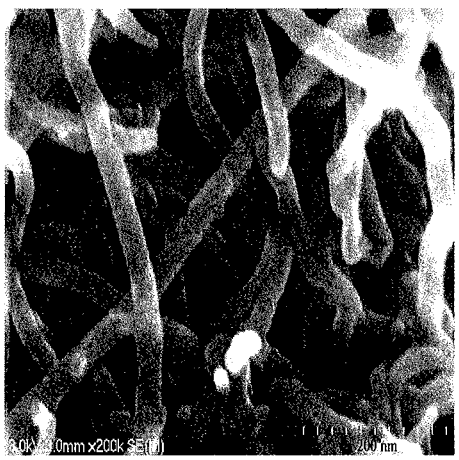
FIG. 1 is an SEM image of an exemplary MWCNT supported catalyst of the application.

Unless otherwise indicated, the definitions and embodiments described in this and other sections are intended to be applicable to all embodiments and aspects of the disclosure herein described for which they are suitable as would be understood by a person skilled in the art.

As used in this application, the singular forms "a", "an" and "the" include plural references unless the content clearly dictates otherwise. For example, an embodiment including "a catalyst" should be understood to present certain aspects with one catalyst, or two or more additional catalysts.

In embodiments comprising an "additional" or "second" component, such as an additional or second catalyst, the second component as used herein is chemically different from the other components or first component. A "third" component is different from the other, first, and second components, and further enumerated or "additional" components are similarly different.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the desired product. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "wt %" as used herein, unless otherwise indicated, means percent by weight of the entire catalyst including the support.

The term "higher alcohols" as used herein refers to hydrocarbon alcohols with a carbon number greater than or equal to 2 ($C_{2+}$ alcohols), including for example, ethanol, propanol, butanol, pentanol and the like.

The term "alkali metal" as used herein refers to an element in Group I (modern IUPAC naming) of the periodic table, including lithium (Li), sodium (Na), potassium (K), rubidium (Rb) and cesium (Cs). In an embodiment, the alkali metal is K.

The term "synthesis gas" as used herein means a gas comprising, as its major components, carbon monoxide (CO) and hydrogen ($H_2$). For example synthesis gas may comprise 5-50% CO and 5-50% $H_2$. Synthesis gas may further comprise hydrogen sulfide ($H_2S$), carbon dioxide ($CO_2$), water ($H_2O$), methane ($CH_4$), higher hydrocarbons, nitrogen ($N_2$) and other contaminants. Synthesis gas is available, for example, from the gasification of biomass (a thermal-chemical process that uses partial oxidation to convert organically derived feedstock into synthesis gas); gasification of hydrocarbonaceous materials such as coal, high specific gravity oils, or natural gas; as a by-product of partial combustion cracking of hydrocarbons; by steam reforming of liquid or gaseous hydrocarbons; through the water-gas shift reaction; or some combination of these. The CO and $H_2$ may also be generated separately and combined.

The term "dry" or "drying" as used herein refers to the removal of essentially all of the solvent or solvents from a material. Suitable conditions for drying the supports or catalysts of the present application will be those sufficient for driving off essentially all of the solvent or solvents used in a previous application step.

The term "stabilizing" as used herein refers to treating the catalysts of the application under conditions to increase stability, such as by curing. Such conditions typically comprise applying heat for a period of time to increase the stability of the catalysts.

II. Catalysts of the Application

Multi-walled carbon nanotubes (MWCNTs) and activated carbon were used as supports for Co-promoted, alkali-modified, Rh—Mo catalysts. The catalysts were extensively characterized in both oxide and sulfide phases. Diffraction peaks were observed in the X-ray diffraction (XRD) patterns of the sulfided alkali-modified trimetallic catalysts, due to the characteristic reflections of the K—Mo—S mixed phase. $H_2$-temperature programmed reduction (TPR) profiles showed that the reduction behavior of metal species was improved with the addition of Co. The activated carbon-supported trimetallic catalysts showed less activity and selectivity compared to the MWCNT-supported catalyst, and metal dispersions were higher on the MWCNT-supported catalysts. The MWCNT-supported, alkali-promoted trimetallic catalyst with 4.5 wt % Co showed the highest total alcohols yield of 0.244 g/(g of cat.)/h, ethanol selectivity of 20.1%, and higher alcohols selectivity of 31.4% at 320° C. and 8.28 MPa using a gas hourly space velocity (GHSV) of 3.6 m³ (STP)/(kg of cat.)/h. A maximum total alcohol yield of 0.261 g/(g of cat.)/h and selectivity of 42.9% were obtained on the 4.5 wt % Co—Rh—Mo—K/MWCNT catalyst, at a temperature of 330° C. The total alcohol yield increased from 0.163 to 0.256 g/(g of cat.)/h with increased pressure from 5.52 MPa (800 psig) to 9.65 MPa (1400 psig) over the 4.5 wt % Co—Rh—Mo—K/MWCNT catalyst.

Accordingly, the present application includes a catalyst comprising the Formula (I):

$$A\text{-}M^1\text{-}M^2\text{-}M^3 \qquad (I)$$

wherein A is an alkali metal;
$M^1$ is selected from Co, Ni and Fe;
$M^2$ is selected from Rh, Ru and Pd; and
$M^3$ is selected from Mo;
wherein the catalyst is supported on a carbon-based material.

In an embodiment the catalyst comprises the Formula A-Co—Rh—Mo, wherein A is an alkali metal, and the catalyst is supported on a carbon-based support selected from activated carbon and multi-walled carbon nano-tubes (MWCNTs). In an embodiment of the application, the alkali metal is K.

In a further embodiment, the present application includes an alkali metal-promoted trimetallic catalyst for higher alcohol synthesis from synthesis gas, the catalyst comprising Co, Rh and Mo. In an embodiment of the application the alkali metal is K and is present in an amount of about 8 wt % to about 10 wt %, or about 9 wt %. In a further embodiment, the trimetallic catalyst comprises about 3.5 wt % to about 7 wt %, or about 4.5 wt %, Co, about 0.5 wt % to about 2.5 wt %, or about 1.5 wt % Rh and about 14 wt % to about 16 wt %, or about 15 wt %, Mo. In a further embodiment, the catalyst of the present application, comprises about 9 wt % K, about 4.5% Co, about 1.5 wt % Rh and about 15 wt % Mo, the remainder being substantially the carbon-based support.

In an embodiment of the application, the catalyst comprises, consists essentially of, or consists of K, Co, Rh and Mo, on a carbon based support.

It is an embodiment of the application that the carbon-based support is MWCNTs. MWCNTs display unique properties such as meso/macroporous structures that mitigate transport limitations, and provide uniform and straight pores that allow greater metal dispersion, high mechanical strength, and thermal conductivity. Prior to impregnation with metals, it is an embodiment that the support is treated with acid, for example nitric acid ($HNO_3$), including about 30% $HNO_3$, followed by washing, for example with distilled water, to remove residual acid and drying, for example at about 100° C. to about 150° C., or about 120° C., for a time sufficient to dry the support.

In another embodiment, the catalysts of the application are prepared by impregnation using an incipient wetness impregnation method. For example, metal precursors dissolved in aqueous solutions are used to impregnate the support, followed by drying and stabilizing. For example, an acid treated support is first impregnated with an aqueous solution comprising required amounts of the alkali metal salt, for example, potassium carbonate ($K_2CO_3$), followed by drying, for example at about 100° C. to about 150° C., or about 120° C., for a time sufficient to dry the support, and stabilizing, for example in flow of an inert gas, such as Ar, at a flow rate of about 25 to 75 ml/min or about 50 ml/min, at a temperature of about 250° C. to about 400° C., or about 300° C., at a heating rate of about 5-20° C./min, or about 10° C./min, for about 2 to about 10 hours, or about 4 hours. The support is then further impregnated with aqueous solutions containing the required amounts of the $M^1$, $M^2$ and $M^3$ precursors followed by drying, for example at about 100° C. to about 150° C., or about 120° C., for a time sufficient to dry the support, and stabilizing, for example in flow of an inert gas, such as Ar, at a flow rate of about 25 to 75 ml/min or about 50 ml/min, at a temperature of about 300° C. to about 550° C., or about 450° C., at a heating rate of about 5-20° C./min, or about 10° C./min, for about 6 to about 24 hours, or about 12 hours. In an embodiment, the support is first impregnated with an aqueous solution of the alkali metal salt, followed by drying and stabilizing. Then the support is further impregnated with precursors for $M^1$, $M^2$ and $M^3$ followed by drying and stabilizing.

The impregnation will typically be carried out until the catalyst support has absorbed a volume of impregnating solution equal to at least about 100% of its calculated pore volume, suitably to where conditions of incipient wetness are attained. By incipient wetness is meant that the support has absorbed an amount of solution generally equivalent to its calculated pore volume. Pore volume is a discernible quantity that can be measured directly or indirectly by known techniques such as porosimetry. The volume of impregnating solution contemplated will vary from 10% to 1000% of the calculated pore volume of the catalyst. Suitably, the volume of treatment solution will be from 30% to 200%, or from about 70% to 100% of the calculated pore volume of the catalyst.

In an embodiment, the impregnating solution will remain in contact with the support for from 1 minute to 24 hours, suitably from about 5 to 120 minutes. The time required for the treatment will vary depending on factors such as the metal loading of the support being treated, the quantity thereof, the composition and volume of the impregnating solution, the reactor configuration and the like. In an embodiment, the treatment is carried out at a temperature from about 0° C. to about 100° C., or from room temperature, i.e. 20-25° C., to about 80° C. The pressure is not particularly critical with atmospheric pressure being suitable.

Once the support has absorbed the desired volume of impregnating solution, it undergoes oxidation in the presence of the impregnating solution. It is an embodiment of the application that the catalyst is used in its sulfided state for higher alcohol synthesis from synthesis gas. Sulfidation of the catalyst is performed, for example by treating the oxide catalyst with $H_2S$. In an embodiment sulfidation is carried out at the same time as the catalyst is activated by reduction prior to catalyst use to convert synthesis gas to higher alcohols. In this embodiment the oxide catalyst is treated with an $H_2S/H_2$ gas mixture, for example about 5 mole % to about 20 mole %, or about 10 mole % $H_2S$ in $H_2$ gas, at a temperature of about 300° C. to about 550° C., or about 450° C., at a heating rate of about 1-5° C./min, or about 2° C./min, for about 2 to about 10 hours, or about 4 hours.

In an embodiment of the application, the precursor compound for K is potassium carbonate ($K_2CO_3$), the precursor compound for Mo is ammonium heptamolybdate tetrahydrate (($NH_4$)$_6Mo_7O_{24}$), the precursor compound for Co is cobalt acetate tetrahydrate (Co($CH_3$COO)$_2$), and the precursor for Rh is rhodium chloride hydrate ($RhCl_3$), although a person skilled in the art would appreciate that other precursor compounds can be used in place of these compounds without deviating from the scope of the present application. These precursor compounds are commercially available.

In an embodiment of the present application, the average particle size of the catalysts is about 140 μm to about 220 μm, or about 147 μm to about 210 μm.

In another embodiment of the present application there is included catalyst particles that comprise, consist essentially of, or consist of, an alkali-modifier, a Co-promoter, and a Rh—Mo sulfide catalyst wherein the particles have an average particle size of about 140 μm to about 220 μm, or about 147 μm to about 210 μm.

The MWCNT-supported alkali-promoted Co—Rh—Mo trimetallic catalysts of the application, showed enhanced CO hydrogenation capability, compared to that of corresponding MWCNT-supported alkali-promoted Rh—Mo bimetallic catalyst. With the addition of 4.5 wt % Co on the MWCNT-supported 1.5 wt % Rh, 15 wt % Mo, and 9 wt % K catalyst, the total alcohols STY increased to 0.244 g/(g of cat.)/h and the total hydrocarbons STY decreased to 0.251 g/(g of cat.)/h. The methanol, ethanol, and higher alcohols selectivities, respectively, increased from 5.4%, 16.0%, and 24.6%, respectively, over the alkali-promoted bimetallic Rh—Mo/MWCNT catalyst to 6.7%, 20.1%, and 31.4%, respectively, on the MWCNT-supported trimetallic catalyst promoted with 4.5 wt % Co. From the CO chemisorption results, it was observed that incorporation of 4.5 wt % Co to the alkali-modified bimetallic Rh—Mo catalyst supported on MWCNTs increased the CO uptake from 135 to 237 μmole/(g of cat.). Also, Co promotion to Rh—Mo—K/MWCNT catalyst increased the metal dispersion from 39.5 to 49.8% favoring the formation of fine particles. These results, coupled with XRD data, confirm that incorporating Co metal increased the number of active sites responsible for the formation of alcohols.

III. Processes of the Application

The catalysts of the present application are useful for the conversion of synthesis gas to alcohols (in particular higher alcohols), in the so-called Fischer-Tropsch reaction.

The present application therefore includes a process for producing higher alcohols from synthesis gas, the process comprising reacting the gas with a catalyst of the application under conditions for the formation of higher alcohols.

In an embodiment of the present application the conditions for the formation of higher alcohols comprise a temperature of about 300° C. to about 350° C., or about 330° C.; a pressure of about 5.5 Mpa to about 10 MPa, or about 8.0 MPa to about 9.0 MPa; and a gas hourly space velocity (GHSV) of about 2.5 m$^3$ (STP)/(kg of cat)/h to about to about 4.5 m$^3$ (STP)/(kg of cat)/h, or about 3.8 m$^3$ (STP)/(kg of cat)/h.

In a further embodiment of the present application the molar ratio of $H_2$:CO in the synthesis gas is about 1:1 to about 1.5:1, or about 1.25:1.

In accordance with the present application, and as described above, the catalysts of the present application are activated and sulfided in a single step prior to use to convert synthesis gas to higher alcohols. In this embodiment the oxide catalysts are treated with an $H_2S/H_2$ gas mixture, for example about 5 mole % to about 20 mole %, or about 10 mole % $H_2S$ in $H_2$ gas; at a temperature of about 300° C. to about 550° C., or about 450° C.; at a heating rate of about 1-5° C./min, or about 2° C./min; for about 2 to about 10 hours, or about 4 hours.

It is a further optional step within the scope of the present application to passivate the treated catalyst after the activation/sulfidation with $H_2S/H_2$ gas mixture has been carried out. The passivation may be carried out by contacting the catalyst with a gas containing carbon monoxide, or carbon monoxide and hydrogen, under conditions such that carbon monoxide does not significantly decompose and is not hydrogenated to a material degree. Such conditions, for example, would be a temperature below about 150° C., or about 25° C. to about 100° C., and pressure below about 20 atm, or about 1 to about 10 atm and the GHSV would be from about 1 V/HrN to about 1,000 V/HrN, or about 10 V/HrN to about 500 V/HrN, expressed as standard volumes of the gas or gas mixtures (25° C., 1 atm) per hour per volume of catalyst, respectively. It will be appreciated that some decomposition or hydrogenation, respectively, of the carbon monoxide may take place regardless of the precautions taken by the operator. However, it has been found that, typically, significant decomposition/hydrogenation will not take place wherein the concentration of carbon monoxide or carbon monoxide and hydrogen in the feed gas does not exceed about 5% by volume. Other passivating agents include, for example, traces of oxygen or carbon dioxide.

In another embodiment the process of the application is carried out as a continuous process with a catalyst of the present application in a suitable reactor, for example a fixed bed reactor, a slurry reactor, a loop reactor, a bubble-column reactor or a fluid-bed reactor. Accordingly, the present application also includes a reactor comprising a catalyst of the application.

Effluent reactant gases and liquids from the process may be separated and recycled, if desired, for further alcohol synthesis. Industrial methods of collecting the products are well known and include fractional distillation and the like. Auxiliary equipment is conventional and known to those skilled in the art.

The following non-limiting examples are illustrative of the present application:

EXAMPLES

Example 1

Preparation and Characterization of K-Promoted Trimetallic Catalysts

Materials and Methods
(a) Preparation of K-Promoted Trimetallic Catalysts

MWCNTs (M. K. Nano, surface area 178 m$^2$/g, pore volume 0.54 cm$^3$/g) and activated carbon (Aldrich, surface area 655 m$^2$/g, pore volume 0.93 cm$^3$/g) were used as supports for the preparation of the catalysts. Prior to impregnation, the support was treated with 30% $HNO_3$ reflux at 100° C. overnight, washed with distilled water several times, and dried at 120° C. for 6 h. The oxide samples were prepared by the sequential pore volume impregnation method using ammonium heptamolybdate tetrahydrate (Sigma-Aldrich), potassium carbonate (Aldrich), cobalt acetate tetrahydrate (Alfa-Aesar), and rhodium chloride hydrate (Aldrich) as precursors for Mo, K, Co, and Rh, respectively. At the first step, the support was impregnated with an aqueous solution of $K_2CO_3$, followed by drying at 120° C. for 2 h and stabilizing in an argon flow of 50 ml/min at 300° C., at a heating rate of 10° C./min for 4 h. The support was further impregnated with aqueous solutions containing the required amounts of $(NH_4)_6Mo_7O_{24}$, $Co(CH_3COO)_2$, and $RhCl_3$ followed by drying at 120° C. for 2 h and stabilizing in an argon flow of 50 ml/min at 450° C., at a heating rate of 10° C./min for 12 h. The sulfide samples were obtained by heat-treating the oxide precursors in a flow of 10 mole % $H_2S$ in $H_2$ gas at 450° C., at a heating rate of 2° C./min for 4 h.
(b) Characterization of K-Promoted Trimetallic Catalysts The surface area, pore volume, and average pore diameter of oxide samples were measured by $N_2$ physisorption at 77 K using a Micromeritics ASAP 2000. Approximately 0.2 g of sample was used for each analysis. The moisture and other adsorbed gases present in the sample were removed before analysis by degassing the sample at 200° C. for 2 h under 66.7 Pa (500 mmHg). The sample was then evacuated at 2.67 Pa (20 μm Hg) before $N_2$ adsorption.

The content of Mo, Co, and Rh of the oxide catalysts was determined using a Perkin-Elmer ELAN 5000 inductively coupled plasma mass spectroscopy (ICP-MS) instrument.

Powder X-ray diffraction (XRD) analysis patterns of oxide and sulfide forms of samples were recorded on a Rigaku X-ray diffraction instrument with nickel-filtered Cu KR radiation (λ=0.1541 nm). Each sample was scanned at a rate of 0.05°/s, with 2θ varying from 10 to 80°. To obtain the XRD patterns in sulfided form, the catalysts were first sulfided for 6 h at 450° C., at a heating rate of 2° C./min using a gaseous mixture containing 10 mole % $H_2S$ in $H_2$ at a flow rate of 50 ml/min. After sulfidation, the catalysts were cooled to room temperature in a flow of He and the sample was transferred to sample holders under protection of He.

Carbon monoxide was used as a probe molecule to determine the number of accessible surface metal atoms present on the sulfided catalysts. The CO uptake (μmole/g of cat.) measured from CO chemisorption is equivalent to the number of active metal atoms that are accessible to the reactant molecules. The stoichiometric coefficient (CO to metal ratio) of 1 was used, and the extent of reduction was assumed to be 100% in metal dispersion calculations. The carbon monoxide uptake on the sulfided catalysts was measured using the Micromeritics ASAP 2000 instrument. Prior to the CO chemisorption measurement, 0.2 g of sample was sulfided in situ, using 10 mole % $H_2S$ in $H_2$ at 400° C. for 4 h. The sample was then evacuated at 120° C. until the static pressure remained less than $6.6 \times 10^{-4}$ Pa. Chemisorption was performed by passing pulses of CO over the sample to measure the total gas uptake at 35° C.

To study the reducibility of the metal oxides in the catalysts, temperature programmed reduction (TPR) profiles of the catalysts were performed. For each analysis, approximately 0.2 g of sample was used, which was first purged in a flow of argon at 170° C. to remove traces of water, and then cooled to 40° C. The TPR of each sample was performed using a 3.1 mole % $H_2$ in He stream at a flow rate of 30 mL/min at atmospheric pressure using a CHEMBET 3000 TPD-TPR analyzer equipped with a thermal conductivity detector, heating at a linearly programmed rate of 10° C./min up to 800° C.

The oxide samples were characterized by scanning electron microscopy (SEM) using a Phillips SEM-505 scanning electron microscope operating at 300 kV in SE display mode. The outer diameter of the nanotubes was measured using Digital micrograph software (version 3.6.5, Gatan Inc.).

The morphology of the oxide samples was characterized by transmission electron microscopy (TEM) investigations, using a Philips CM20 (100 kV) transmission electron microscope equipped with a NARON energy-dispersive spectrometer with a germanium detector.

(c) Higher Alcohols Synthesis

A single-pass tubular downflow fixed bed reactor of 450-mm length and 22-mm inside diameter made of inconel tube was used to perform higher alcohols synthesis reactions. The reactor was packed with 2 g of catalyst diluted with 12 ml of 90 mesh size silicon carbide and housed in an electric furnace controlled by a temperature controller. The reactor was pressurized with He to 3.44 MPa (500 psig) and the sulfidation, together with the reduction, was carried out for 6 h at 450° C. at a heating rate of 2° C./min using a gas mixture containing 10 mole % $H_2S$ in $H_2$ and a flow rate of 50 ml/min. The temperature was then lowered to the reaction temperature, and the system pressurized to the reaction conditions. The feed gas mixture CO (45 mole %), $H_2$ (45 mole %), and Ar (10 mole %) was passed through mass flow controllers and the higher alcohols synthesis reaction was carried out at steady-state under the reaction conditions of 300-340° C., 5.51 (800 psig) to 9.65 MPa (1400 psig), and a gas hourly space velocity (GHSV) of 3.6 $m^3$ (STP)/(kg of cat.)/h over a period of 24 h. The product gas was cooled to 0° C. and separated into gas and liquid phases at the reaction pressure. The CO conversion and other gaseous products were monitored with a time interval of 1 h. The liquid products were collected at the end of the reaction and analyzed with a Varian 3400 gas chromatograph equipped with a capillary column and a flame ionization detector (FID). The volume and weight of liquid products were measured to check the mass balance. The gaseous products were analyzed online on a Shimadzu gas chromatograph through a sampling valve. Using Ar as an internal standard, the CO conversion was calculated and the overall mass balance of the reaction was determined. The experiments were repeated at least twice to check reproducibility and to confirm that the results obtained were within the experimental error of ±2.5%.

Results and Discussion (a) Characterization of K-Promoted Trimetallic Catalysts

Scanning electron microscopy was used to identify the growth of the MWCNTs. FIG. 1 shows the surface topology of the grown carbon nanotubes in bundles. The outside diameter of the MWCNTs clearly shows that the nanotubes are multiwalled and have a structure with several walls of graphitic carbons in concentric circles. The nanotubes are found to be tangled. The outer diameter of the nanotubes, as measured from the micrograph ranges from 10-30 nm.

Figure 2:
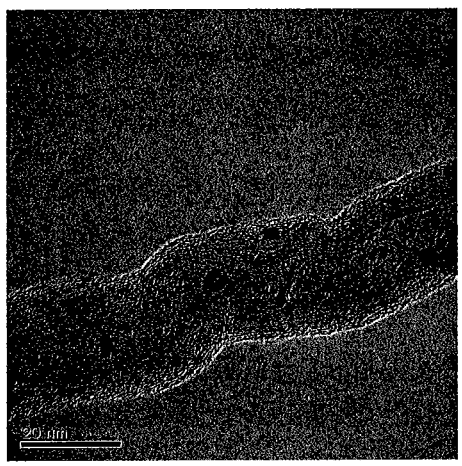
FIG. 2 is a TEM image of an exemplary MWCNT supported catalyst of the application.

TEM images of the MWCNT-supported catalysts were recorded and, as shown in FIG. 2, revealed that the catalyst particles are well dispersed both inside the carbon nanotubes and on the outside of the tube walls. The carbon nanotubes are multiwalled, with inner diameters in the range of 5-12 nm and wall thickness in the range of 3 to 8 nm. The particle sizes of the metal species that are inside and outside of the tubes are in the range of 1-3 nm.

Table 1 shows the results for surface area, total pore volume, and average pore diameter of the stabilized catalysts. After acid treatment, the BET surface area of the MWCNTs increased from 178 to 220 $m^2/g$, whereas, an increase from 655 to 676 $m^2/g$ was observed in the BET surface area of activated carbon. The MWCNT-supported bimetallic (1.5 wt % Rh and 15 wt % Mo) catalyst promoted with 9 wt % K showed a BET surface area of 77 $m^2/g$ and a total pore volume of 0.30 $cm^3/g$. Increasing the amount of Co from 4.5 to 6 wt % decreased the BET surface area of the MWCNT-supported, alkali-promoted trimetallic catalysts from 68 to 59 $m^2/g$ and the total pore volume from 0.24 to 0.20 $cm^3/g$. After impregnating with metal species, a drastic fall in surface area over the activated carbon-supported catalysts was observed. A BET surface area of 97 and 83 $m^2/g$ and a total pore volume of 0.16 and 0.11 $cm^3/g$ were observed over the activated carbon-supported, alkali-promoted trimetallic catalysts that are promoted with 4.5 and 6 wt %, respectively.

The Co, Rh, and Mo contents of the stabilized catalysts measured by ICP-MS are reported in Table 1, along with the targeted compositions. The measured contents of the prepared catalysts are slightly lower compared to targeted values, which may be due to the hygroscopic nature of precursors. For the activated carbon-based catalysts, the deviation is greater, indicating that metal particles are not uniformly dispersed on this support.

The results of the CO chemisorption measurements are also given in Table 1. The CO uptake increased from 135 to 237 and 245 μmole/(g of cat.) with the incorporation of 4.5 and 6 wt % Co, respectively, to the MWCNT-supported, alkali-promoted bimetallic Rh—Mo catalyst. This confirms that MWCNT-supported alkali-promoted Co—Rh—Mo trimetallic catalysts enhanced the CO hydrogenation capability, compared to that of MWCNT-supported alkali-promoted Rh—Mo bimetallic catalyst. A metal dispersion of 48% was observed on the alkali-promoted trimetallic catalyst with 4.5 wt % Co content that was supported on the MWCNTs. When the Co content was increased to 6 wt % on the MWCNT-supported, alkali-promoted trimetallic catalyst, the metal dispersion decreased to 45%, suggesting that high Co loading (6 wt %) leads to the formation of large particles. From XRD data, it is seen that amount of $Co_9S_8$ species is high at higher Co content (6 wt % Co) in Co—Mo—K/MWCNT catalysts. Higher Co loading decreases the surface area of the active Co—Mo—S phase (responsible for the formation of higher alcohols), resulting lower metal dispersion.[44] Metal dispersions of 28% and 26% were observed on the activated carbon supported alkali-promoted trimetallic catalysts containing 4.5 and 6 wt Co, respectively.

Figure 3:
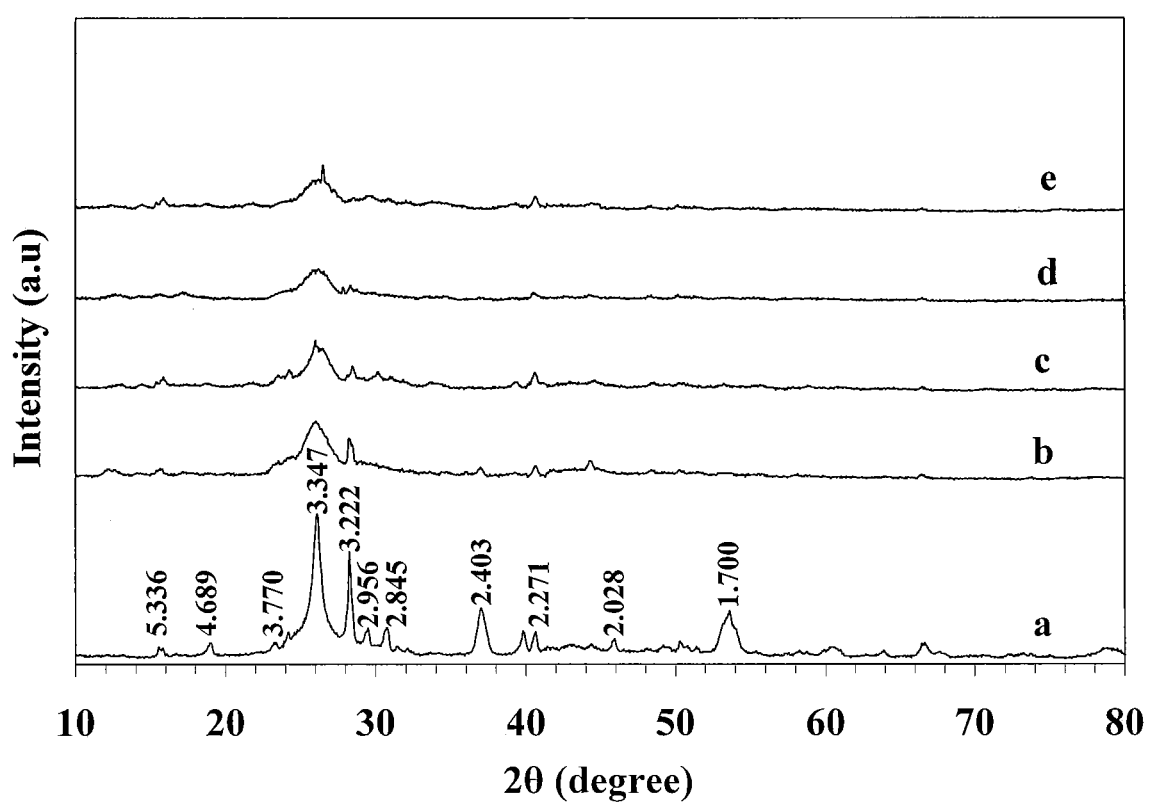
FIG. 3 shows XRD patterns of exemplary catalysts in oxidized form a. Rh—Mo—K/MWCNT; b. 4.5 wt % Co—Rh—Mo—K/MWCNT; c. 6 wt % Co—Rh—Mo—K/MWCNT; d. 4.5 wt % Co—Rh—Mo—K/AC; e. 6 wt % Co—Rh—Mo—K/AC.
Figure 4:
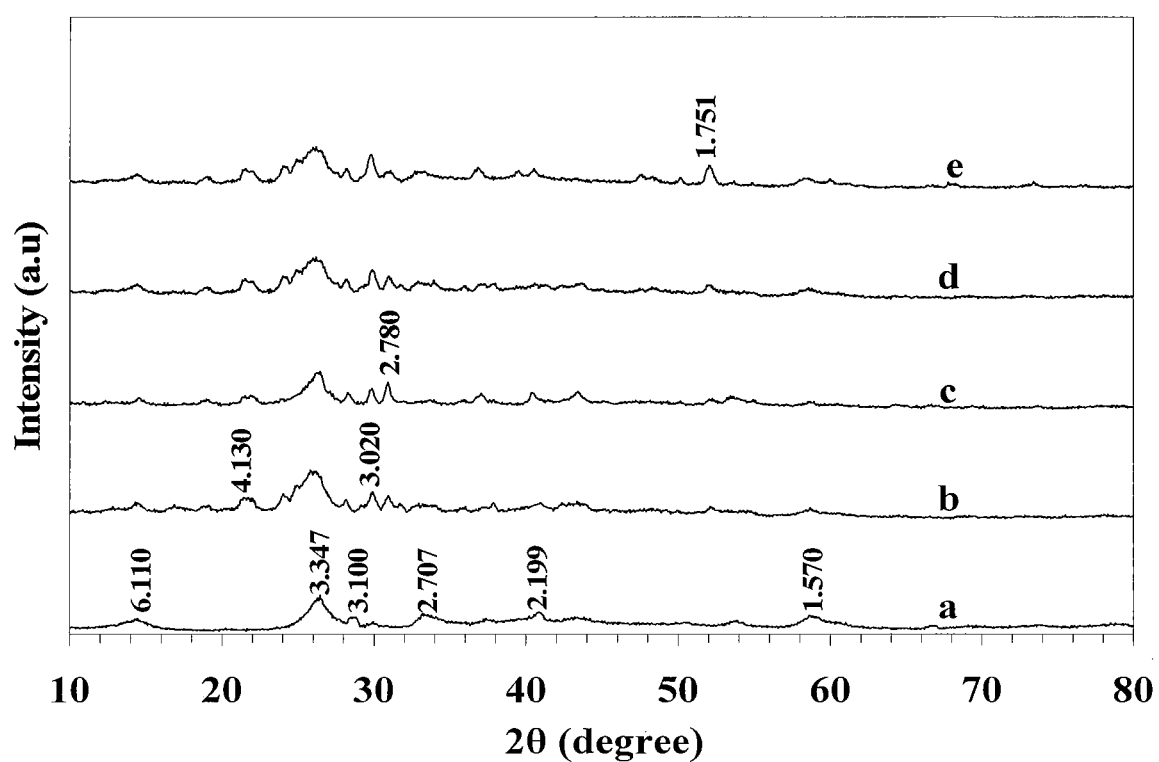
FIG. 4 shows XRD patterns of exemplary catalysts in sulfided form a. Rh—Mo—K/MWCNT; b. 4.5 wt % Co—Rh—Mo—K/MWCNT; c. 6 wt % Co—Rh—Mo—K/MWCNT; d. 4.5 wt % Co—Rh—Mo—K/AC; e. 6 wt % Co—Rh—Mo—K/AC.

The XRD patterns of the catalysts in oxidized and sulfided form were measured and shown in FIGS. 3 and 4, respectively. The JCPDS chemical spectra data bank was used to detect the most probable phases present in the samples, and the results of the possible crystal phases with their corresponding reflection planes are given in Table 2.

The strong intensity peaks at 2θ value of 26.6° are due to the reflections of the graphite phase present in the MWCNT and activated carbon supports.[41] The characteristic reflections corresponding to the crystalline structure of $MoO_3$ are observed at 2θ value of 40.2° 0.41. In the oxidized form of the MWCNT-supported alkali-promoted bimetallic Rh—Mo catalyst, K—Mo—O mixed phases exist in several forms. The peaks at 2θ values of 19.4°, 28.5°, 29.8°, and 30.9° correspond to the characteristic reflections of the $K_2Mo_2O_7$ phase.[45] Other K—Mo—O phases, such as $KMo_4O_6$ (2θ=16.0° and 37.1°) and $K_2Mo_7O_{20}$ (2θ=23.6° and 53.8°), also exist on this catalyst.[46,47] The diffraction intensity of the peaks was greatly reduced with the incorporation of Co, which confirms that adding the third metal to the alkali-promoted bimetallic Rh—Mo catalysts improved the dispersion of the metal species on the support.

The various diffraction peaks observed in the XRD patterns of oxide samples are completely removed after sulfidation, and new diffraction peaks representing different sulfide species appeared. The reflections of $MoS_2$ crystallites are observed at 2θ values of 14.6°, 33.4°, 40.9°, and 58.9° in the XRD pattern of the alkali-promoted MWCNT-supported, bimetallic Rh—Mo catalyst.[48] The peak intensity of the $MoS_2$ crystallites decreased with the addition of Co. The peaks at 2θ values of 21.5°, 28.4°, 29.9°, and 31.5° are due to the characteristic reflections of the K—Mo—S species and are related to active sites for higher alcohols synthesis.[49] The peak at 2θ values of 52.4° is due to the different reflecting planes characteristic of bulk $Co_9S_8$ particles.[35] The intensity of these peaks is high on the activated support, compared to that of MWCNTs.

Figure 5:
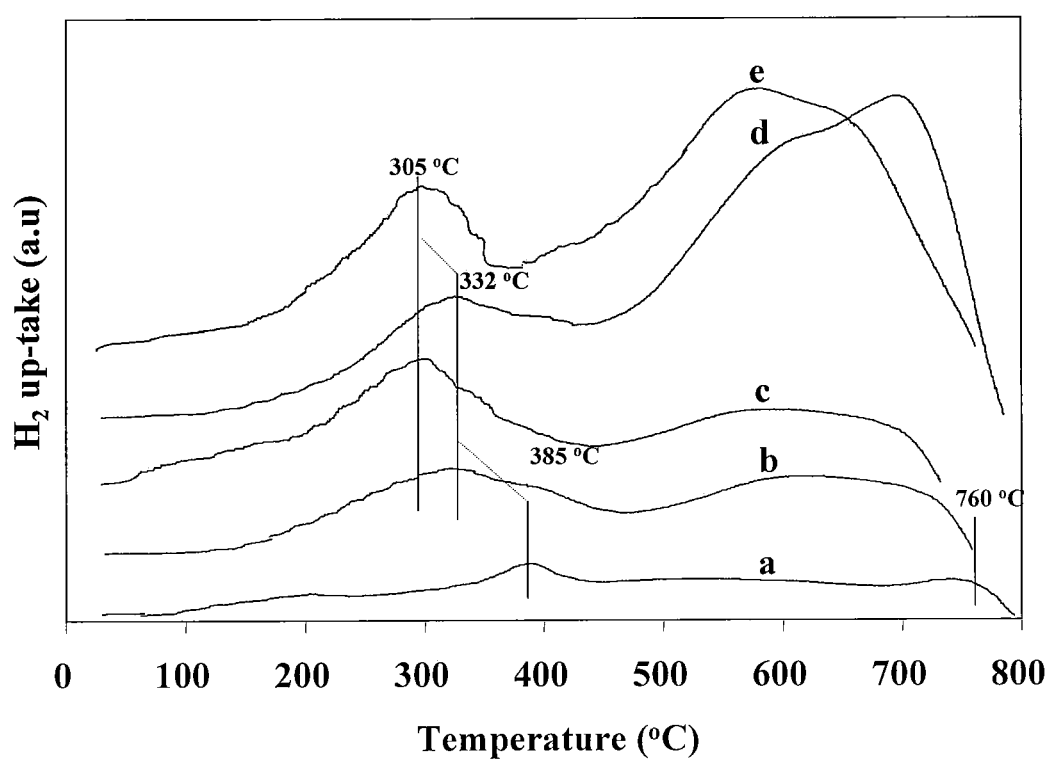
FIG. 5 shows $H_2$-TPR profiles of exemplary catalysts: a. Rh—Mo—K/MWCNT; b. 4.5 wt. % Co—Rh—Mo—K/MWCNT; c. 6 wt. % Co—Rh—Mo—K/MWCNT; d. 4.5 wt. % Co—Rh—Mo—K/AC; e. 6 wt. % Co—Rh—Mo—K/AC.

The $H_2$-TPR studies (FIG. 5) of all the catalysts reveal two reduction peaks, the low temperature reduction peak is attributed to the reduction of bulk $MoO_3$ and the high temperature peak is due to the complete reduction of $MoO_2$ to lower oxidation state.[50,51] The low temperature reduction peak at 385° C., and the second peak at 760° C. were observed in the $H_2$-TPR profile of MWCNT-supported alkali-promoted bimetallic Rh—Mo catalyst. With the incorporation of 4.5 wt % Co, the low temperature reduction peak shifted from 385-332° C. The high temperature reduction feature for the catalyst promoted with 4.5 wt % Co was observed in the temperature range of 570-740° C., which confirms that the addition of Co to the alkali-promoted bimetallic Rh—Mo catalyst enhances the metal species to reduce at low temperatures. The temperature peak attributed to the reduction of the octahedral coordinated Mo ($Mo^{6+}$) species to the tetrahedral coordinated Mo ($Mo^{4+}$) species was further shifted to 305° C., and the reduction of the $Mo^{4+}$ species to a lower oxidation state was observed in the temperature range of 500-700° C. on the MWCNT-supported alkali-promoted trimetallic Co—Rh—Mo catalyst with 6 wt % Co.

On the activated carbon-supported catalysts, similar results were observed, but with the ratio of high to low temperature peaks being greater than on the MWCNT-supported catalysts. In addition, some weak features occurred at higher temperature positions on the activated carbon-supported catalysts, indicating that more than one kind of oxidic Mo (VI) species existed on the support. These differences are attributed to the interaction of Mo (or Co) species with the activated carbon support.

(b) Higher Alcohols Synthesis

Figure 6:
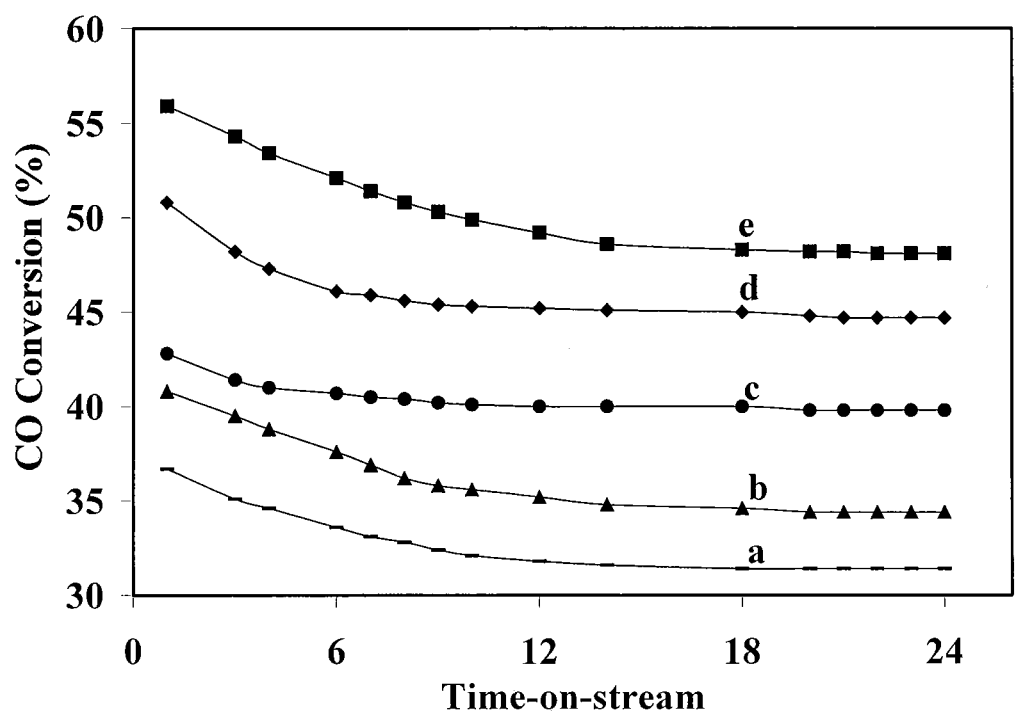
FIG. 6 is a graph showing % CO Conversion with time on stream for exemplary catalysts: a. Rh—Mo—K/MWCNT; b. 4.5 wt. % Co—Rh—Mo—K/MWCNT; c. 6 wt. % Co—Rh—Mo—K/MWCNT; d. 4.5 wt. % Co—Rh—Mo—K/AC; e. 6 wt. % Co—Rh—Mo—K/AC (wt. of the cat.=2 g, P=8.3 MPa, T=320° C., GHSV=3.6 m³ (STP)/(kg of cat.)/h, $H_2$/CO molar ratio=1).

The catalyst activity studies toward higher alcohol synthesis reaction were carried out under similar conditions at 320° C., 8.3 MPa (1200 psig), 3.6 $m^3$ (STP)/(kg of cat.)/h, and $H_2$ to CO molar ratio of 1. FIG. 6 gives the results of the percentage CO conversion as time-on-stream during higher alcohols synthesis reaction over the MWCNT-supported catalyst with 1.5 wt % Rh, 15 wt % Mo, and 9 wt % K, as well as the trimetallic catalysts promoted with varying loadings of Co (4.5 and 6 wt %) supported on MWCNTs and activated carbon. As FIG. 6 shows, during the 24-h alcohol synthesis, CO conversion was sharply reduced in the first 12 h, and then leveled off, indicating that the catalyst was quite stable after 12 h of time-on-stream. A 40% CO conversion was observed on the alkali-modified bimetallic Rh—Mo catalyst supported on MWCNTs. The alkali-promoted trimetallic catalysts with 6 wt % Co showed the highest CO conversion, compared to the catalyst with 4.5 wt % Co, which confirms that the activity for hydrogenation reaction improved with increased Co wt % in the catalyst. The 45 and 49% CO conversions were observed on the MWCNT-supported 1.5 wt % Rh, 15 wt % Mo, and 9 wt % K catalysts promoted with 4.5 and 6 wt % Co, respectively. The activated carbon-supported catalysts promoted with 4.5 and 6 wt % Co showed CO conversions of 31 and 35%, respectively. The catalytic activity and product selectivity data were calculated after an induction period of 15 h.

The analysis of the liquid products indicates that linear alcohols are formed and no branched alcohols were observed in the GC trace corresponding to the higher alcohols. Methanol, ethanol, n-propanol, and n-butanol are the major products, together with other higher alcohols. The analysis of exit gas indicates that methane is the major component apart from $CO_2$ and unconverted gases, such as, CO and $H_2$.

Table 3 shows the activity and selectivity results obtained from CO hydrogenation over the sulfided alkali-modified Co—Rh—Mo catalysts. The term higher alcohols represents the ethanol and alcohols with carbon numbers greater than 2 ($C_{2+}$ alcohols). Over the cobalt-free MWCNT-supported catalyst, the total alcohols and total hydrocarbons space time yields (STY) were 0.211 and 0.332 g/(g of cat.)/h, respectively. With the addition of 4.5 wt % Co on the MWCNT-supported 1.5 wt % Rh, 15 wt % Mo, and 9 wt % K catalyst, the total alcohols STY increased to 0.244 g/(g of cat.)/h and the total hydrocarbons STY decreased to 0.251 g/(g of cat.)/h. The methanol, ethanol, and higher alcohols selectivities increased from 5.4%, 16.0%, and 24.6% over the alkali-promoted bimetallic Rh—Mo/MWCNT catalyst to 6.7%, 20.1%, and 31.4% on the MWCNT-supported trimetallic catalyst promoted with 4.5 wt % Co. From the CO chemisorption results, it was observed that incorporation of 4.5 wt % Co to the alkali-modified bimetallic Rh—Mo catalyst supported on MWCNTs increased the CO uptake from 135 to 237 μmole/(g of cat.). Also, Co promotion to Rh—Mo—K/

MWCNT catalyst increased the metal dispersion from 39.5 to 49.8% favoring the formation of fine particles. These results, coupled with XRD data, confirm that incorporating Co metal increased the number of active sites responsible for the formation of alcohols. The water-gas shift reaction rate decreased significantly with the addition of Co. By increasing the Co loading from 4.5 to 6 wt % on the MWCNT-supported trimetallic catalyst, the total alcohols STY decreased from 0.244 to 0.235 g/(g of cat.)/h and total hydrocarbons STY increased from 0.251 to 0.293 g/(g of cat.)/h. With increased Co content from 4.5 to 6 wt %, the CO uptake increased from 237 to 245 μmole/(g of cat.), whereas the metal dispersion decreased from 47.8 to 44.8%. These results confirmed that the methanation activity of the catalyst is increased with increased Co content from 4.5 to 6 wt %, because of the formation of large size metal sulfide ($Co_9S_8$) sites. On the MWCNT-supported trimetallic catalyst promoted with 6 wt % Co, the selectivity of methanol, ethanol, and higher alcohols decreased to 5.9%, 18.5%, and 27.8%, respectively.

The activity and selectivity of the activated carbon catalysts toward higher alcohols synthesis are comparatively less than that of the catalysts supported on MWCNTs. This can be explained from the textural properties of the catalysts. The activated carbon-based catalysts showed a drastic fall in surface area and exhibited relatively low pore volume and diameter compared to the MWCNT-supported catalysts. The pore size of supported catalysts can influence particle size distribution, dispersion, extent of reduction, and directly affects mass transfer diffusion rates of reactants and products. MWCNT supports have the advantage of large pore volume and pore size that facilitates uniform metal particle distribution and high dispersions. The activated carbon-supported catalysts follow similar trends in STY of total alcohols and total hydrocarbons. The selectivity of methanol was higher than that of ethanol over the activated carbon-supported catalysts, confirming that the CO insertion mechanism, which promotes the chain growth probability for the formation of higher alcohols from methanol, is less effective compared to the catalysts supported on MWCNTs.

Figure 7:
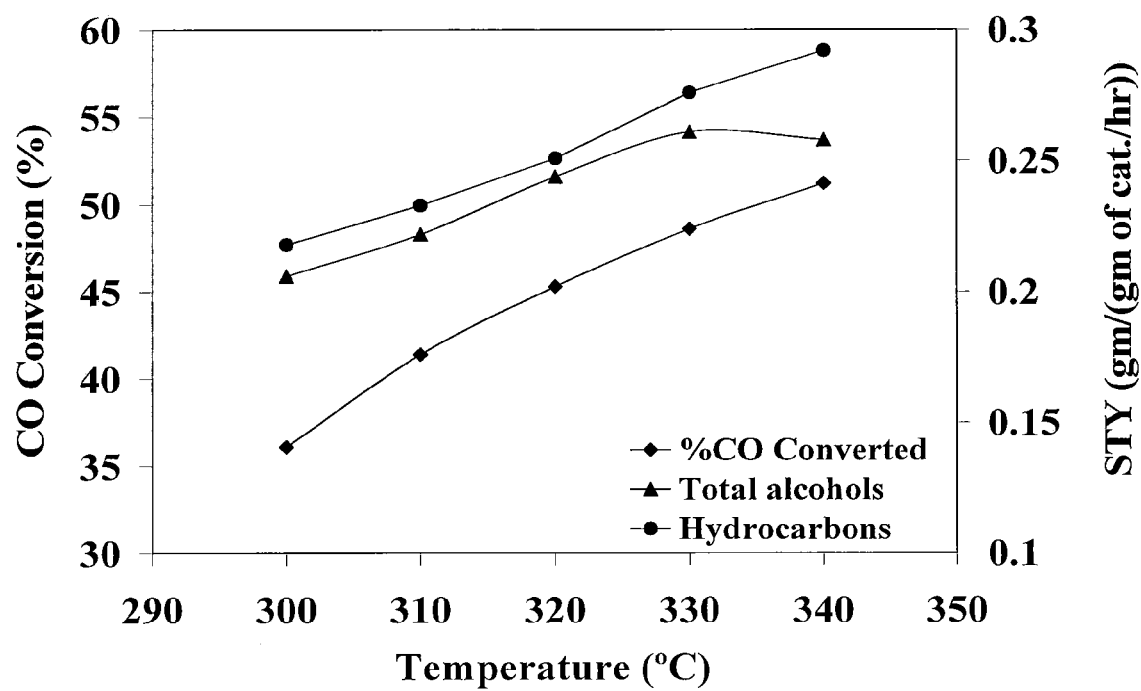
FIG. 7 is a graph showing the change of % CO conversion and STY of total alcohols and hydrocarbons with temperature for the exemplary MWCNT-supported alkali-modified trimetallic catalyst promoted with 4.5 wt % Co (wt. of the cat.=2 g, P=8.3 MPa, GHSV=3.6 m³ (STP)/(kg of cat.)/h, $H_2$ to CO molar ratio=1).
Figure 8:
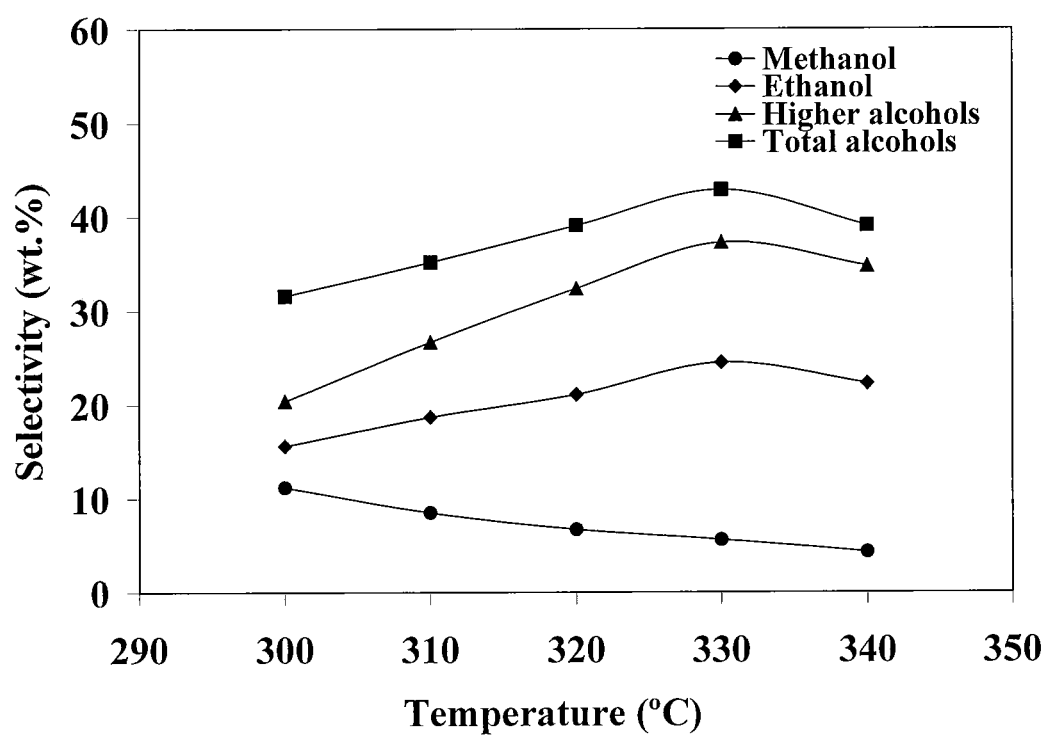
FIG. 8 is a graph showing the selectivities of methanol, ethanol, higher alcohols, and total alcohols with temperature for the exemplary MWCNT-supported alkali-modified trimetallic catalyst promoted with 4.5 wt % Co (wt. of the cat.=2 g, P=8.3 MPa, GHSV=3.6 m³ (STP)/(kg of cat.)/h, $H_2$ to CO molar ratio=1).

The MWCNT-supported alkali-modified trimetallic catalyst promoted with 4.5 wt % Co was used to study temperature effects on higher alcohols synthesis reactions. The reactions were performed under similar conditions at 8.3 MPa (1200 psig) and 3.6 $m^3$ (STP)/(g of cat.)/h. As shown in FIG. 7, the CO conversion and hydrocarbon STY increased monotonically from 36.1 to 51.2% and 0.218 to 0.292 g/(g of cat.)/h, respectively, with increasing temperature from 300 to 340° C. The maximum total alcohol STY of 0.261 g/(g of cat.)/h was observed at 330° C. The methanol selectivity decreased monotonically with increased temperature, whereas, the ethanol, higher alcohols, and total alcohols selectivity displayed a pronounced increase, reaching maxima of 24.5%, 37.3%, and 42.9% at 330° C. (FIG. 8).

Figure 9:
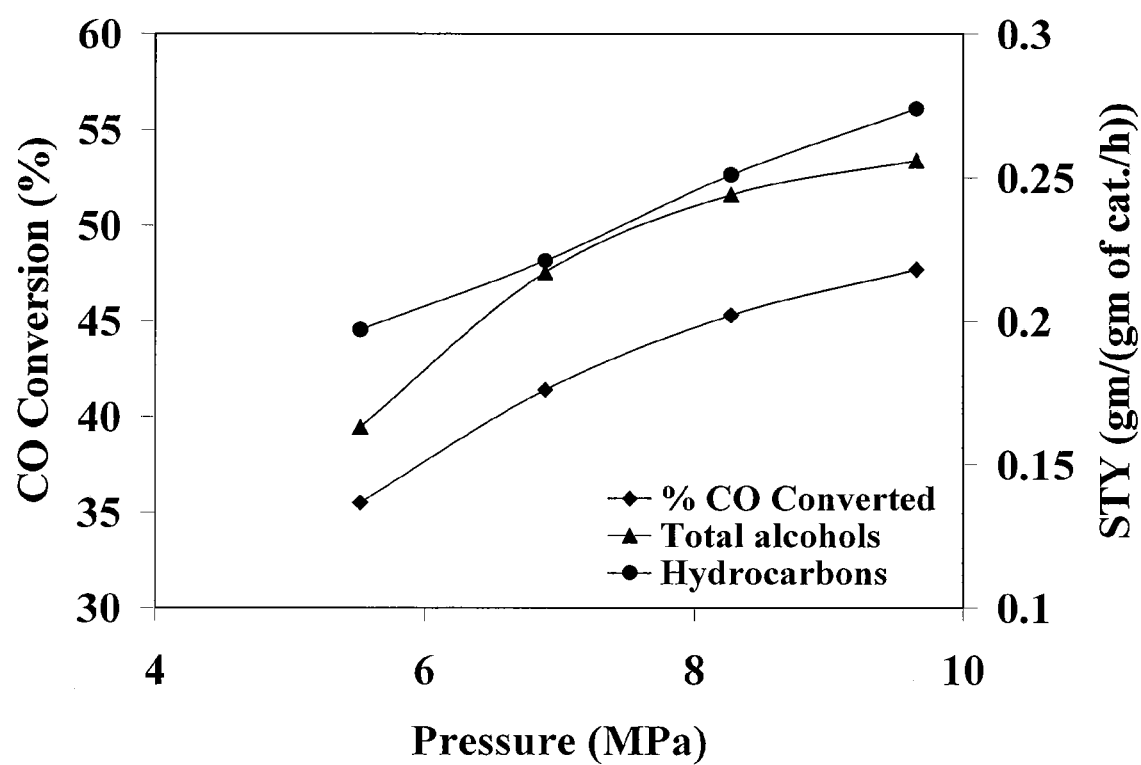
FIG. 9 is a graph showing the change of % CO conversion and STY of total alcohols and hydrocarbons with pressure for the exemplary MWCNT-supported alkali-modified trimetallic catalyst promoted with 4.5 wt % Co (wt. of the cat.=2 g, T=320° C., GHSV=3.6 m³ (STP)/(kg of cat.)/h, $H_2$ to CO molar ratio=1)
Figure 10:
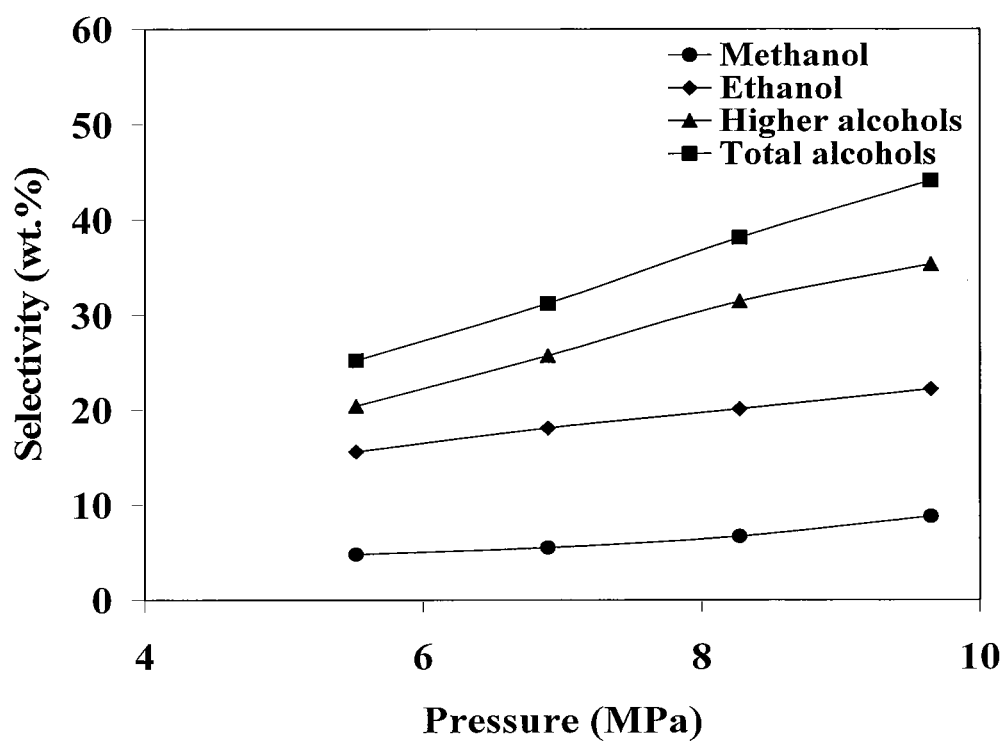
FIG. 10 is a graph showing the selectivities of methanol, ethanol, higher alcohols, and total alcohols with pressure for the exemplary MWCNT-supported alkali-modified trimetallic catalyst promoted with 4.5 wt % Co (wt. of the cat.=2 g, T=320° C., GHSV=3.6 m³ (STP)/(kg of cat./h), $H_2$ to CO molar ratio=1).

To investigate the effects of pressure, the reaction pressures were varied in the range of 5.5 to 9.7 MPa (800 to 1400 psig) over the MWCNT-supported, alkali-modified trimetallic catalyst promoted with 4.5 wt % Co at 320° C. and 3.6 $m^3$ (STP)/(g of cat.)/h. FIG. 9 shows that increased pressure monotonically increased the CO conversion, total alcohol formation rate, and hydrocarbon formation rate. The selectivity of methanol, ethanol, and higher alcohols also increased monotonically with increasing pressure, indicating that increasing pressure at a constant temperature favors the formation of higher alcohols (FIG. 10).

Table 4 compares the activities of sulfided 4.5 wt % Co, 1.5 wt % Rh, 15 wt % Mo, and 9 wt % K (catalyst D) supported on MWCNTs with those of other catalysts discussed in the literature. The catalyst with highest activity from each work was selected for comparison purposes. This table indicates that the sulfided alkali modified Co—Rh—Mo catalysts supported on MWCNTs produces 0.261 g/(g of cat./h) which is much higher than that reported in the literature.

Example 2

Alkali and Metal Promoters (Co and Rh) on $MoS_2$ Catalysts for Higher Alcohols Synthesis: Catalytic Performance and Structural Characterization Studies The role of alkali on the conversion of synthesis gas over $MoS_2$ catalysts to produce higher alcohols is not thoroughly understood. This example emphasizes the improved performance of $MoS_2$ catalysts due to the addition of alkali and metal promoters on modification of surface structure and oxidation states. This study revealed the formation of Co(Rh)—Mo—S species in the XANES spectra of bimetallic and trimetallic alkali-promoted $MoS_2$ catalysts, in agreement with the improved catalytic performance.

Materials and Methods
(a) Preparation of Catalysts

Commercially available MWCNTs and activated carbon were used as catalyst supports and the catalysts were prepared by conventional incipient wetness method, as described in Example 1. Ammonium heptamolybdate tetrahydrate (AHM), potassium carbonate, cobalt acetate tetrahydrate, and rhodium chloride hydrate were used as precursors for Mo, K, Co, and Rh, respectively.

(b) Catalyst Studies for Higher Alcohols Synthesis

The catalytic conversion of synthesis gas to higher alcohols was performed using the feed gas mixture CO (40 mole %), $H_2$ (50 mole %), and Ar (10 mole %) in a single-pass tubular downflow fixed-bed reactor under the reaction conditions of 330° C., 9.1 (1320 psig), and 3.8 $m^3$ (STP)/(kg of cat.)/h over a period of 24 h. The detailed description about the high pressure reaction set up used in this study was discussed in previous papers.[43,52,53,54] Prior to the reaction, the catalyst was reduced and sulfided for 6 h at 450° C. at a heating rate of 2° C./min using a gas mixture containing 10 mole % $H_2S$ in $H_2$ and a flow rate of 50 ml/min. The product gas was cooled to 0° C. and separated into gas and liquid phases at the reaction pressure. The liquid products were collected at the end of the reaction and analyzed with a Varian 3400 gas chromatograph equipped with a capillary column and a flame ionization detector (FID). The gaseous products were analyzed online on a Shimadzu gas chromatograph through a sampling valve for every 1 h. The experiments were repeated at least twice to check reproducibility and to confirm that the results obtained were within the experimental error of ±2.5%.

(c) Catalyst Characterization

The surface area, pore volume, and average pore diameter of the $MoS_2$ catalysts promoted with or without K, Co, and Rh-supported on MWCNT or activated carbon were measured by $N_2$-physisorption at 77 K using the methods described in Example 1.

Powder X-ray diffraction (XRD) analysis patterns of sulfide forms of samples were recorded on a Rigaku X-ray diffraction instrument as described in Example 1.

The S K-edge and Mo $L_3$-edge XANES of the sulfided catalysts were obtained at the Soft X-ray Microanalysis Beamline (SXRMB) of the Canadian Light Source (CLS; Saskatoon, SK, Canada) using a Si (111) double crystal monochromator. CLS, a 2.9 GeV, third generation storage ring, presently operates with an injection current of 250 mA. The sample was dispersed on double-sided conducting carbon tapes under a dry nitrogen atmosphere, and the measurements were made in both total electron yield by recording the sample drain current and fluorescence yield using a PGT single element Si(Li) drift detector. The XANES spectra were normalized to incident photon flux and to unity at the maximum intensity of each spectrum. Linear combination fitting of Mo $L_3$-edge spectra was performed using Athena software. The fitting was performed using the first derivative curves, and the weights of the components were set to be between 0 and 1 and the sum was forced to 1 during the fit.

Results and Discussion (a) Catalyst Studies for Higher Alcohols Synthesis

FIG. 11 shows the simplified reaction scheme of higher alcohols reaction from synthesis gas over alkali-modified $MoS_2$-based catalysts. According to this CO insertion mechanism,[55] CO hydrogenation takes place in three different steps: (a) chain initiation, (b) chain propagation, and (c) chain termination. In the first step, adsorption of CO takes place on the mixed K—Mo—S and M-Mo—S phases (M=transition metals such as Co, Ni, Fe, or Rh), while hydrogen adsorption occurs at the separated metal sulfide sites such as $MoS_x$ and $MS_x$, and these surface species react to form $R_1O_s$ ($R_1$—$CH_3$) intermediates. These species propagate chain growth through hydrogenation, followed by insertion of molecularly adsorbed $CO_s$ to form long chain intermediates $R_{is}$ ($R_i$—$C_nH_{2n+1}$, n=1, 2, 3, . . . ) and $R_{i+1}O_s$ ($R_{i+1}$—$C_{2n}H_{2n+1}$, n=1, 2, 3, . . . ). In the final step, direct hydrogenation of these intermediate hydrocarbon species leads to the formation of alkanes and alkenes, while methanol and higher alcohols are obtained from hydrogenation of the oxygenated hydrocarbon surface species ($R_1O_s$ and $R_{i+1}O_s$). This mechanism results in the formation of linear chain alcohols due to linear growth by $C_1$ intermediate insertion at the end of the chain that is bound to the surface.

Table 5 shows the activity and selectivity results obtained from the CO hydrogenation reaction carried out under similar conditions at 330° C., 9.1 MPa (1320 psig), 3.8 $m^3$ (STP)/(kg of cat.)/h, and $H_2$ to CO molar ratio of 1.25 over the sulfided Mo-based catalysts promoted with or without K, Co, and/or Rh. The analysis of the liquid products indicates that linear alcohols are formed and no branched alcohols were observed in the GC trace corresponding to the higher alcohols. The term higher alcohols represents ethanol and alcohols with a carbon number greater than 2 ($C_{2+}$ alcohols). Methanol, ethanol, n-propanol, and n-butanol are the major liquid products, together with other higher alcohols. The analysis of exit gas indicates that methane is the major component, apart from $CO_2$ and unconverted gases such as CO and $H_2$.

The % CO conversion increased with the addition of metal promoters, Co and Rh over the sulfided Mo—K/MWCNTs catalyst. Among the alkali-promoted MWCNTs catalysts, the trimetallic Co—Rh—Mo catalyst showed the highest CO conversion of 51.2%, confirming that CO hydrogenation is improved with the addition of metal promoters to the alkali-modified $MoS_2$ catalysts. Improved CO hydrogenation (% CO conversion 64.8%) is observed over the MWCNT-supported trimetallic catalyst without K. A lower CO conversion of 35.6% was observed on the alkali-promoted trimetallic catalyst supported on activated carbon, indicating that the CO hydrogenation activity was comparatively higher on catalysts supported on MWCNTs. The lower performance of activated carbon supported catalysts can be explained due to the microporous nature of the support, resulting lower dispersions of metal species.[54]

The total alcohols and total hydrocarbons space time yields (STY) of 0.12 and 0.19 g/(g of cat./h), respectively, were observed over the sulfided Mo—K/MWCNTs catalyst. The addition of Co and Rh to the Mo—K/MWCNTs catalyst in sulfided form increased the total alcohols STY to 0.26 and 0.26 g/(g of cat.)/h, respectively, and the total hydrocarbons STY to 0.39 and 0.36 g/(g of cat.)/h, respectively.

The alkali-promoted trimetallic Co—Rh—Mo catalyst supported on MWCNTs showed an improved total alcohol STY of 0.29 g/(g of cat.)/h, whereas the total hydrocarbon STY decreased, compared to that of alkali-promoted bimetallic catalysts. The decreased methanol selectivities and increased selectivities of ethanol and higher alcohols were observed on the bimetallic alkali-promoted catalysts supported on MWCNTs compared to that of monometallic catalyst. The highest ethanol and higher alcohols selectivities of 25.7 and 39.4% are observed on the trimetallic catalyst promoted with alkali and supported on MWCNTs.

The alkali-promoted trimetallic catalyst supported on activated carbon showed a total alcohols and total hydrocarbons STY of 0.19 and 0.22 g/(g of cat.)/h, respectively. The alkali-promoted trimetallic catalyst supported on activated carbon showed the highest selectivity towards methanol, compared to that of ethanol and other higher alcohols. This confirms that the chain growth mechanism that promotes the formation of higher alcohols is less effective on activated carbon supported catalysts compared to the catalysts with MWCNTs support.

(b) Catalyst Characterization

Textural Characteristics

The textural characteristics of all the catalysts are shown in Table 6. The surface area and pore volume of all the catalysts were decreased compared with that of the support due to the pore blocking and surface smoothing by the deposition of metals in sulfide state on the support. The BET surface area of Mo—K/MWCNT catalyst was found to be 109 $m^2$/g. With the incorporation of Co and Rh to the Mo—K/MWCNT catalyst, the surface area was decreased to 89 and 86 $m^2$/g, respectively. The alkali-promoted trimetallic Co—Rh—Mo/MWCNT catalyst showed a BET surface area of 79 $m^2$/g, whereas the trimetallic catalyst not promoted with K showed a BET surface of 68 $m^2$/g. These results suggest that alkali helped to disperse the metal species on the support, favouring the formation of small particles. A drastic fall in surface area over the activated carbon-supported catalysts was observed.

Activated carbon is a microporous support and has relatively low pore volume and pore size compared to that of MWCNTs, which are mesoporous in nature. The particle size distribution, dispersion, and extent of reduction depend on the pore size of supported catalysts and directly affect mass transfer diffusion rates of reactants and products. MWCNT supports have the advantage of large pore volume and pore size, which facilitate uniform metal particle distribution and high dispersions products.[56]

(c) X-Ray Diffraction

Figure 12:
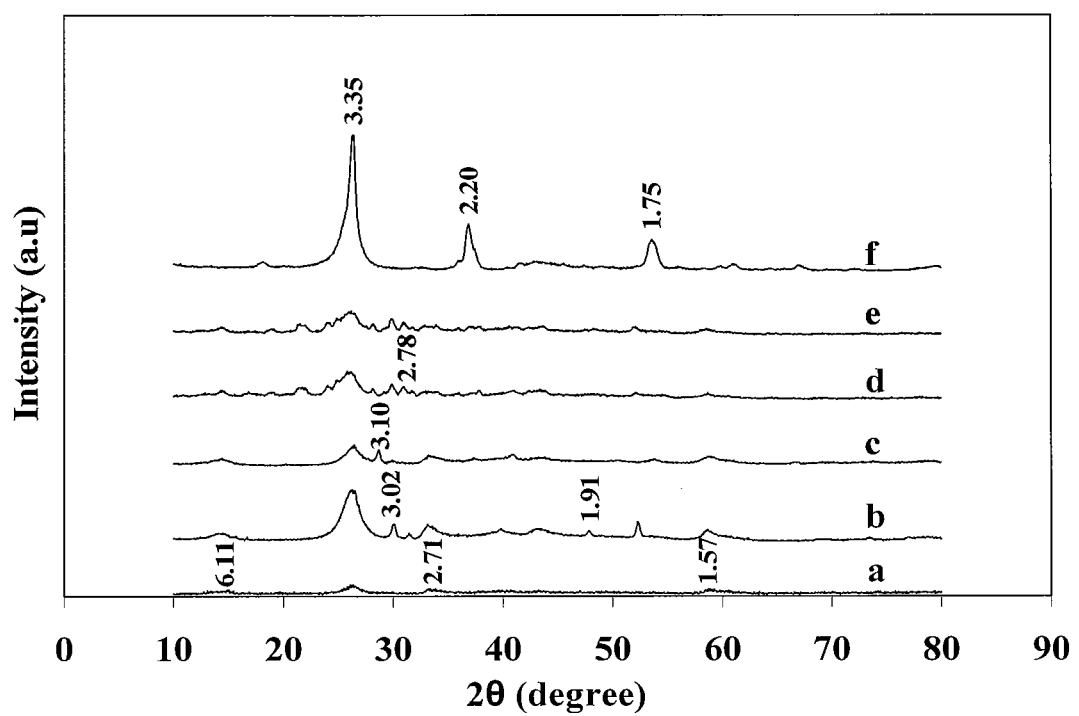
FIG. 12 shows XRD patterns of exemplary catalysts in sulfide form a. Mo—K/MWCNT; b. Co—Mo—K/MWCNT; c. Rh—Mo—K/MWCNT; d. Co—Rh—Mo—K/MWCNT; e. Co—Rh—Mo—K/MWCNT.

The XRD patterns of the catalysts in sulfided form were measured and are shown in FIG. 12. The JCPDS chemical spectra data bank was used to detect the most probable phases present in the samples, and the results of the possible crystal phases with their corresponding reflection planes are given in Table 7. The intense peaks at d-spacing of 3.35 are due to the reflections of the graphite phase present in the MWCNT and activated carbon supports.[57] The reflections of $MoS_2$ crystallites are observed at d-spacing values of 6.11, 2.71, and 1.57 (FIG. 12 (a)).[58] With the addition of metal promoters, Co and Rh, new peaks, such as at d-spacing of 3.02 and 1.75, can be observed, suggesting the formation of the new phases, Co(Rh)—Mo—S. These new phases are related to the electron donation from Co(Rh) to Mo. The formation of Co(Rh)—Mo—S decreases the Mo—S bond strength to an optimum range and significantly increases the activity of the catalyst towards the formation of higher alcohols.

The peaks at d-spacing of 3.1, 3.02, and 2.78 are observed on all the catalysts promoted with K. These are due to the characteristic reflections of the K—Mo—S species, and are related to active sites for higher alcohols synthesis.[59] The peak at d-spacing of 1.75 is due to the different reflecting planes characteristic of bulk $Co_9S_8$ particles.[60] The XRD patterns of the Co—Rh—Mo trimetallic catalyst without the alkali promoter mainly revealed three peaks due to the characteristic reflections of graphite carbon, $MoS_2$, and $Co_9S_8$ species. The intensity of these crystalline peaks is found to be large compared to the alkali-promoted catalyst, suggesting that alkali reduces the crystalline nature of the catalyst particles and favours the formation of smaller particles.

(d) XANES: Overview

Figure 13:
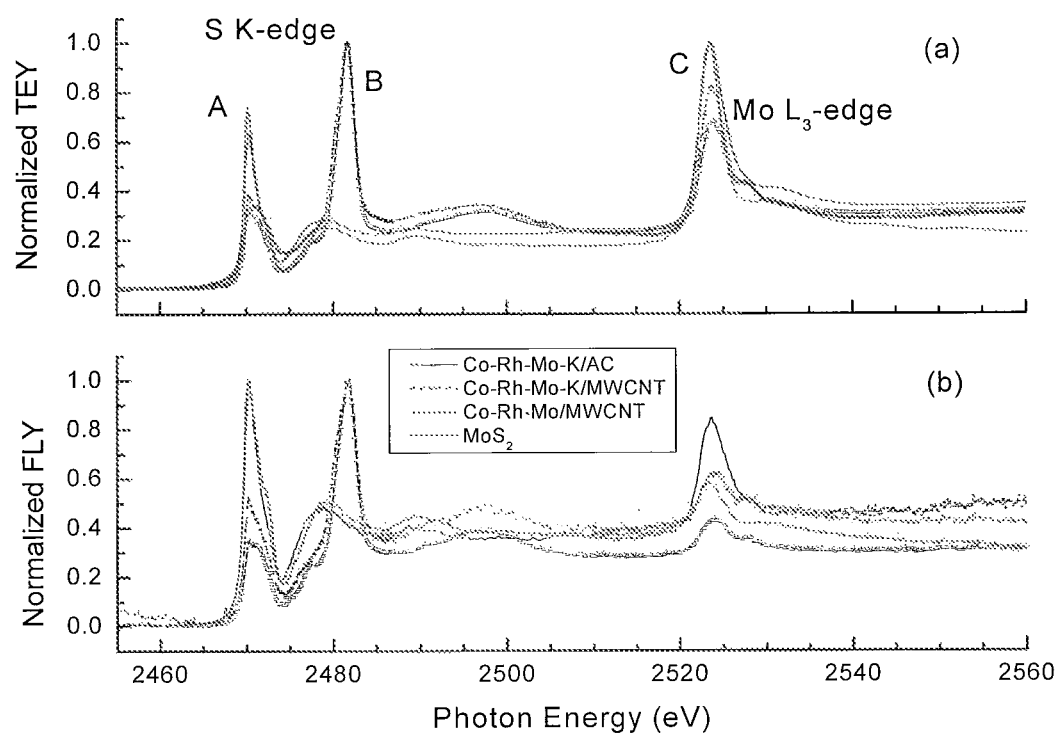
FIG. 13 shows an overview of S K-edge and Mo $L_3$-edge XANES spectra of various exemplary catalysts.

FIG. 13 shows the S K-edge and Mo $L_3$-edge XANES spectra of $MoS_2$ and three trimetallic $MoS_2$ catalysts. The total electron yield (TEY) is more surface sensitive, with an estimated probing depth of 100 nm at the S K-edge (FIG. 13(a)); while the fluorescence yield (FLY) is more bulk sensitive, with a probing depth about 10 times deeper than that of TEY (FIG. 13(b)). The TEY and FLY spectra for these samples are essentially identical in peak energy positions, but quite different in relative peak intensities. These spectra can be divided into three general regions: region A, around 2471 eV, is due to the S 1s to 3p dominated transitions of S in −2 oxidation state, such as $MoS_2$; region B appearing at 2481 eV is associated with the presence of oxidized sulfate ($SO_4^{-2}$) species; and region C around 2524 eV is assigned to absorptions as a result of transitions from Mo $2p_{3/2}$ initial state to empty orbitals with mainly Mo 4d characters. Compared to the sulfide peak (A), the relative intensities of peaks B and C are higher in the TEY spectra, indicating a more oxidized surface (FIG. 13(a) vs FIG. 13(b)). It is worth noting that the sulfate peak (B) is more pronounced in the K-promoted trimetallic systems, while there is little or no sulfate observed in spectra of the $MoS_2$ and of the catalyst without K. This is consistent with the XRD observation that only diffraction patterns due to $MoS_2$ and $Co_9S_8$ are present in the trimetallic catalyst without the alkali promoter (FIG. 12). The formation of sulfate species in the K-promoted $MoS_2$ catalysts is due to the oxidation of sulfur in the presence of oxygen of the molybdates.[61]

Zubavichus et al.[62] explained that the oxidation of $MoS_2$ takes place at surface-situated active centers located in the non-intercalated amorphous outer region of the particles. This partial oxidation of the sample is in agreement with the previous observation of S oxidation during synthesis and/or ageing by Guay et al.[63] S oxidation with Mo atom is also evident in the Mo $L_3$-edge results, as a shoulder peak at 2527.7 eV, due to the oxidized Mo, can be observed in the spectra of K-promoted catalysts. The alkali promotion leads to the formation of new phases, such as K—Mo—S, thus decreasing the number of available Mo sites. These results indicate that alkali promotion increased the susceptibility of $MoS_2$ layers to oxidation, thus improving the catalytic performance for higher alcohols yield. On the other hand, the trimetallic system without K promotion has very high (little) hydrocarbon (alcohol) conversion yield (Table 5). Its S K-edge spectrum is similar to that of $MoS_2$, confirming the importance of role of oxidation of $MoS_2$ in production of high alcohols. The peak intensities of sulfide and Mo of the catalyst supported on MWCNTs are found to be higher than those of the activated carbon, consistent with the higher catalytic performance observed for catalysts supported on MWCNTs (Table 5).

(e) XANES: the S K-Edge

Figure 14:
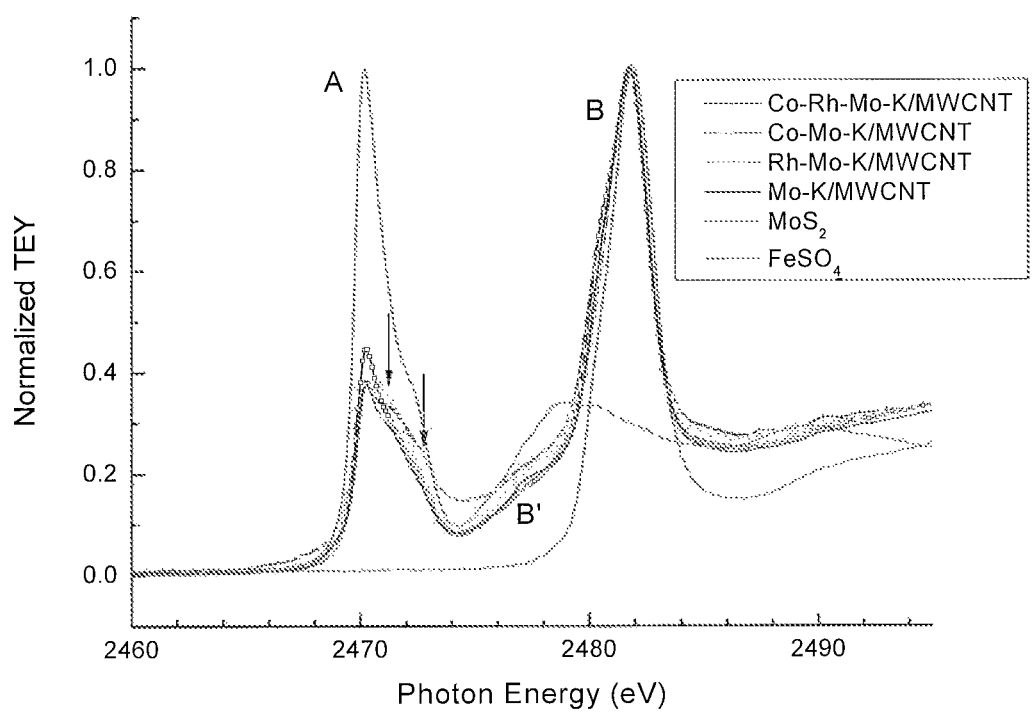
FIG. 14 shows S K-edge XANES spectra of exemplary K-modified $MoS_2$ catalysts.

The S K-edge XANES spectra of sulfur standards ($MoS_2$ and $FeSO_4$) and the MWCNT-supported alkali-promoted $MoS_2$ catalysts promoted with or without Co and Rh recorded in TEY are displayed in FIG. 14. Compared to the spectra of sulfur standards, it is clear that both sulfide and sulfate species are present in all alkali-promoted catalysts. The broadening of peak A for alkali-modified $MoS_2$-based catalysts, in particular the additional shoulder in peak A of the Co—Rh—Mo—K/MWCNT sample, providing further evidence of the formation of Co(Rh)—Mo—S networks in the Co and Rh-promoted catalysts. Peak B of the alkali-promoted catalysts is broader with additional intensity at the lower energy side, compared to that of $FeSO_4$. This is likely due to the formation of sulfate of a mixed nature (K—Mo—S, Co—Mo—S or Rh—Mo—S) in bimetallic and trimetallic catalysts and the chemical shift is due to stronger bonding between Fe and sulfate over the bonding between Mo (and/or Co, Rh) and sulfate. Finally, an additional shoulder around 2477 eV (peak B) can be observed in the spectra of alkali-promoted catalysts, a feature usually associated with intermediate sulfur species with an oxidation state of +4 or +2.[64] These results indicate that the formation of new phases (K—Mo—S, Co—Mo—S, and/or Rh—Mo—S) takes place with the addition of promoters, decreasing the crystalline nature of $MoS_2$ species, which correlates well with the catalytic performance shown in Table 5.

(f) XANES: Mo $L_3$-Edge

Figure 15:
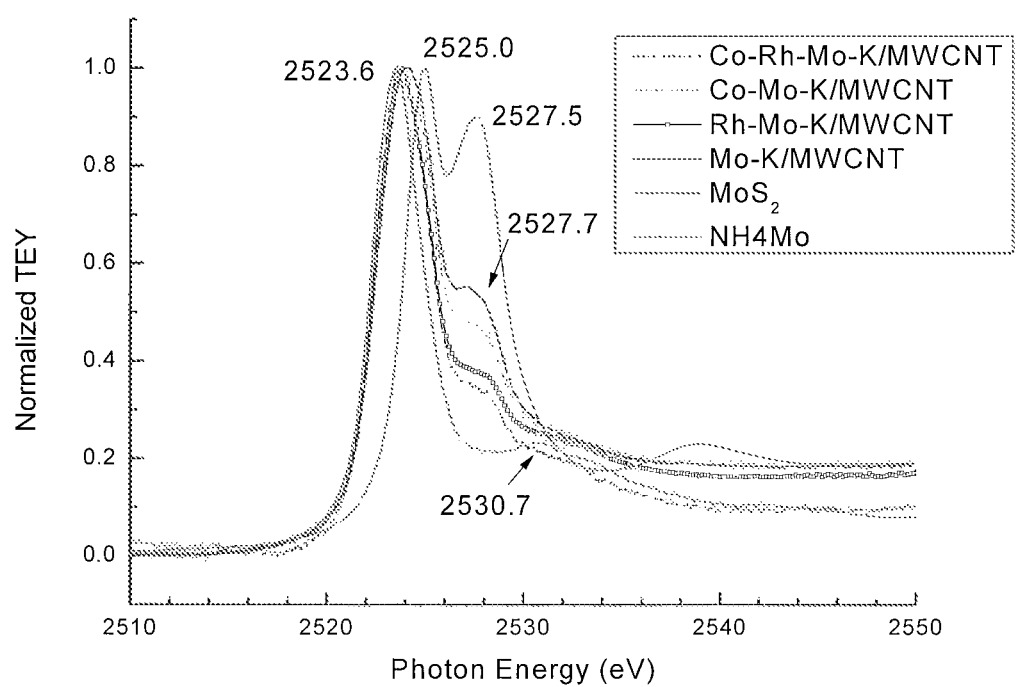
FIG. 15 shows Mo $L_3$-edge XANES spectra of exemplary K-modified $MoS_2$ catalysts.

The Mo $L_3$-edge XANES of reference compounds, $MoS_2$ (Mo oxidation state +4) and ammonium hepta molybdate (AHM) (Mo oxidation state +6), and the MWCNT-supported alkali-promoted $MoS_2$ catalysts, recorded in TEY-mode spectra are given in FIG. 15. The Mo $L_3$-edge of $MoS_2$ was observed at 2523.6 eV with a shoulder peak at 2530.7 eV due to the tetrahedral coordination of Mo atoms.[65] The Mo $L_3$-edge XANES spectrum of ammonium hepta molybdate (AHM) displayed a characteristic doublet at 2525.0 and 2527.5 eV, as a result of the ligand field splitting of the d final states under octahedral symmetry.[63] The Mo $L_3$-edge spectra of the MWCNT-supported alkali-promoted bimetallic or trimetallic catalysts shown in FIG. 15 are somewhat different from those of the Mo model compounds. The main peak is at a very similar energy position (2524.0 eV) to that of $MoS_2$, suggesting that presence of $MoS_2$ in these catalysts. The broadening of the main peak and the presence of the second peak at 2527.7 eV that overlaps the doublet of the AHM spectrum, strongly suggest the oxidation of Mo in these catalysts with the addition of Co and Rh. The intensity of 2527.5 eV peak follows the order of Co—Rh—Mo—K/MWCNT>Co—Mo-/MWCNT>R$_H$-M$_O$—K/MWCNT>Mo—K/MWCNT.

Figure 16:
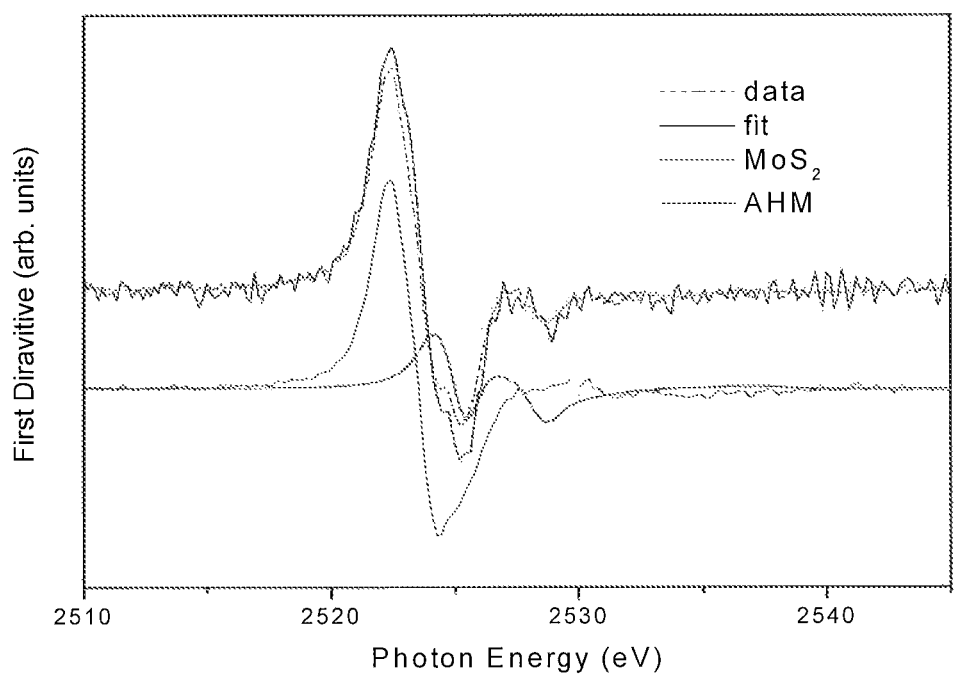
FIG. 16 shows linear combination fitting of the Mo $L_3$-edge spectra of the exemplary catalyst Mo—K/MWCNT FIG. 17 $N_2$ adsorption-desorption isotherms of exemplary pure supports a. AC-Darco; b. AC-$RX_3$ extra; c. AC-Fluid coke; d. AC-CGP super; e. MWCNT.
Figure 17:
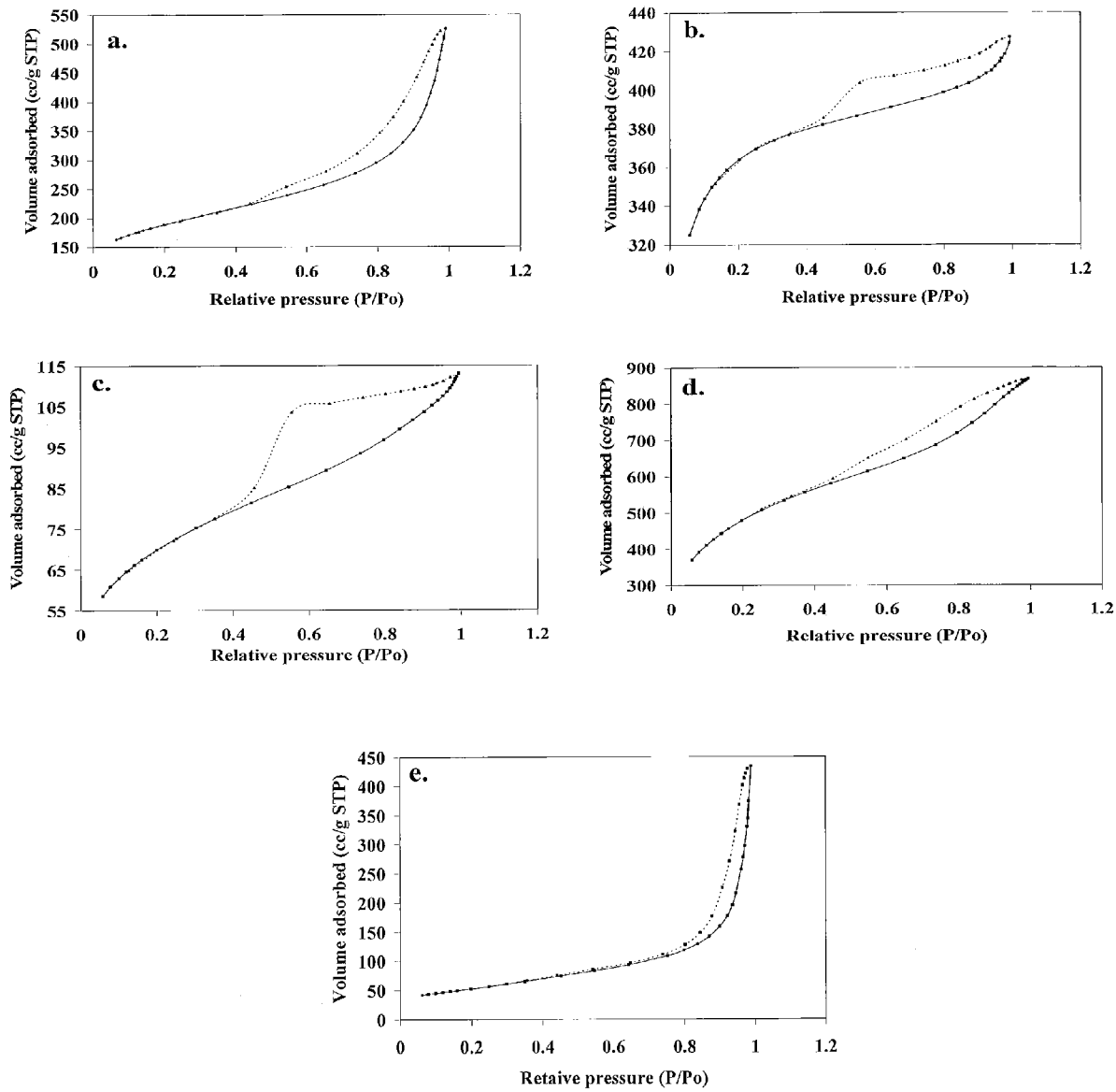

FIG. 16 presents the linear combination fitting of the Mo $L_3$-edge spectra of the catalyst Mo—K/MWCNTs. Spectra of $MoS_2$ and AHM are used as standards in the fitting. Based on the fitting, the oxidized $Mo^{+6}$ species is estimated to be 19.2%, 11.5%, and 0.4% for the Mo—K/MWCNT, Co—Rh—Mo—K/MWCNT, and Co—Rh—Mo/MWCNT catalysts, respectively. In trimetallic catalysts without K, the Mo species mainly exist as $MoS_2$ state, whereas the addition of K favours the oxidation of $Mo^{+4}$ to $Mo^{+6}$ states. The addition of transition metal promoters (Co and Rh) to the Mo—K catalyst leads to the formation of Co—Mo—S phase, in which Mo exits mainly in +5 oxidation state, which is the active phase for the formation of higher alcohols.[66] The decreased amount of $Mo^{+6}$ species due to the promotion of Co and Rh to the Mo—K catalyst suggests the reduction of Mo from +6 to +5 oxidation state.

The trimetallic catalyst without K showed improved activity towards the formation of hydrocarbons and very little activity for the alcohols synthesis reaction. From the results of XRD and XANES, it was observed that the intensity of the metal sulfide peaks is large (no sulfate intensity) and the BET surface area is less on the trimetallic catalyst that is not promoted with K, compared to that of alkali-promoted trimetallic catalyst. The results in the present study implied that the addition of K is beneficial to the dispersion of large metal sulfide agglomerates to small particles on the support by favouring the formation of chemically combined new phases (Co(Rh)—Mo—S) in sulfide state. This suggests that the promotion of alkali reduces the hydrogenation ability of alkyl species to form alkanes and increases the active sites for the formation of alcohols.

(g) Conclusions

The addition of Co and Rh, to the sulfided Mo—K/MWCNT catalyst improved the space time yield and selectivity of the higher alcohols. The maximum total alcohols yield of 0.29 (g/(g of cat./h)) and higher alcohols selectivity of 39.4% were obtained over the Co—Rh—Mo—K/MWCNT catalyst at 330° C., 1320 psig (9.1 Mpa), 3.8 m$^3$ (STP)/(kg of cat.)/h using H$_2$ to CO molar ratio value of 1.25. The AC-supported Co—Rh—Mo—K catalyst had a much higher hydrocarbon formation, while the MWCNT-supported alkali-promoted trimetallic catalyst showed better alcohols yield. Alkali promotion to the MoS$_2$ catalyst reduced the crystalline nature of the catalyst and favored the formation of alcohols. More oxidized S and Mo species were also observed by XRD and XANES in the K-promoted catalysts, indicating the formation of more Mo oxide and/or Co oxide with the addition of K, thus increasing the active sites. More intense features corresponding to the oxidized S and Mo species were observed in both S K-edge and Mo L$_3$-edge spectra of the MWCNT-supported catalysts. The formation of Co(Rh)—Mo—S species was evident in the XANES spectra of the bimetallic and trimetallic alkali-promoted MoS$_2$ catalysts, in agreement with their improved catalytic performance.

Example 3

Influence of Porous Characteristics of the Carbon Support on Alkali-Modified Trimetallic Co—Rh—Mo Sulfided Catalysts Materials and Methods
(a) Catalyst Preparation Four catalysts listed in Table 8 were prepared using different activated carbons. AC-Darco, brand named activated carbon was purchased from Aldrich, Canada. Two activated carbons, brand named as AC-RX$_3$ extra and AC-CGP super were obtained form Norit, USA. Activated carbon named as AC-Fluid coke is obtained from Syncrude and activated in our pilot scale reactor. Commercial MWCNTs were purchased from M. K. Nano, Canada. Prior to impregnation, all the supports were treated with 30% HNO$_3$ reflux at 100° C. overnight, washed with distilled water several times, and dried at 120° C. for 6 h. The oxide samples were prepared by the incipient wetness impregnation method using ammonium heptamolybdate tetrahydrate (Sigma-Aldrich, Canada), potassium carbonate (Aldrich, Canada), cobalt acetate tetrahydrate (Alfa-Aesar, Germany), and rhodium chloride hydrate (Aldrich, Canada) as precursors for Mo, K, Co, and Rh, respectively. At the first step, the support was impregnated with an aqueous solution of K$_2$CO$_3$, followed by drying at 120° C. for 2 h and stabilizing in an argon flow of 50 ml/min at 300° C., at a heating rate of 10° C./min for 4 h. The support was further impregnated with aqueous solutions containing the required amounts of (NH$_4$)$_6$Mo$_7$O$_{24}$, Co(CH$_3$COO)$_2$, and RhCl$_3$ followed by drying at 120° C. for 2 h and stabilizing in an argon flow of 50 ml/min at 450° C., at a heating rate of 10° C./min for 12 h.

(b) Characterization of Co—Rh—Mo—K Catalysts

The surface area, pore volume, and average pore diameter of oxide samples were measured by N$_2$-physisorption at 77 K using the method described in Example 1.

The content of Mo, Co, and Rh of the oxide catalysts was determined as described in Example 1.

Powder X-ray diffraction (XRD) analysis patterns of oxide forms of samples were recorded on a Rigaku X-ray diffraction instrument as described in Example 1.

Carbon monoxide was used as a probe molecule to determine the number of accessible surface metal atoms present on the sulfided catalysts as described in Example 1.

The morphology of the oxide samples was characterized by transmission electron microscopy (TEM) investigations as described in Example 1.

(c) Catalyst Activity and Selectivity Studies

A single-pass tubular downflow fixed-bed reactor of 450-mm length and 22-mm inside diameter made of inconel tube was used to perform higher alcohol synthesis reactions. The reactor was packed with 2 g of catalyst diluted with 12 ml of 90 mesh size silicon carbide and housed in an electric furnace controlled by a temperature controller. The reactor was pressurized with He to 3.44 MPa (500 psig) and the sulfidation, together with the reduction, was carried out for 6 h at 450° C. at a heating rate of 2° C./min using a gas mixture containing 10 mole % H$_2$S in H$_2$ and a flow rate of 50 ml/min. The temperature was then lowered to the reaction temperature, and the system pressurized to the reaction conditions. The feed gas mixture CO (30 mole %), H$_2$ (60 mole %), and Ar (10 mole %) was passed through mass flow controllers and the higher alcohols synthesis reaction was carried out at steady-state under the reaction conditions of 330° C., 8.27 (1200 psig) and a gas hourly space velocity (GHSV) of 3.6 m$^3$ (STP)/(kg of cat.)/h over a period of 24 h. The product gas was cooled to 0° C. and separated into gas and liquid phases at the reaction pressure. The CO conversion and other gaseous products were monitored with a time interval of 1 h. The liquid products were collected at the end of the reaction and analyzed with a Varian 3400 gas chromatograph equipped with a capillary column and a flame ionization detector (FID). The volume and weight of liquid products were measured to check the mass balance. The gaseous products were analyzed online on a Shimadzu gas chromatograph through a sampling valve. Using Ar as an internal standard, the CO conversion was calculated and the overall mass balance of the reaction was determined. The experiments were repeated at least twice to check reproducibility and to confirm that the results obtained were within the experimental error of ±2.5%.

Results and Discussion
(a) Characterization of Co—Rh—Mo—K Catalysts

The N$_2$ adsorption-desorption isotherm of all the supports were measured with an aim to measure the total surface area and are shown in FIGS. 17a to 17e. The microporous activated carbon support, AC-Darco, exhibits a type III isotherm with a hysteresis loop of type H$_2$ according to the IUPAC classification.[67] Type II adsorption isotherm with a hysteresis loop of type H$_2$ is observed on the support, AC-Rx$_3$ extra.[68] A horizontal plateau at relative higher pressures indicates highly microporous nature of this support with a narrow pore size distribution. On the support, AC-Fluid coke, the increment of N$_2$ uptake was significant at high relative pressures and showed type IV isotherm with a hysteresis loop of type H$_3$ that does not exhibit any limiting adsorbtion at high relative pressures.[67] This indicates the presence of large amount of mesopores on this support. The $N_2$ adsorption-desorption characteristic type IV isotherm with large condensation of adsorbate in pores at mesoporous regions (x=p/p$_s$≥0.40) was observed on the mesoporous support, AC-CGP super.[67] The MWCNT support showed the characteristic type IV isotherm with $H_1$ hysteresis loop, indicative of the existence of textural mesopores with cylindrical arrays of pore channels. The sharpness of the desorption branches suggests the narrow pore size distribution of the MWCNT support.[69] FIGS. 18a to 18e displays the $N_2$ adsorption-desorption isotherms of all the catalysts. From these figures, it is cleat that the amount of $N_2$ adsorbed on the support is proportional to the available surface area. All the catalysts exhibit similar isotherms as their corresponding supports, suggesting that metal impregnation did not alter the structure of the parent support.

The results for textural characterization of supports as well as the catalysts are summarized in Table 8. Data are tabulated for BET surface area ($S_{BET}$), mesopore surface area ($S_{me}$), total pore volume ($V_{tot}$), mesoporous volume ($V_{me}$), average pore diameter (D), and the percentage of mesoporosity (% Me), defined as percentage ratio of mesopore due to metal loading was calculated using BE=1−NS$_{BET}$, where NS$_{BET}$ is the normalized surface area, and is defined as $NS_{BET}= (S_{BET})_{catalyst}/((1-y)*(S_{BET})_{support})$, in which y is the weight fraction of the total metal content of the catalyst.[70] It is observed from the table that the support, AC-Fluid coke has low surface area and pore volume among the activated carbon supports. The support, AC-CGP super displays the highest BET surface area, total pore volume and mesoporous volume. MWCNTs exhibit low surface area compared to that of activated carbon supports, whereas, the pore diameter is found to be quite high. The supports AC-CGP super and MWCNTs are highly mesoporous in nature with mesoporosity of 94 and 98%, respectively.

Figure 18:
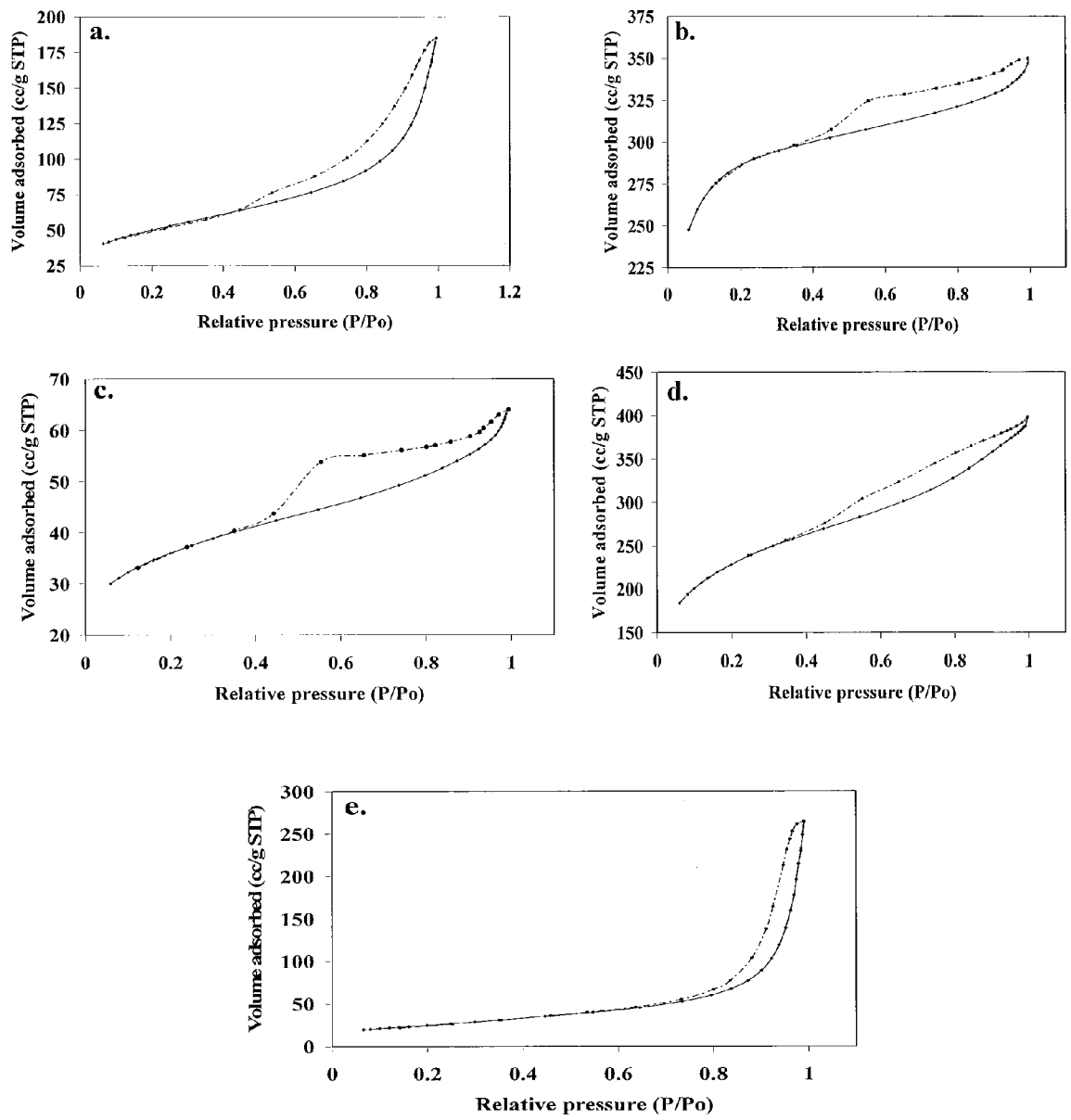
FIG. 18 shows $N_2$ adsorption-desorption isotherms of exemplary pure supports a. AC-Darco; b. AC-$RX_3$ extra; c. AC-Fluid coke; d. AC-CGP super; e. MWCNT.

The textural properties of the stabilized catalysts display some changes to that of pure supports. The mean pore diameter and % mesoposity were shifted towards higher values after the impregnation of alkali and metals on the supports. These results suggest that the addition of metals most likely block the micropores of the support.[71] The BET surface area and pore volume decrease were observed after the incorporation of metals, suggesting the partial pore blocking of the support by the metals. The blocking extent of the metal species was found to be high on the microporous activated carbon supported catalysts. The large surface area of the AC-CGP super supported catalyst indicates negligible blocking of pores with the impregnated metals. The decreased mesopore volume and surface area of AC-CGP super-supported catalyst indicated that the metal species block the mesopore pores of this support. In spite of the pore blockage, the mesoporous structural integrity of the MWCNT-supported alkali-promoted trimetallic C—Rh—Mo catalyst was unchanged from the support as seen from the $N_2$ adsorption-desorption isotherms of MWCNT support and the catalyst (FIG. 18e). These results suggest that MWCNTs have unique characteristics, such as uniform pore-size distribution, nano-sized channels, and mesoporous nature which make them a promising support for various catalytic applications.

Figure 19:
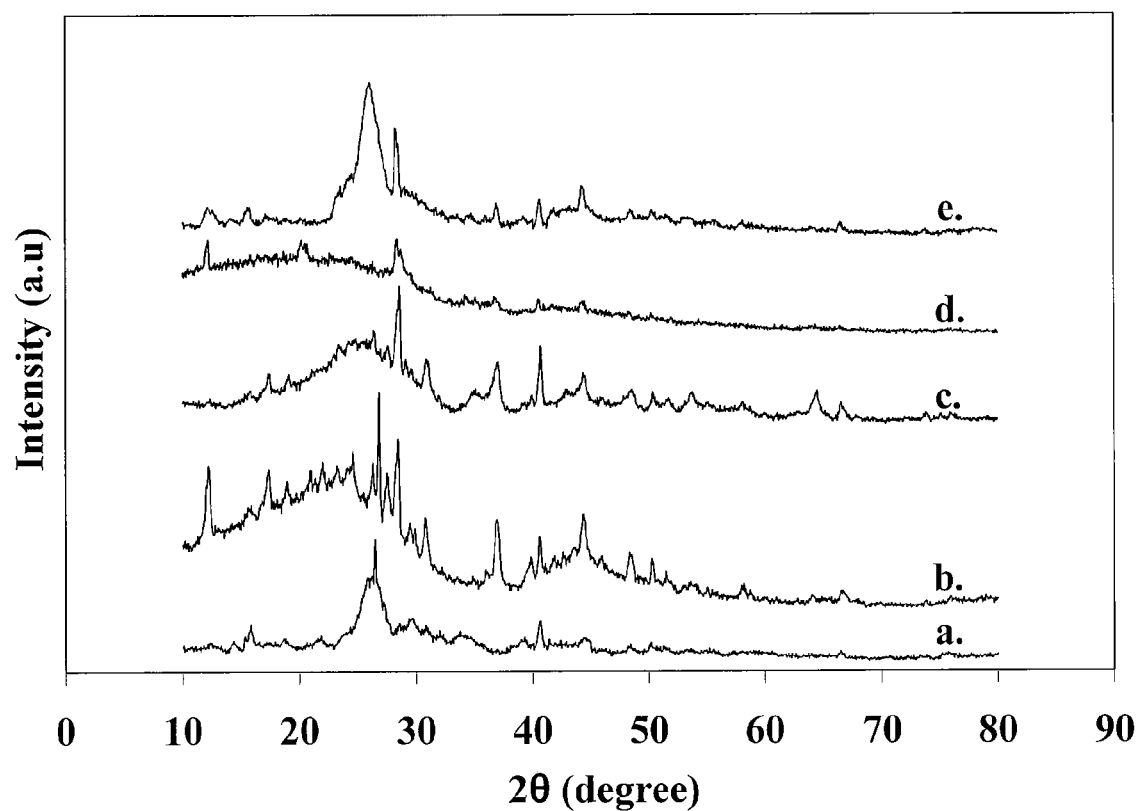
FIG. 19 shows XRD patterns of exemplary catalysts in oxidized form a. AC-Darco; b. AC-$RX_3$ extra; c. AC-Fluid coke; d. AC-CGP super; e. MWCNT.

FIG. 19 shows the XRD patterns of the alkali-promoted trimetallic Co—Rh—Mo catalysts supported on various activated carbons and that of the MWCNTs in oxide form. The JCPDS chemical spectra data bank was used to detect the most probable phases present in the samples. The variation in peak intensity of the catalysts was observed, confirming the role of the support on the dispersion of catalyst species. The strong intensity peak at 2θ value of 26.6° for the catalyst supported on MWCNTs is due to the reflections of the graphite phase. It is of interest to note that the graphite nature of the support was observed on micro porous activated carbons, AC-Darco and AC-RX$_3$ extra, whereas, the XRD patterns of the catalysts supported on mesoporous activated carbons, AC-Fluid Coke and AC-CGP super showed no graphite phase. The characteristic reflections corresponding to the crystalline structure of $MoO_3$ are observed at 2θ value of 40.7° on all the catalysts.[72] The peak at 2θ value of 28.4° corresponds to the characteristic reflections of the $K_2Mo_2O_7$ phase.[73] Other K—Mo—O phases, such as $KMo_4O_6$ (2θ=15.9, and 37.1°) also exist on these catalysts.[74,75]

TEM images of the AC-Darco, AC-RX$_3$ extra, AC-Fluid coke, AC-CGP super and MWCNT-supported catalysts were recorded and are as shown in FIG. 20. These micrographs reveal the morphology differences of alkali-promoted trimetallic Co—Rh—Mo catalysts supported on different supports and the development of a considerable amount of agglomerates, especially on the surface of the microporous activated carbon supported catalysts. The metal species are well dispersed on the mesoporous activated carbon support, AC-CGP super with particle size in the range of 3-6 nm (FIG. 20d). The TEM image of MWCNT-supported catalyst revealed that the catalyst particles are well dispersed both inside and outside the carbon nanotubes. The particle sizes of the metal species that are inside and outside of the tubes are in the range of 1 to 3 nm (FIG. 20e).

The results of the CO chemisorption of the sulfided catalysts are given in Table 9. The CO uptake values of 137 and 140 μmole/(g of cat.) were observed on the alkali promoted trimetallic catalysts supported on microporous activated carbon supports, AC-Darco and AC-RX$_3$ extra, respectively. Even though the surface area of the AC-RX$_3$ extra support is almost double, the pore volume and pore diameter are comparatively less than that of AC-Darco and hence about equal amounts of CO chemisorption was observed on these two supports. From the TEM images, it is observed that the formation of large particles takes place due to the agglomeration of metal species on the microporous activated carbon supports. This result in lower dispersions on these supports compared to that on mesoporous activated carbons. Due to the mesoporous nature of activated carbon supports, AC-Fluid coke and AC-CGP super, most of the metal deposition takes place inside the pores, resulting higher CO uptake values on these supports. The amounts of adsorbed CO on the surface of MWCNT-supported catalyst is found to be higher compared to all activated carbon supported catalysts, indicating the presence of large number of active sites on the catalyst. The metal dispersion of catalysts on different supports is in the following order: MWCNTs<AC-CGP super<AC-Fluid coke<AC-RX$_3$ extra<AC-Darco. The large pore volume and pore size of the MWCNT support facilitates uniform metal particle distribution and high metal dispersions. These results suggest that the catalyst supported on MWCNTs may perform better than catalysts supported on microporous, as well as, mesoporous activated carbons.

(b) Catalyst Activity and Selectivity Studies

Figure 21:
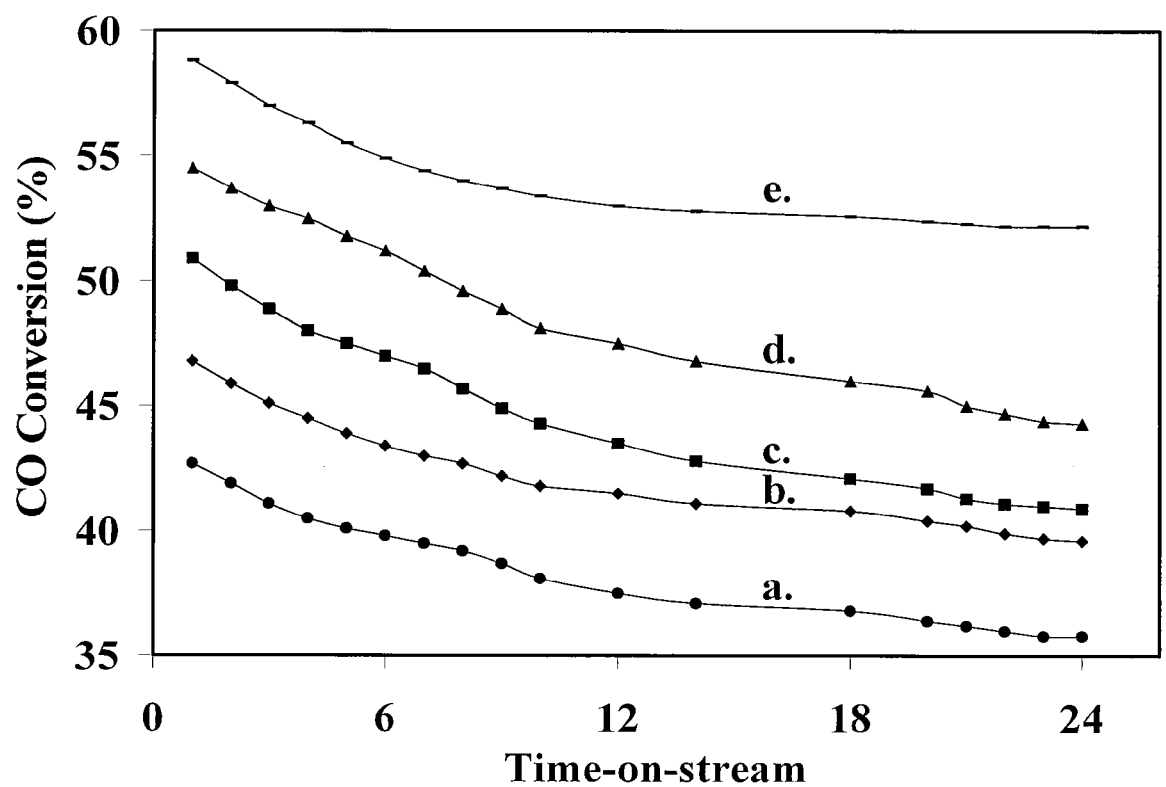
FIG. 21 shows CO Conversion (%) with time-on-stream for exemplary catalyst: a. AC-Darco; b. AC-$RX_3$ extra; c. AC-Fluid coke; d. AC-CGP super; e. MWCNT (wt. of the cat.=2 g, P=8.3 MPa, T=330° C., GHSV=3.6 m$^3$ (STP)/(kg of cat.)/h, $H_2$/CO molar ratio=2)

The catalyst activity studies towards higher alcohol synthesis reaction were carried out under similar conditions at 330° C., 8.3 MPa (1200 psig), 3.6 m$^3$ (STP)/(kg of cat.)/h, and $H_2$ to CO molar ratio of 2. FIG. 21 gives the results of the percentage CO conversion as time-on-stream during 24 h of higher alcohol synthesis over the different activated carbon and MWCNT-supported alkali modified trimetallic Co—Rh—Mo catalysts. It is observed that the CO hydrogenation activity of the supported catalysts followed the same order as that of CO chemisorption according to their pore structures. The stability of MWCNT-supported catalyst was much better than the catalysts supported on activated carbons. The uniform pore size distribution of the MWCNT support facilitates the large dispersion of metal particles on the support, which results in higher activity compared to that on activated carbon supported catalysts. The catalyst supported on AC-CGP Super showed high initial activity at the start-of-run, but dropped sharply as the reaction progressed within 24 h period. Similar stability results were observed on the AC-Fluid Coke supported catalyst. It can be deduced that the partially blocked mesopores by metal species raised the mass diffusion restriction of synthesis gas as well as products, thus decreasing the CO hydrogenation activity with time-on-stream. The analysis of the liquid products indicates that linear alcohols are formed and no branched alcohols were observed in the GC trace corresponding to the higher alcohols. Methanol, ethanol, n-propanol, and n-butanol are the major products, together with other higher alcohols. The analysis of exit gas indicates that methane is the major component apart from $CO_2$ and unconverted gases, such as, CO and $H_2$. Table 10 shows the activity and selectivity results obtained from CO hydrogenation over the sulfided alkali-promoted trimetallic Co—Rh—Mo catalysts after an induction period of 15 h. The term higher alcohols represents the ethanol and alcohols with carbon number greater than 2 ($C_{2+}$ alcohols). Over the catalysts supported on microporous activated carbons, AC-Darco and AC-$RX_3$ extra, the total alcohols space time yields (STY) of 0.141 and 0.154 g/(g of cat./h), respectively, were observed. Catalysts prepared on mesoporous activated carbon, AC-Fluid coke and AC-CGP super had substantially higher STY of alcohols of 0.187 and 0.202 g/(g of cat./h), respectively than microporous activated carbon supported catalysts. The support AC-CGP super has the advantage of high surface area, large pore diameter and pore volume compared to the other activated carbon supports. This results in high dispersion of active metal species on the surface as seen from the XRD profiles and CO chemisorption results, favouring the formation of alcohols. The STY of total hydrocarbons follow the similar trend as that of the total alcohols STY, whereas, the water-gas-shift reaction rate is almost constant on all activated carbon supported catalysts. It is also noted that the selectivity of methanol, ethanol and higher alcohols are almost constant on all the activated carbon-supported catalysts.

MWCNT-supported catalysts outperformed the catalysts supported on activated carbon. The total alcohols and total hydrocarbons STY of 0.296 and 0.345 g/(g of cat./h) were observed on this catalyst, whereas, the carbon dioxide formation rate is less compared to that of the activated carbon supported catalysts. These results explain that the pore size of the support has direct influence on the synthesis of mixed alcohols from synthesis gas. Support pore size can influence particle size distribution, dispersion, extent of reduction and plays an important role to diffuse the reactant molecules to the catalytically active centers that are located inside the pores. The micro-porous structure of activated carbon-supported catalysts causes pore plugging due to the formation of coke and deactivation of the catalyst, which results in transport limitation in the reaction. It is also worth to note that all these activated carbons are associated with 5-10% ash content as indicated by the manufacturer, whereas, the MWCNTs are highly purified and has almost negligible ash content.

Example 4

Higher Alcohols Synthesis from Synthesis Gas over Sulfided Alkali-Promoted Co—Rh—Mo Trimetallic Catalyst: Experimental and Modeling Studies Materials and Methods
(a) Catalyst Preparation
Catalysts were prepared as described in Example 1.
(b) Catalytic Studies
The higher alcohols synthesis reaction from synthesis gas was studied using a single-pass tubular downflow fixed-bed reactor of 450-mm length and 22-mm inside diameter made of inconel tube. The reactor was packed with 2 g of catalyst diluted with 12 ml of 90 mesh size silicon carbide and housed in an electric furnace controlled by a temperature controller. The reactor was pressurized with He to 500 psig (3.44 MPa) and sulfidation, together with reduction, were carried out for 6 h at 450° C. at a heating rate of 2° C./min using a gas mixture containing 10 mole % $H_2S$ in $H_2$ and a flow rate of 50 ml/min. The temperature was then lowered to the reaction temperature, and the system pressurized to the reaction conditions. The feed gas mixture (desired molar ratio of CO and $H_2$ mixed with 10 mole % Ar) was passed through mass flow controllers and the higher alcohols synthesis was carried out at steady-state under the reaction conditions over a period of 24 h. The product gas was cooled to 0° C. and separated into gas and liquid phases at the reaction pressure. The CO conversion and other gaseous products were monitored with a time interval of 1 h. The liquid products were collected at the end of the reaction and analyzed with a Varian 3400 gas chromatograph equipped with a capillary column and a flame ionization detector. The volume and weight of liquid products were measured to check the mass balance. The gaseous products were analyzed online on a Shimadzu gas chromatograph through a sampling valve. Using Ar as an internal standard, the CO conversion was calculated and the overall mass balance of the reaction was determined.
(c) Experimental Design
The parameters T, P, and GHSV were varied in the ranges of 275 to 350° C., 800 to 1400 psig (5.52-9.65 Mpa), and 2.4 to 4.2 $m^3$ (STP)/(kg of cat.)/h, respectively. To analyze the interaction effects between the operating parameters for higher alcohols synthesis and to optimize the effective parameters, the Taguchi orthogonal array design method was used to develop the experimental plan. This statistical design approach minimizes the overall variance of the estimated parameters and reduces the number of trials required without restricting the confidence region for the estimated parameter.[76] An orthogonal array selector determines the number of trials necessary and the factor levels for each parameter in each trial.[77] The experiments were designed using Design-Expert software version 6.0.1, and were performed using a feed gas mixture of 45 mole % CO, 45 mole % $H_2$, and 10 mole % Ar. Specific experimental conditions were repeated several times to observe the reproducibility of the results. A separate set of experiments were performed to study the effect of the $H_2$ to CO molar ratio on higher alcohols synthesis at the optimum conditions of T, P, and GHSV.

The perturbation plots were used in conjunction with the 3-D surface responses, as interpreting the 3-D surface response alone can be difficult.[27] Perturbation plots were used to show the effect of each individual variable as the others were held constant. This plot is a powerful method of comparing the relative influences of factors, and can be used to look at one-dimensional paths through a multifactor surface.

Results and Discussion

Analysis of the liquid products indicates that the alcohols likely followed the CO insertion mechanism; forming linear alcohols.[55] Methanol, ethanol, n-propanol, and n-butanol are the major products, together with other higher alcohols. The term higher alcohols represent alcohols with a carbon number greater than 1, whereas, total alcohols represent methanol and higher alcohols combined. The analysis of exit gas indicates that methane is the major hydrocarbon component apart from $CO_2$, unconverted CO, and $H_2$.

Figure 22:
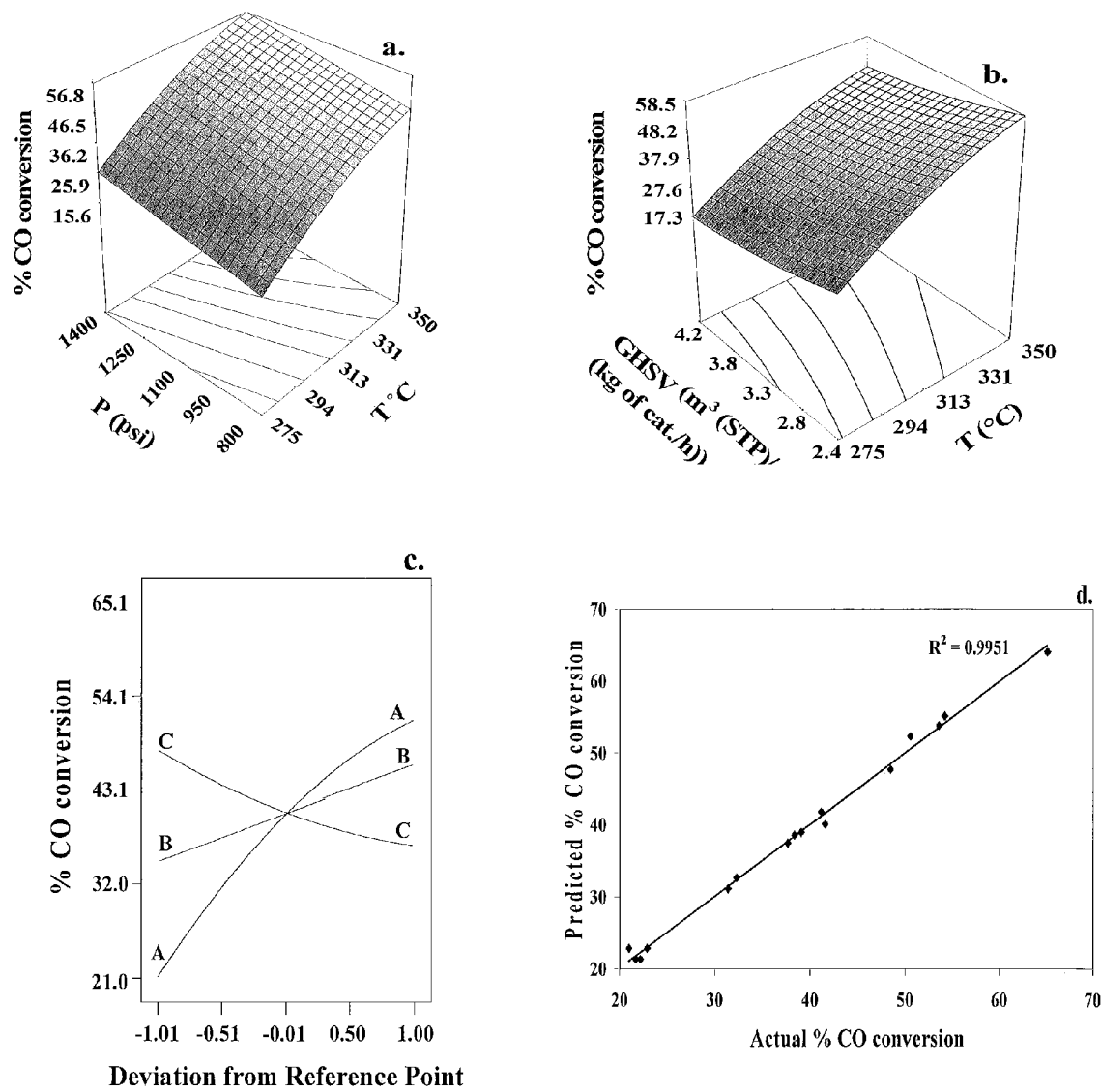
FIG. 22 shows the effects of the temperature, pressure, and gas hourly space velocity on % CO conversion over the exemplary Co—Rh—Mo—K/MWCNT catalyst; a. and b. 3-D surface responses, c. Perturbation plot; d. Quality of fit.

(a) Effects of the Temperature, Pressure, and Gas Hourly Space Velocity on % CO Conversion FIGS. 22a and 22b are three-dimensional (3-D) plots of the effects of T, P, and GHSV on % CO conversion. The plots show that inlet % CO conversion increased monotonically with increasing reaction temperature and pressure from 275 to 350° C. and 800 to 1400 psig, respectively. This confirms that the hydrogenation of CO over the MWCNTs-supported alkali-promoted trimetallic Co—Rh—Mo catalyst was greatly improved at high temperature and pressure. With increased GHSV from 2.4 to 4.2 $m^3$ (STP)/(kg of cat.)/h, it was observed that the % CO conversion decreased monotonically.

Short contact time between the reactants at high GHSV resulted in the low CO conversion. FIG. 22c is the perturbation plot showing that the effects of the variables T, P, and GHSV are significant on % CO conversion. FIG. 22d compares the experimental values to the predicted % CO conversion, and clearly shows that the model for % CO conversion is valid within the experimental ranges.

Figure 23:
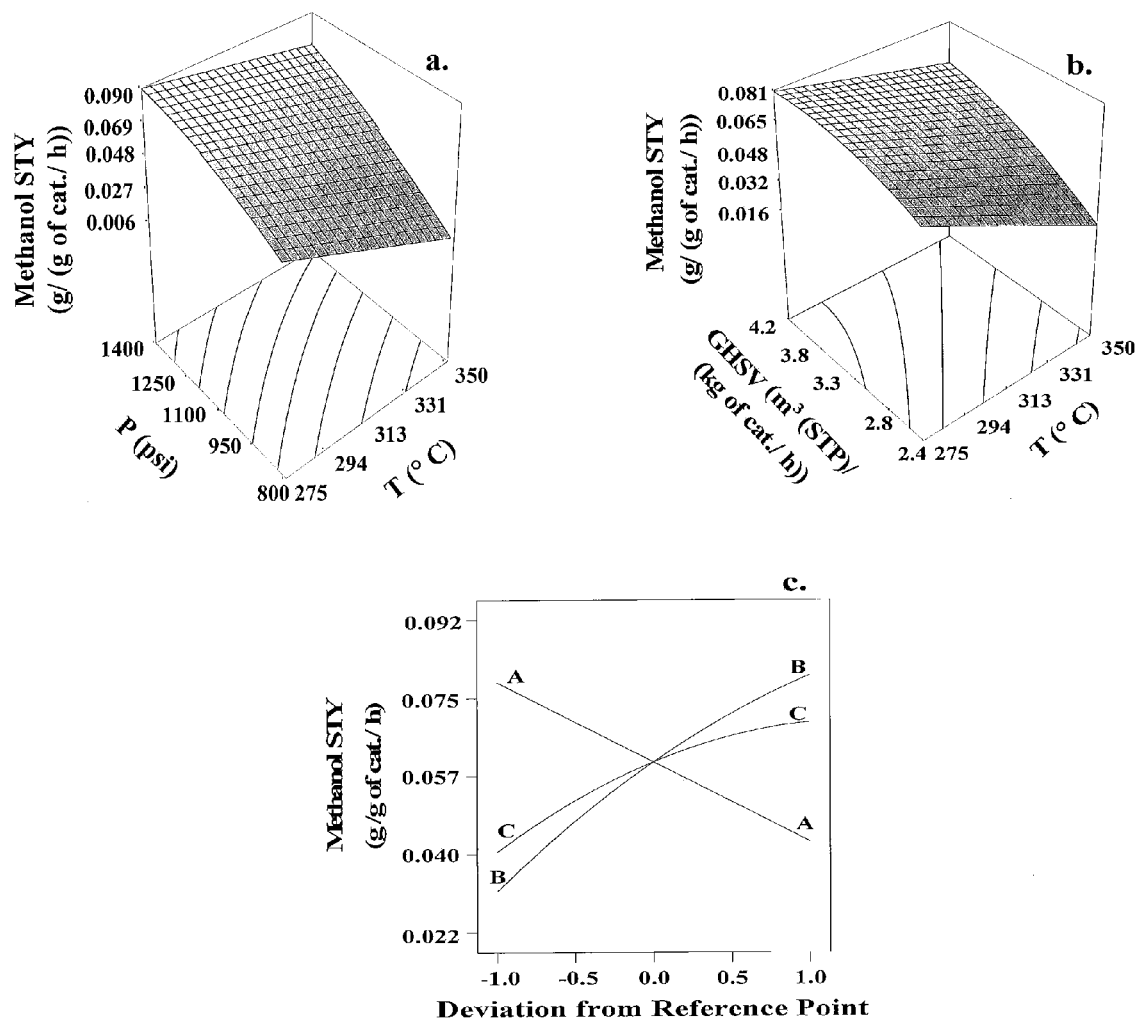
FIG. 23 shows the effects of the temperature, pressure, and gas hourly space velocity on methanol STY over the exemplary Co—Rh—Mo—K/MWCNT catalyst; a. and b. 3-D surface responses, c. Perturbation plot.

(b) Effects of the Temperature, Pressure, and Gas Hourly Space Velocity on STY of Alcohols, Hydrocarbons, and $CO_2$ FIGS. 23a and 23b (3-D response surface) and FIG. 23c (perturbation plot) depict the effects of T, P, and GHSV on STY of methanol using $H_2$ to CO molar ratio equal to 1. The methanol STY decreased monotonically with increasing temperature, suggesting that conversion of methanol to higher alcohols takes place at high temperatures. The formation of methanol increased monotonically with increasing pressure and GHSV. At high GHSVs, the consumption of methanol to higher alcohols is low, which explains the high methanol yields. Table 11 shows the $R^2$ value of 0.993 obtained from the fitness of the experimental methanol STY values with that of the predicted values, confirms that the model fits well within the experimental conditions.

Figure 24:
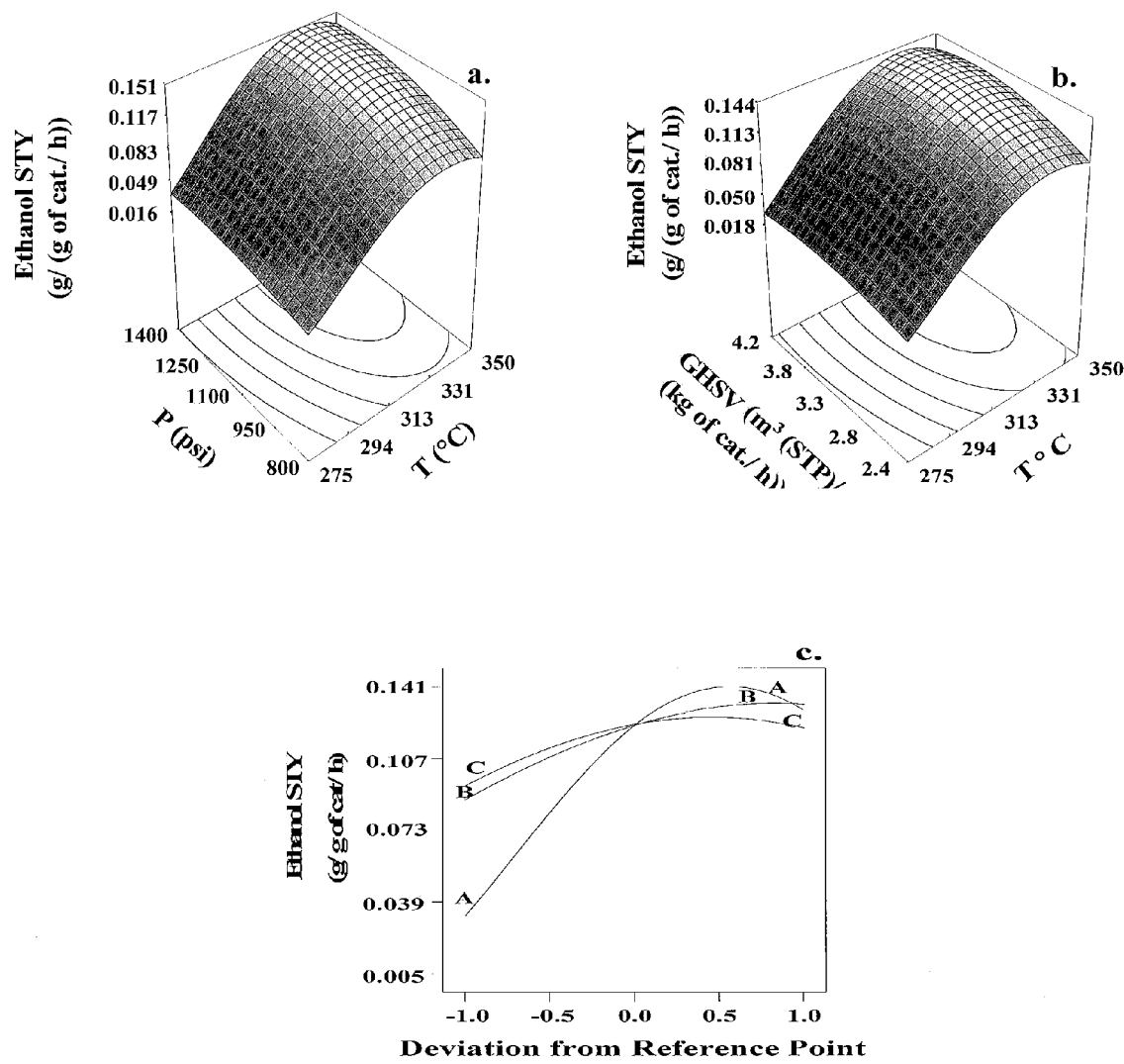
FIG. 24 shows the effects of the temperature, pressure, and gas hourly space velocity on ethanol STY over the exemplary Co—Rh—Mo—K/MWCNT catalyst; a. and b. 3-D surface responses, c. Perturbation plot.

The effects of T, P, and GHSV reactions on the STY of ethanol at $H_2$ to CO molar ratio of 1 are represented as 3-D plots in FIGS. 24a and 24b and the perturbation plot in FIG. 24c. Compared to P and GHSV, temperature had great effect on ethanol STY, with the rate of ethanol formation reaching a maximum value and then decreasing at higher temperatures. Depending on the temperature, the ethanol formation increased up to certain pressures and then remained constant. With respect to GHSV, a maxima in the ethanol STY was also observed. The model fits the experimental results with an $R^2$ value of 0.981 as seen from Table 11. Higher alcohols STY exhibit similar trends of operating conditions dependency as that of ethanol STY, with the maximum amount of higher alcohols formation observed with respect to temperature and GHSV. With increased pressure, the higher alcohols STY increased to a certain value and then remained constant at higher pressures. The fit of the model is good with an $R^2$ value of 0.980 (Table 11).

Figure 25:
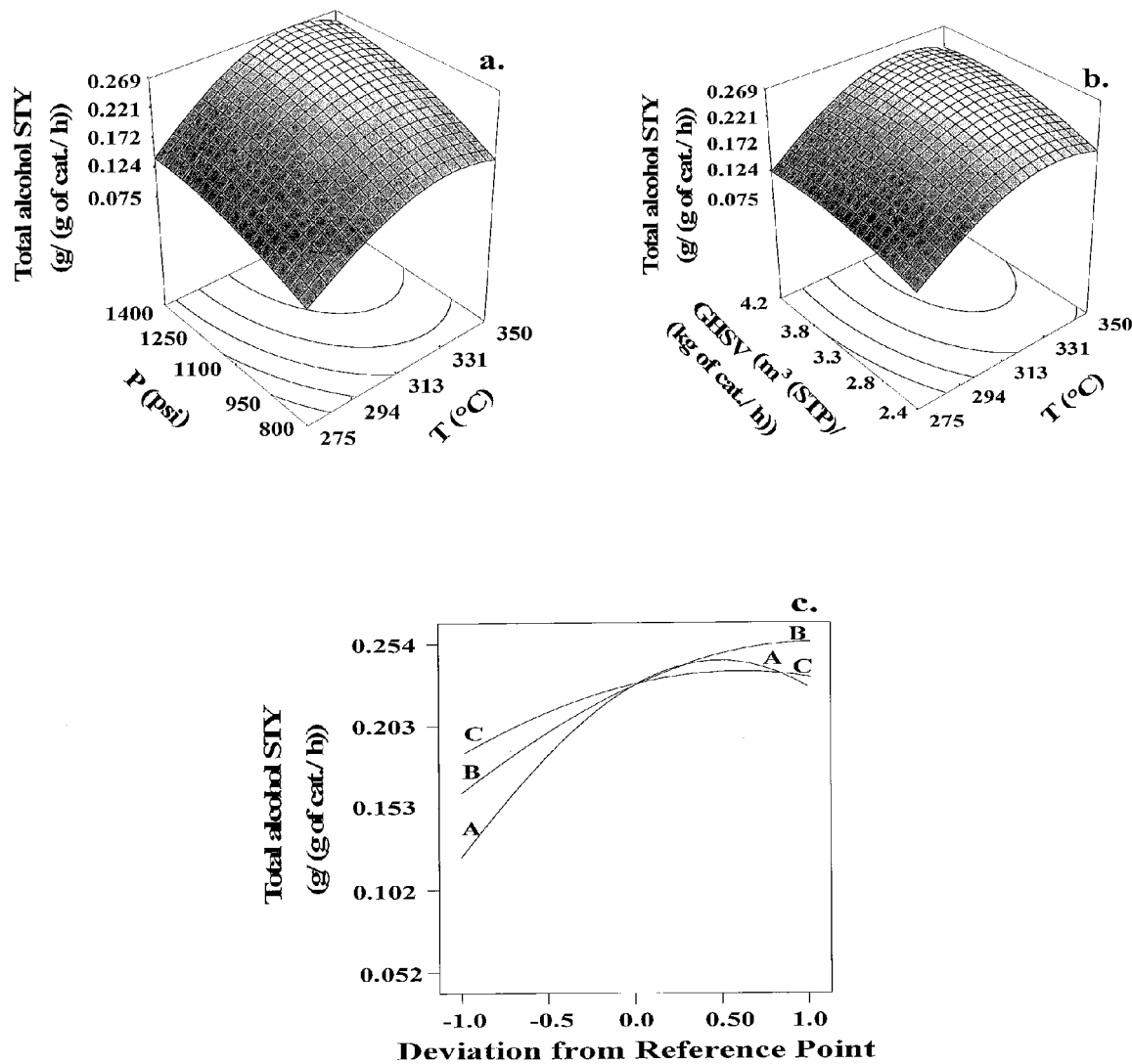
FIG. 25 shows the effects of the temperature, pressure, and gas hourly space velocity on total alcohol STY over the exemplary Co—Rh—Mo—K/MWCNT catalyst; a. and b. 3-D surface responses, c. Perturbation plot.

The dependence of total alcohol formation on the T, P, and GHSV reactions at $H_2$ to CO molar ratio of 1 are presented as 3-D plots in FIGS. 25a and 25b and the perturbation plot in FIG. 25c. Table 10 displays the quality of the model's fit with an $R^2$ value of 0.982. The total alcohols STY exhibits the maximum with respect to reaction temperature. Increased pressure favors the formation of total alcohols, whereas, the STY of total alcohols increased to a certain value and then remained constant with increasing GHSV. FIG. 25c shows that GHSV had a small effect on total alcohols STY, compared to that of T and P.

Figure 26:
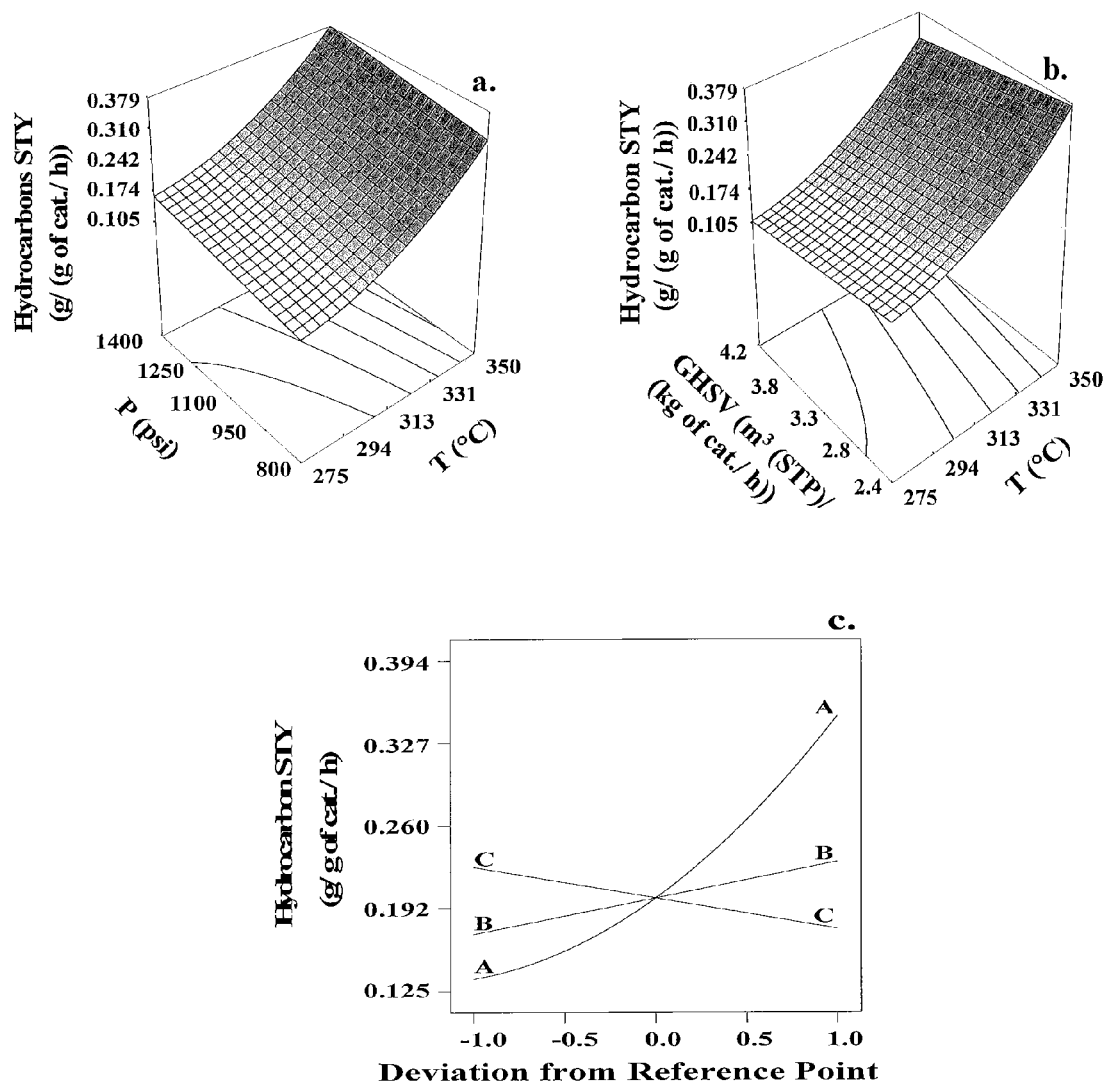
FIG. 26 shows the effects of the temperature, pressure, and gas hourly space velocity on hydrocarbon STY over the exemplary Co—Rh—Mo—K/MWCNT catalyst; a. and b. 3-D surface responses, c. Perturbation plot.

FIGS. 26a, 26b, and 26c exhibit the dependency of operating conditions (T, P, and GHSV) on hydrocarbons STY at $H_2$ to CO molar ratio of 1. As observed, the formation of hydrocarbons exponentially increases at high reaction temperatures. These results combined with total alcohols STY suggest that the produced alcohols are consumed to form hydrocarbons with synthesis gas at higher temperatures. Hydrocarbon STY increased slightly with increasing pressure, whereas, the hydrocarbon formation decreased with GHSV. Table 10 shows that the model fits well with the experimental results. The $CO_2$ formation model follows a similar trend as that of the hydrocarbon formation. Compared to that of hydrocarbons, higher STY of $CO_2$ were observed at all experimental conditions. Table 10 shows that the $CO_2$ model fits with $R^2$ value of 0.954.

Figure 27:
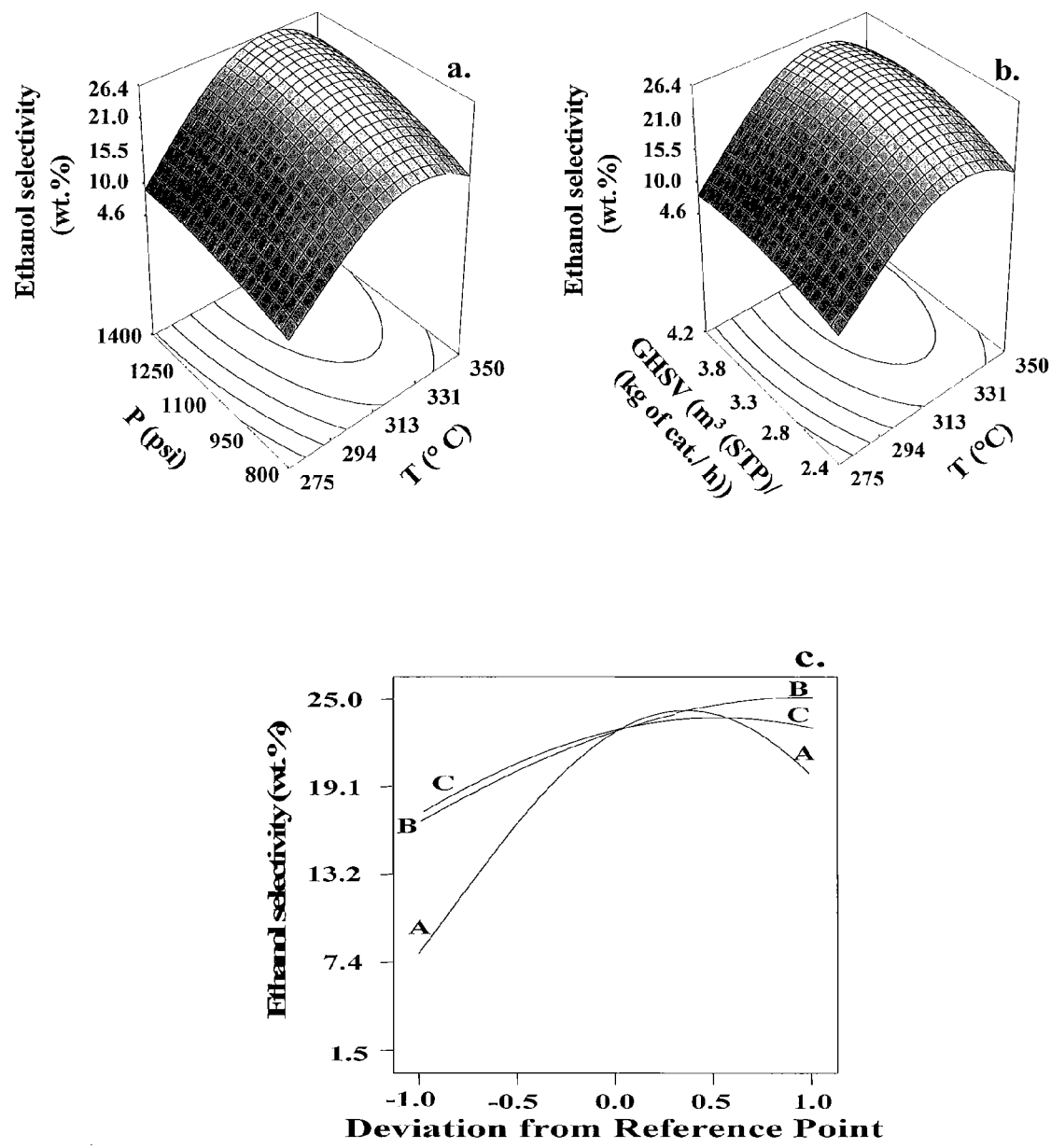
FIG. 27 shows the effects of the temperature, pressure, and gas hourly space velocity on ethanol selectivity over the exemplary Co—Rh—Mo—K/MWCNT catalyst; a. and b. 3-D surface responses, c. Perturbation plot.

(c) Effects of the Temperature, Pressure, and Gas Hourly Space Velocity on Selectivity of Alcohols The influence of the operating conditions T (275 to 350° C.), P (800 to 1400 psig), and GHSV (2.4 to 4.2 $m^3$ (STP)/(kg of cat.)/h) on selectivities of methanol, ethanol, higher alcohols, and total alcohols using $H_2$ to CO molar ratio of 1 were investigated. There was good agreement between the simulated results and the experimental observations (Table 12). The methanol selectivity decreased monotonically with increasing temperature, but increased with increasing pressure and GHSV. The ethanol (FIG. 27), higher alcohols, and total alcohols selectivities displayed a pronounced increase with increasing temperature and reached a maximum value, suggesting that the significant activity for the dehydration of alcohols takes place at higher temperatures. With increasing pressure, ethanol selectivity increased to a certain value and remained constant, whereas, a maximum was obtained with increased GHSV (FIG. 27). The higher alcohols and total alcohols selectivity monotonically increased with increasing pressure and GHSV. This discrepancy between the ethanol and higher alcohols selectivities at higher pressures and GHSVs is due to the increasing ability of chain growth from ethanol to higher alcohols.

(d) Optimization of Operating Conditions

The optimum operating conditions using $H_2$ to CO molar ratio of 1 were defined according to the following constraints: (1) Ethanol STY to be maximum; and (2) ethanol selectivity to be maximum. The solution for the model was obtained as follows: T=330° C., P=1320 psig (9.1 Mpa), GHSV=3.8 $m^3$ (STP)/(kg of cat.)/h. The experiments were performed at these operating conditions, with both the ethanol STY and selectivity presented together with the model predictions. The difference of ethanol STY was around 3% and that of the selectivity was less than 5%.

Figure 28:
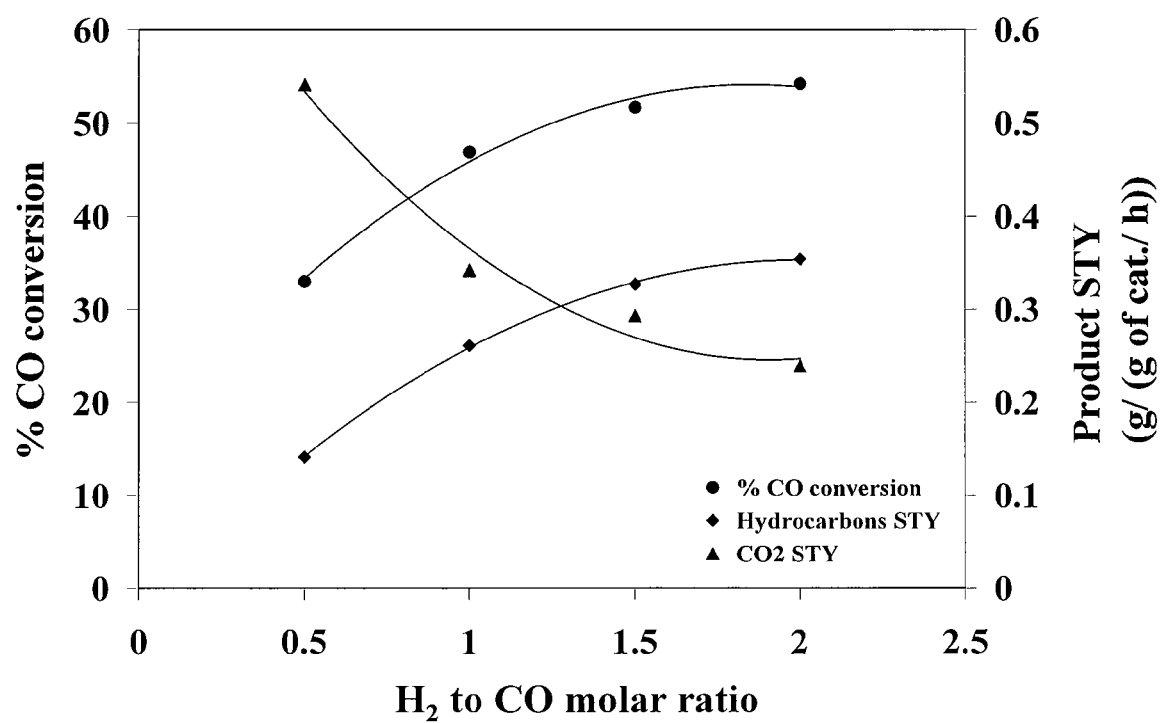
FIG. 28 shows the effect of the $H_2$ to CO molar ratio on % CO conversion, hydrocarbons, and $CO_2$ STY over the exemplary Co—Rh—Mo—K/MWCNTs catalyst at 330° C., 1320 psig, and 3.8 m$^3$ (STP)/(kg of cat.)/h.

(e) Effects of $H_2$ to CO Molar Ratio on Higher Alcohols Synthesis from Synthesis Gas In this study, the $H_2$ to CO molar ratio (Θ) was varied from 0.5 to 2.0 and the experiments were carried out using the optimum operating conditions of T, P, and GHSV reported in (d). FIG. 28 depicts the influence of Θ on the % CO conversion, hydrocarbons STY, and $CO_2$ STY. The results show that increasing the Θ from 0.5 to 2.0 led to increased % CO conversion from 33.0 to 54.2%, suggesting that the catalyst activity is improved with Θ.

Figure 29:
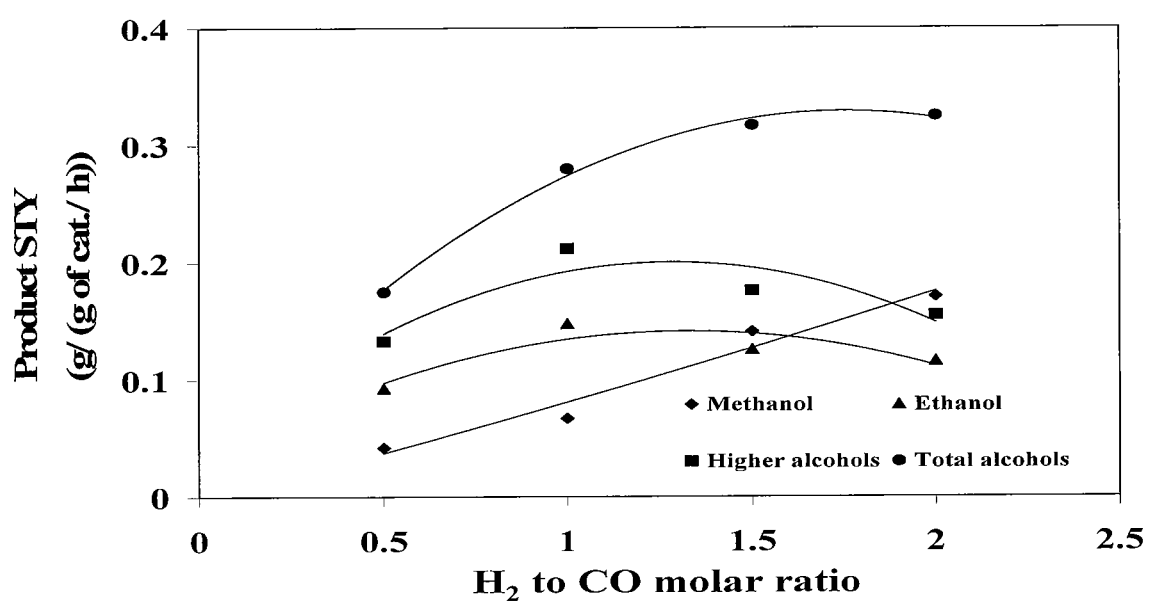
FIG. 29 shows the effect of the $H_2$ to CO molar ratio on methanol, ethanol, higher alcohols, and total alcohols STY over the exemplary Co—Rh—Mo—K/MWCNT catalyst at 330° C., 1320 psig, and 3.8 m$^3$ (STP)/(kg of cat.)/h.

The hydrocarbons formation rate increased monotonically from 0.141 to 0.354 g/(g of cat.)/h, whereas the $CO_2$ STY decreased monotonically from 0.541 to 0.239 g/(g of cat.)/h with increasing Θ from 0.5 to 2.0. The responses of methanol, ethanol, higher alcohols, and total alcohols formation (FIG. 29) show that the rate of methanol formation increased with increasing Θ, while the ethanol and higher alcohols STY revealed their maximum at Θ value between 1 to 1.5. FIG. 29 also shows that the total alcohols formation increased to specific Θ and remained constant.

While not wishing to be limited by theory, these results can be explained from the CO insertion mechanism of higher alcohols synthesis reaction[55]. The partial pressure of CO was high at low values of Θ, which resulted in enhanced CO insertion and C—C chain growth favoring the formation of compounds with a carbon number greater than 1. With increasing Θ value, the partial pressure of $H_2$ increased, resulting in the formation of $C_1$ products, such as methanol and methane. Because of a decreased amount of higher alcohols and hydrocarbons with a carbon number greater than 1, the water gas shift reaction rate was low due to small water formation.

Figure 30:
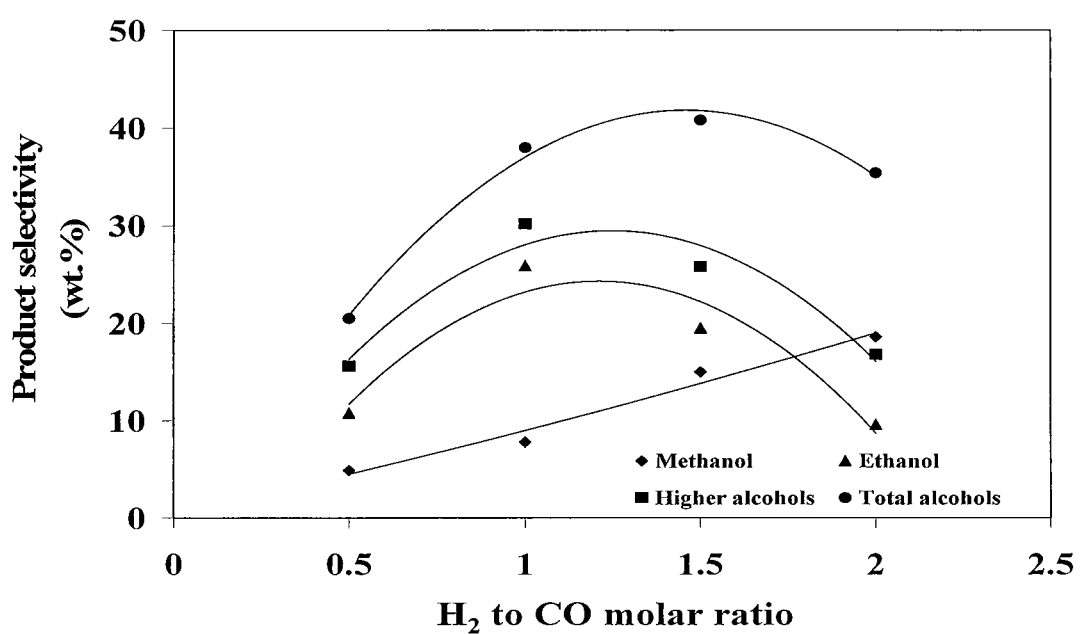
FIG. 30 shows the effect of the $H_2$ to CO molar ratio on methanol, ethanol, higher alcohols, and total alcohols selectivity over the exemplary Co—Rh—Mo—K/MWCNT catalyst at 330° C., 1320 psig, and 3.8 m$^3$ (STP)/(kg of cat.)/h.

The selectivities of methanol, ethanol, and higher alcohols exhibit similar trends as that of their STYs (FIG. 30). Methanol selectivity monotonically increased from 4.9 to 18.6 wt %, with increased Θ from 0.5 to 2.0. A maxima was observed in the selectivity of ethanol and higher alcohols at around Θ value of 1.25, whereas the total alcohols selectivity showed a maximum at Θ value of approximately 1.5.

(f) Reproducibility Study

Reproducibility of the experimental data was tested at optimum operating T, P, and GHSV using Θ values of 1, 1.5, and 2, and the results representing ethanol STY and selectivity are reported in Table 13. Some experimental conditions were repeated to determine the t- and p-values. To determine the effect of packing on the experimental results, the reactor was reloaded with a fresh batch of catalyst and the experiments and repetitions were carried out. The unequal sample sizes equal variance Student's t test method was used to determine reproducibility of the results. The results indicated that the calculated p-value associated with the t test was not small (>0.05), providing evidence that the means are not different. This proves that the data are reproducible with small (<±5) experimental errors.

Example 5

Intrinsic Reaction Kinetics of Higher Alcohols Synthesis from Synthesis Gas over Sulfided Alkali-Promoted Co—Rh—Mo Trimetallic Catalyst Supported on Multi-Walled Carbon Nanotubes The heterogeneous catalytic reaction is associated with external and internal diffusional resistances. The diffusion of the reactants or products between the bulk fluid and the external surface of the catalyst is known as external resistance, and diffusion of the reactants from the external surface (pore mouth) to the interior of the particles and diffusion of the products from the interior of the particles to the external surface is referred as internal resistance.[78] Reaction rates in the absence of these internal and external diffusion resistances are termed as intrinsic kinetics.[79]

Materials and Methods (a) Catalyst preparation

The catalysts were prepared as described in Example 1. After stabilization, the catalysts were palletized and then ground to different particle sizes.

(b) Catalyst Characterization

The contents of Mo, Co, and Rh of different particle size pellet samples were determined using a Perkin-Elmer ELAN 5000 inductively coupled plasma mass spectroscopy (ICP-MS) instrument as described in Example 1.

(c) Catalytic Studies

Figure 31:
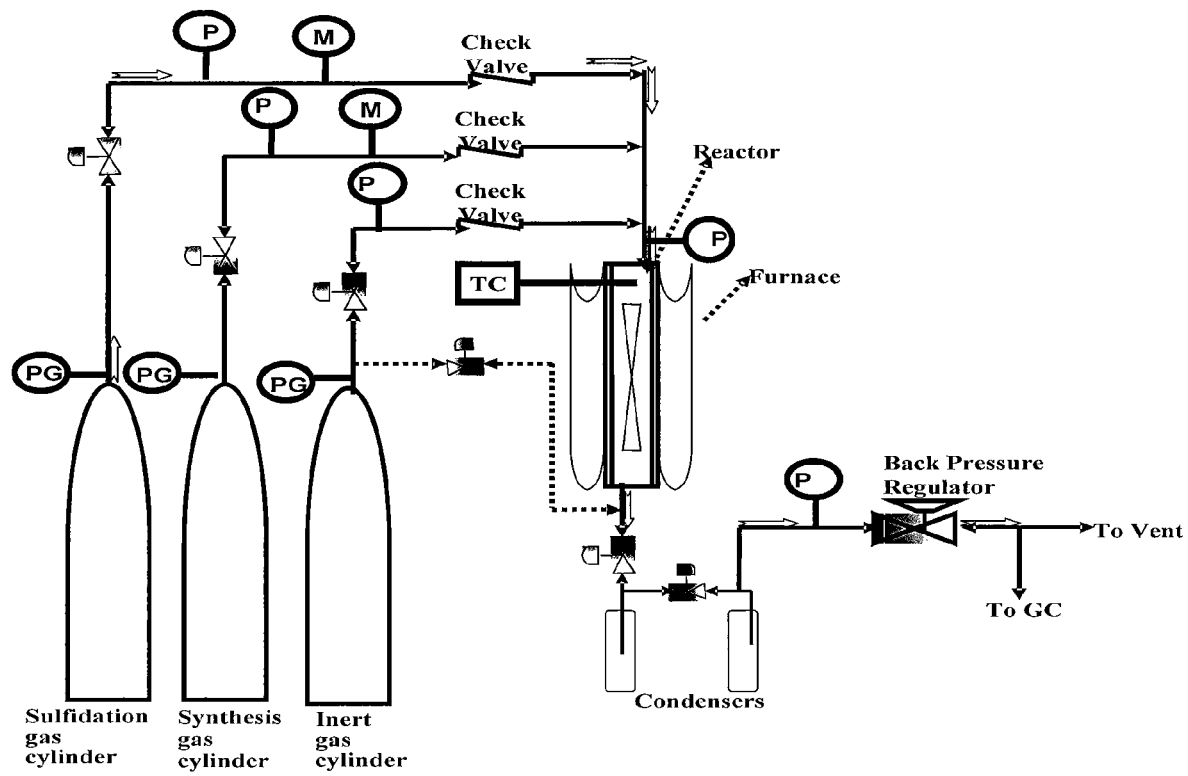
FIG. 31 shoes an exemplary experimental set-up for higher alcohols synthesis from synthesis gas.

The higher alcohols synthesis was tested in an experimental unit (FIG. 31), which had a single-pass tubular downflow fixed-bed reactor of 450-mm length and 22-mm inside diameter, made of inconel tube. The reactor was packed with 2 g of catalyst diluted with 12 ml of 90 mesh size silicon carbide and housed in an electric furnace controlled by a temperature controller. The reactor was pressurized with He to 500 psig (3.44 MPa) and the sulfidation, together with the reduction, was carried out for 6 h at 450° C. at a heating rate of 2° C./min using a gas mixture containing 10 mole % $H_2S$ in $H_2$ and a flow rate of 50 ml/min. The temperature was then lowered to the reaction temperature, and the system pressurized to the reaction conditions. The feed gas mixture (desired molar ratio of CO and $H_2$ mixed with 10 mole % Ar) was passed through mass flow controllers and the higher alcohols synthesis was carried out at steady-state under the reaction conditions over a period of 24 h, after an initial induction period of 15 h. The product gas was cooled to 0° C. and separated into gas and liquid phases at the reaction pressure. The CO conversion and other gaseous products were monitored with a time interval of 1 h. After an induction period on 15 h, the liquids were removed from the condensers. The variation in gas concentration is found to be little after an induction period, and hence, constant values of liquid concentrations are assumed during that reaction time. The liquid products were collected at the end of the reaction and analyzed with a Varian 3400 gas chromatograph equipped with a capillary column and a flame ionization detector. The volume and weight of liquid products were measured to check the mass balance. The gaseous products were analyzed online on a Shimadzu gas chromatograph through a sampling valve. Using Ar as an internal standard, the CO conversion was calculated and the overall mass balance of the reaction was determined.

(d) Experimental Design for Intrinsic Kinetics

Four parameters, such as reactor temperature (T), pressure (P), gas hourly space velocity (GHSV), and $H_2$ to CO molar ratio were varied using four different levels in the ranges of 275-350° C., 800-1400 psig (5.52-9.65 MPa), 2.4-4.2 $m^3$ standard temperature and pressure (STP)/(kg of cat.)/h, and 0.5-2.0, respectively. A Taguchi orthogonal array method was used to develop the experimental plan to analyze the intrinsic kinetics for higher alcohols synthesis from synthesis gas, and the set of experiments are shown as set 1 in Table 14. Design-Expert software, version 6.0.1 was used to design the set of experiments performed in this study. The experiments were performed randomly, and the center-point experiment was repeated after every four runs during the activity tests to verify the catalyst stability. Additional experiments were designed using a $H_2$ to CO molar ratio of 1.25 and performed at the conditions as listed as set 2 in Table 14. Each run was performed over a period of 24 h using 2 g of catalyst. The catalytic activity and product selectivity data were calculated after an induction period of 15 h. The catalyst was kept under a constant inert gas (He) flow of 50 ml/min between the runs, when it was necessary to shut down the reactor.

Results and Discussion
(a) External Mass-Transfer Diffusion

The external mass-transfer diffusion can be eliminated by decreasing the mass-transfer boundary layer thickness, which is the distance from a solid object to the region where the concentration of the diffusing species reaches 99% of the bulk concentration. This can be eliminated by increasing the velocity past the particle or using very small particles.[78] To determine the effect of external mass transfer on the performance of the K-promoted Co—Rh—Mo/MWCNTs catalyst for CO hydrogenation, sample pellets of different particle size ranges of 707-841, 420-500, 210-297, and 147-210 μm with average particle sizes of 0.774, 0.460, 0.254, and 0.179 mm, respectively, were prepared.

To confirm the homogeneous distribution of active sites through the pellet and from pellet to pellet, the samples were collected from different catalyst pellets and the metal contents of these samples were analyzed using ICP-MS. The results were given in Table 15 along with the targeted compositions. From this table, it is clear that the measured contents of the prepared catalysts are slightly lower compared to targeted values, which may be due to the hygroscopic nature of precursors. The metal contents of different sample pellets are found to be comparable, confirming the uniform distribution of active sites through the catalyst.

Figure 32:
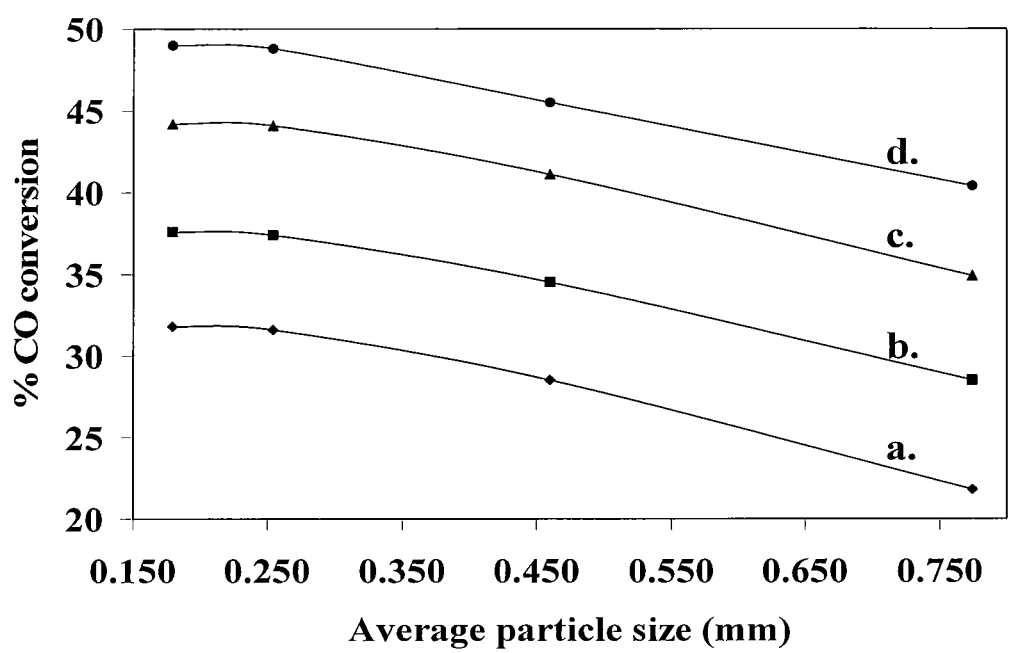
FIG. 32 shows the effect of particle size on % CO conversion; a. 275° C.; b. 300° C.; c. 325° C.; d. 350° C. for an exemplary K-promoted Co—Rh—Mo/MWCNT catalyst (wt. of the cat.=2 g, P=9.1 MPa, GHSV=3.6 m$^3$ (STP)/(kg of cat.)/h, $H_2$ to CO molar ratio=1.25).
Figure 33:
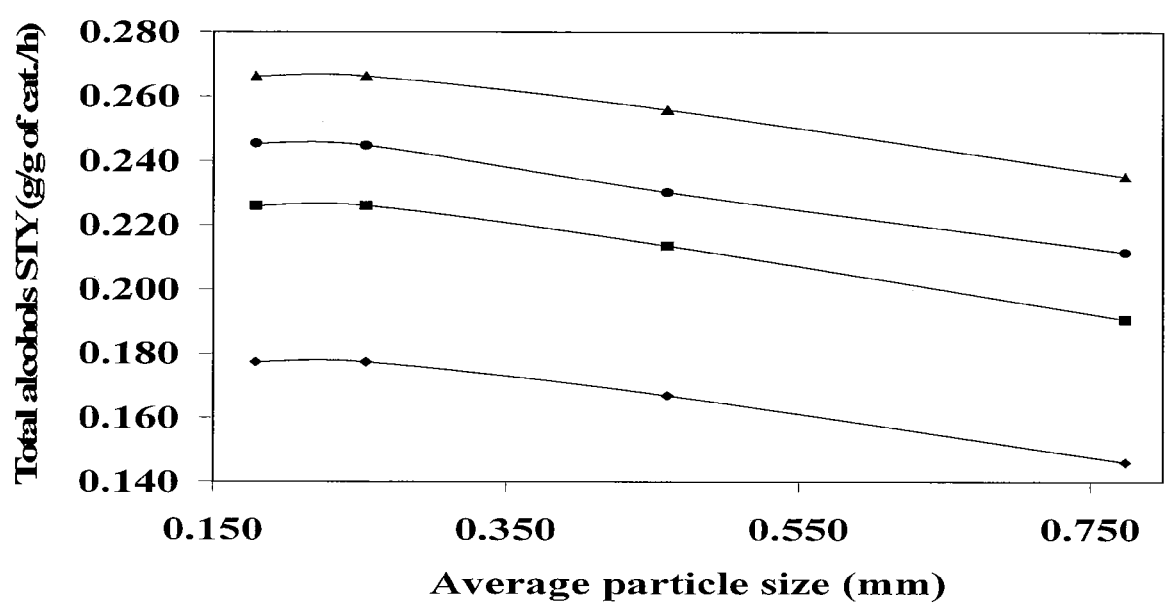
FIG. 33 shows the effect of particle size on total alcohols STY a. 275° C.; b. 300° C.; c. 325° C.; d. 350° C., for an exemplary k-promoted Co—Rh—Mo/MWCNT catalyst (wt. of the cat.=2 g, P=9.1 MPa, GHSV=3.6 m$^3$ (STP)/(kg of cat.)/h, $H_2$ to CO molar ratio=1.25).

The effect of the particle size on external mass-transfer diffusion was studied by performing the experiments at an inlet pressure of 1320 psig (9.1 MPa), flow rate of 120 ml/min, and reaction temperatures in the range of 275-350° C. For each experiment, 2 g of catalyst was used and the reaction was carried out using a feed gas mixture of CO (40 mole %), $H_2$ (50 mole %), and Ar (10 mole %). FIGS. 32 and 33 show the % CO conversions and total alcohols space time yield (STY) of the catalysts with different particle sizes at different temperatures, respectively. The % CO conversion and total alcohol STY increased linearly at all reaction temperatures with decreasing catalyst average particle size from 0.774 to 0.254 mm, but no significant change was observed in the reaction with further decreasing particle size to 0.179 mm. These results suggested that the catalyst particle size has a great influence on the higher alcohols synthesis from synthesis gas and that the mass transfer across the boundary layer limited the rate of reaction, using the catalyst with a particle size greater than 0.254 mm. Use of the catalyst with an average particle size less than 0.254 mm ensured that the film resistance to external mass transfer was negligible for the kinetic parameter estimation experiments, and hence, the catalyst with a particle size in the range of 147-210 μm was selected.

The Frossling correlation[80] is used in flow around spherical particles to obtain the relation between the particle size ($d_p$) of the catalyst, mass-transfer coefficient ($k_c$), and boundary layer thickness (δ). The required parameters and constants for the estimation of Frossling correlation are calculated. The mass-transfer correlation is given as follows:

$$Sh = 2 + 0.6(Re)^{1/2}(Sc)^{1/3} \quad (1)$$

$$Sh = \frac{k_c d_p}{D_e} \quad (2)$$

$$Re = \frac{\rho u d_p}{\mu} \quad (3)$$

$$Sc = \frac{\mu}{\rho D_e} \quad (4)$$

where $k_c$ is the average mass transfer coefficient of a reactant from the bulk flow to catalyst surface (m/s), $d_p$ is the average diameter of the catalyst particle (m), $D_e$ is the effective diffusivity for a binary gas mixture (m²/s), u is the free stream velocity of fluid (m/s), ρ is the gas density (kg/m³), and μ is the gas dynamic viscosity (kg/(m-s)).

Table 16 shows results of the mass-transfer coefficient of carbon monoxide from the bulk flow to the surface of the catalyst particle ($k_c$) and the boundary layer thickness (δ) calculated using the Frossling correlation. From these results, it is observed that decreasing $d_p$ of catalyst particles from 0.774 to 0.179 mm, increased $k_c$ value about 3 times more and decreased δ about 3 times less than that of the initial value. It is also noted that the temperature has a negligible effect on the external mass-transfer diffusion.

Figure 34:
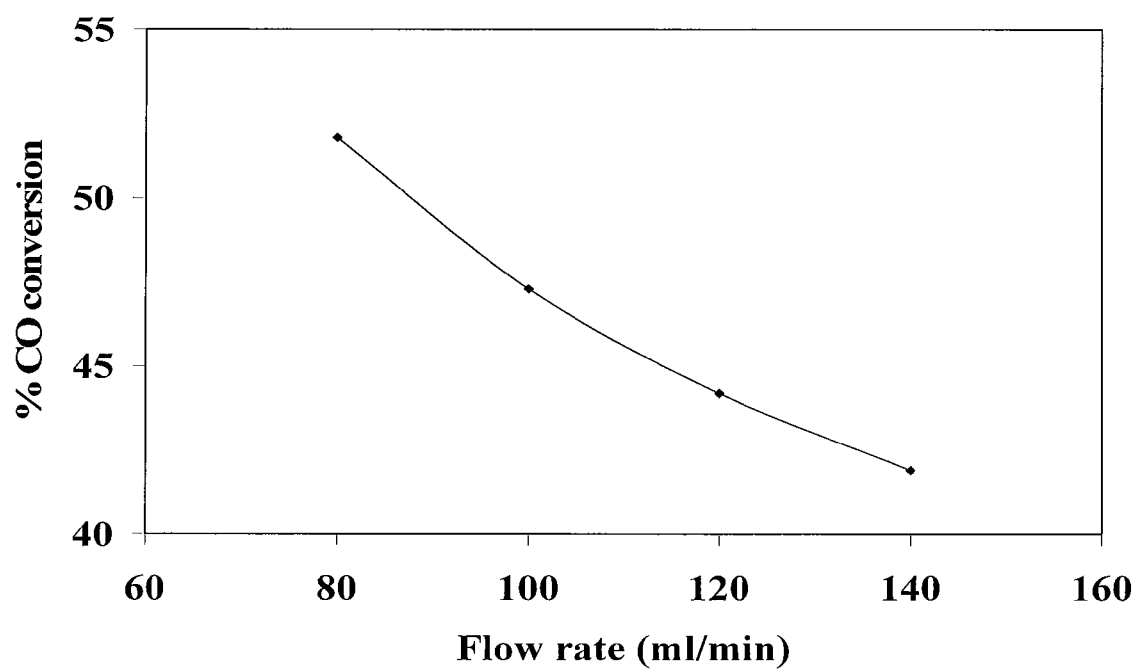
FIG. 34 shows the effect of flow rate on % CO conversion for an exemplary K-promoted Co—Rh—Mo/MWCNT catalyst (wt. of the cat.=2 g, T=325° C., P=9.1 MPa, $H_2$ to CO molar ratio=1.25, Average particle size=0.179 mm ml/min).
Figure 35:
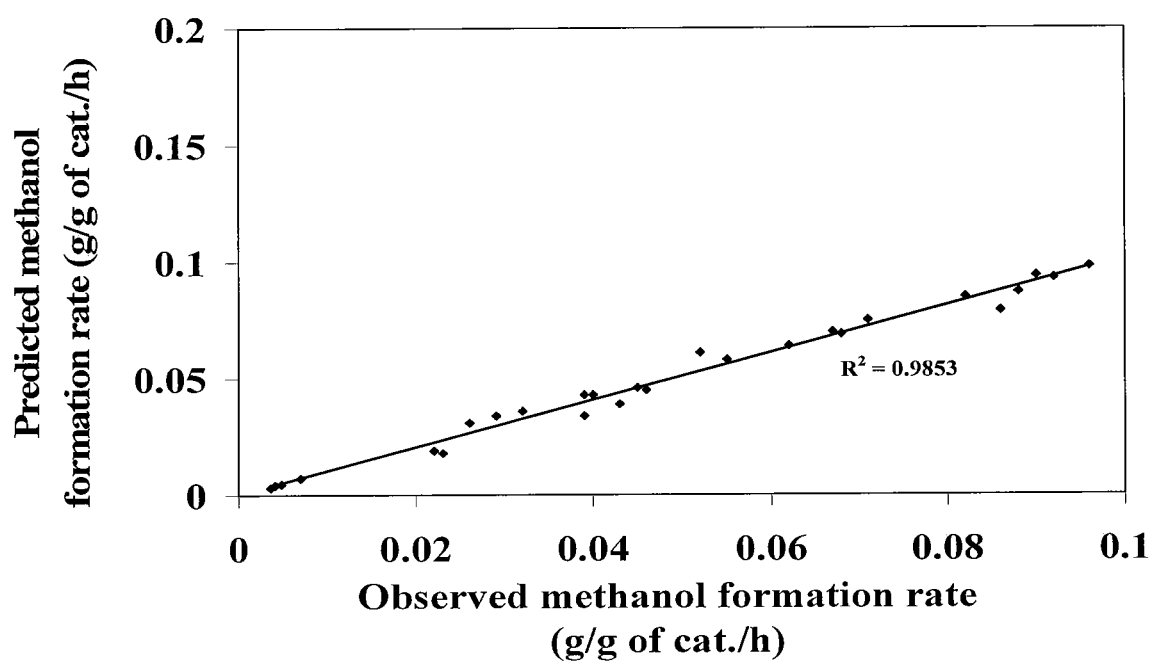
FIG. 35 shows comparison plots for observed methanol formation rate for an exemplary K-promoted Co—Rh—Mo/MWCNT catalyst.
Figure 36:
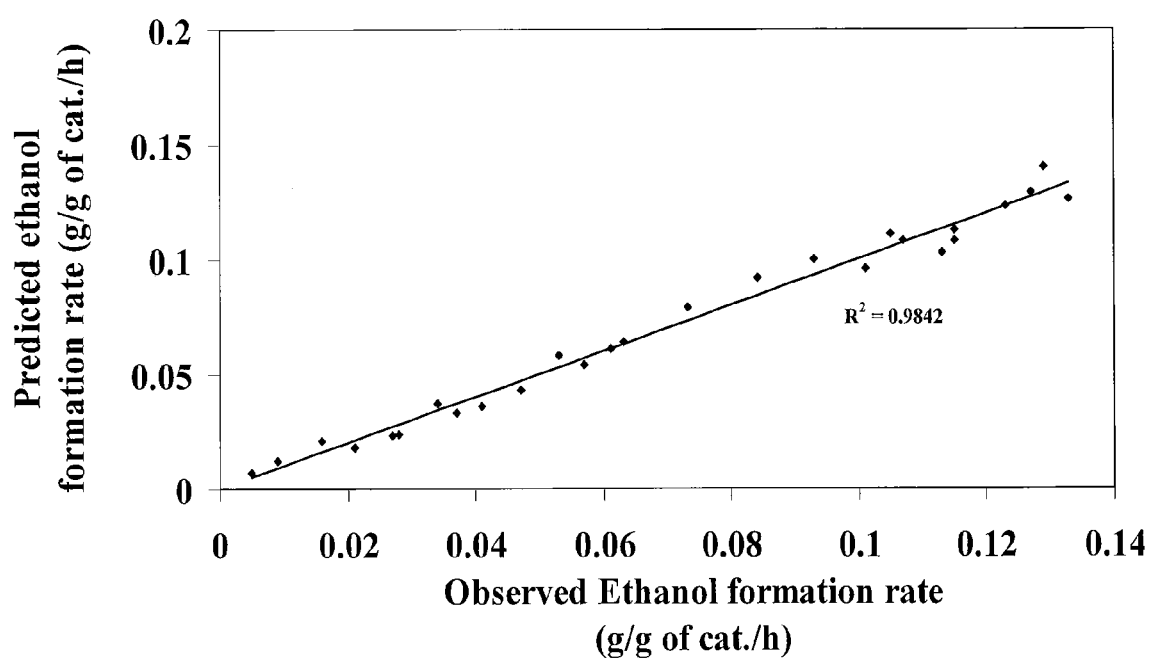
FIG. 36 shows comparison plots for observed ethanol formation rate for an exemplary K-promoted Co—Rh—Mo/MWCNT catalyst.
Figure 37:
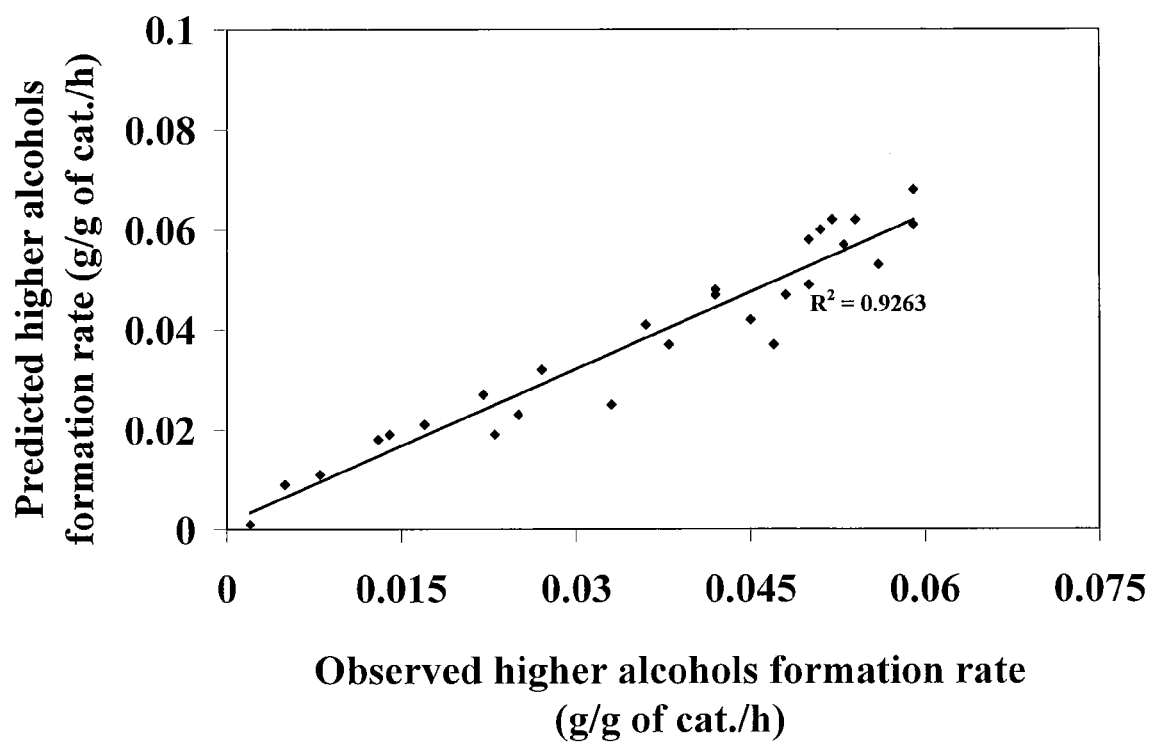
FIG. 37 shows comparison plots for observed higher alcohols formation rate for an exemplary K-promoted Co—Rh—Mo/MWCNT catalysts
Figure 38:
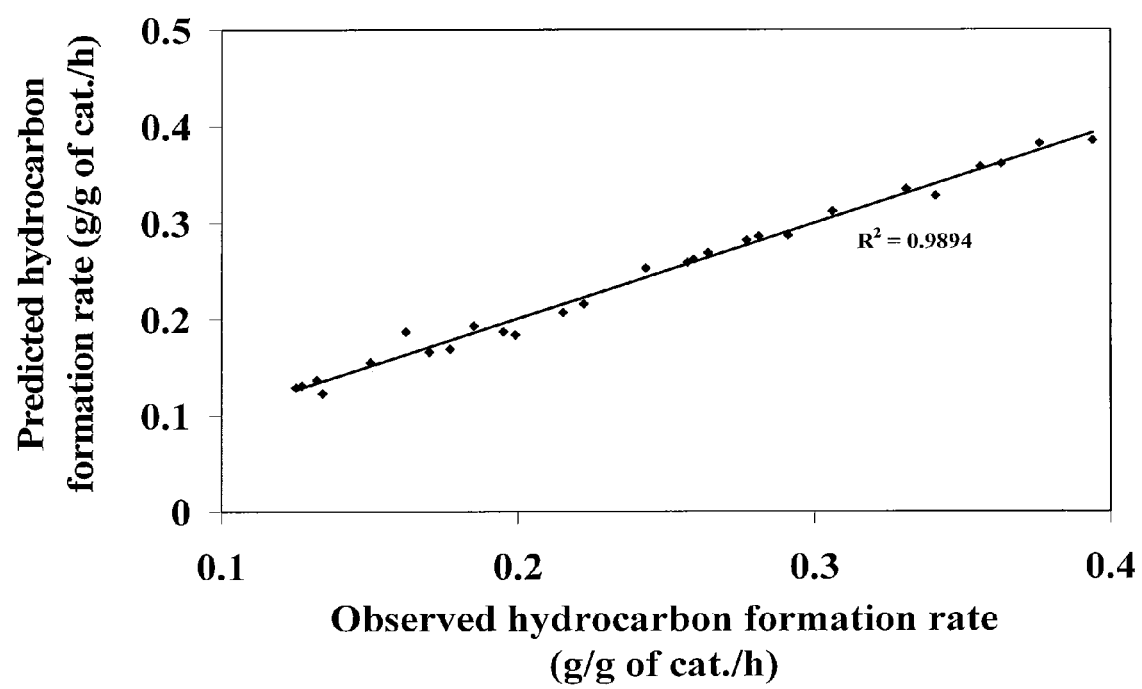
FIG. 38 shows comparison plots for observed hydrocarbons formation rate for an exemplary K-promoted Co—Rh—Mo/MWCNT catalyst.
Figure 39:
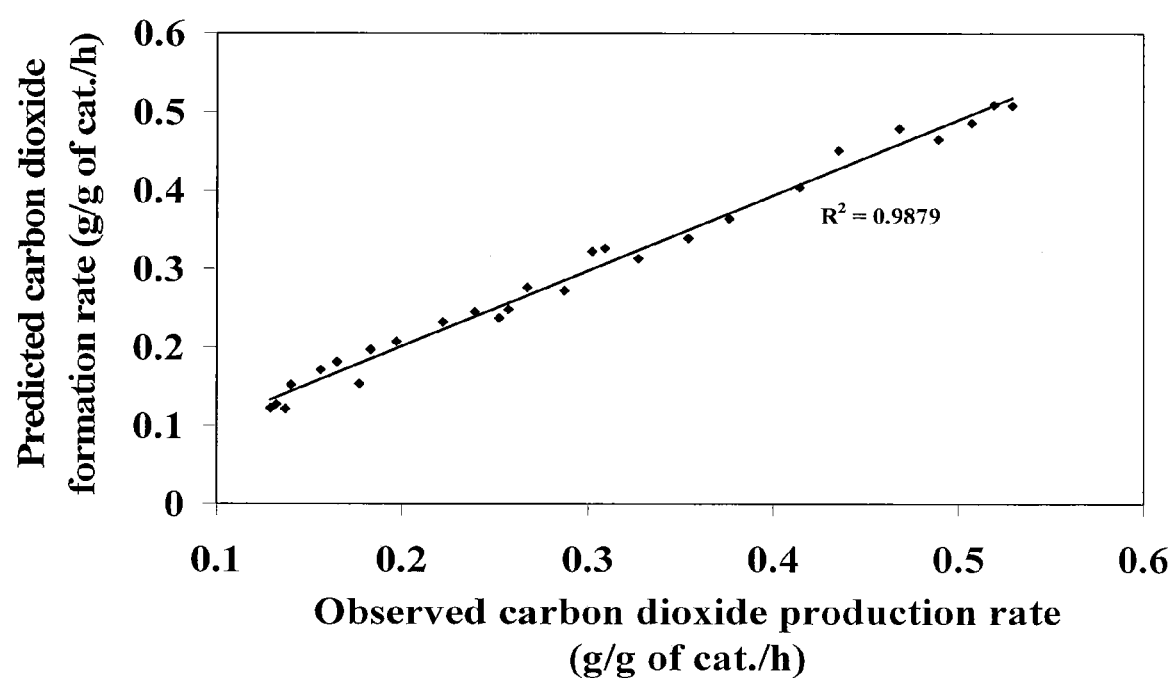
FIG. 39 shows comparison plots for observed carbon dioxide formation rate for an exemplary K-promoted Co—Rh—Mo/MWCNT catalyst.

The effect of the feed gas flow rate on external mass-transfer diffusion was studied by performing the experiments at an inlet temperature of 325° C., pressure of 1320 psig (9.1 MPa), and $H_2$ to CO molar ratio of 1.25 using 2 g of catalyst with average particle size of 0.179 mm. The variation in % CO conversion with flow rate is given in FIG. 34. It is expected that, in the case of existing external mass-transfer resistance, the boundary layer thickness becomes reduced with an increased flow rate and results in the enhanced CO conversion at higher flow rates. From FIG. 34, it is observed that the % CO conversion decreased monotonically from 52 to 42% with an increased flow rate from 80 to 120 ml/min, which resulted because of the short contact time between the reactants at high flow rates. $k_c$ and δ values were calculated for different flow rates, and the results are given in Table 17. It is clear from this table that the flow rate has a negligible effect on external mass-transfer diffusion under the investigated operating conditions using the sample pellets of average particle diameter of 0.179 mm.

(b) Internal Mass-Transfer Diffusion

The Weisz-Prater criterion ($C_{WP}$) is used to estimate the internal mass-transfer resistance in heterogeneous catalytic reactions.[18] If $C_{WP} \ll 1$, there is no internal diffusion limitation, and if $C_{WP} \gg 1$, internal diffusion limits the reaction severely.[78] This criterion is given as follows:

$$C_{WP} = \frac{-(r'_A)_{obs} * \rho_C * R^2}{D_e * C_{A_s}} \quad (5)$$

where $(r'_A)_{obs}$ is the reaction rate per unit mass of catalyst, $\rho_c$ is the catalyst density, R is the particle radius, $C_{A^s}$ is the surface concentration of reactant A, and $D_e$ is the effective diffusivity.

The value of $C_{WP}$ was calculated for the catalysts with average particle diameter of 0.179 mm at 300° C. The $C_{WP}$ value of this parameter was obtained as 0.007, which is far less than 1. This confirms that internal diffusion limitation is negligible on the catalyst with the average particle diameter of 0.179 mm.

(c) Intrinsic Kinetics

The analysis of liquid products indicates that the alcohols likely followed the CO insertion mechanism, forming linear alcohols. Methanol, ethanol, n-propanol, and n-butanol are the major products together with other higher alcohols. Very little water (<1% by weight) was found in the liquid product, and hence, the concentration of water was neglected. The analysis of exit gas indicates that methane is the major hydrocarbon component apart from $CO_2$ as well as unconverted CO and $H_2$.

The reaction scheme suggested by Santiesteban et al.[9] for the production of alcohols from synthesis gas over $MoS_2$ catalysts was used to determine the intrinsic reaction kinetics.

It is difficult to obtain a statistically valid model for such an extremely complex reaction scheme; hence, the simplified reaction scheme was assumed. The liquid and gas streams were simplified into a selected number of components, namely, CO, $H_2$, $CO_2$, methanol, and ethanol, as well as pseudo-components, Hyd that represents methane and higher hydrocarbons, and $HA_{C3+}$ that represents higher alcohols (alcohols with carbon number greater than 2). All the reactions were assumed to be stoichiometric, and the simplified reaction scheme is as shown below[81]:

$$CO+2H_2 \leftrightarrow CH_3OH \quad (6)$$

$$2CH_3OH \rightarrow C_2H_5OH+H_2O \quad (7)$$

$$(N_{HA}-2)CH_3OH+C_2H_5OH \rightarrow HA_{C3+}+(N_{HA}-2)H_2O \quad (8)$$

$$N_{HC}CO+(2N_{HC}+1)H_2 \rightarrow Hyd+N_{HC}H_2O \quad (9)$$

$$CO+H_2O \leftrightarrow CO_2+H_2 \quad (10)$$

where $N_{HA}$ and $N_{HC}$ stand for the average carbon atom number of the pseudo-components $HA_{C3+}$ and Hyd, respectively.

In the above reaction scheme, the formation of methanol and hydrocarbons are obtained directly from CO and $H_2$. It is assumed that hydrocarbon products are composed exclusively of methane. Methanol formation and the water-gas shift (WGS) reaction are assumed to be in thermodynamic equilibrium, and other reactions are assumed to be irreversible.[82] The formation of ethanol and higher alcohols were assumed to follow stepwise chain growth alcohols by taking methanol as the recurrent $C_1$ reactant; that is, one mole of ethanol is produced from two moles of methanol and one mole of propanol is obtained from one mole of methanol and one mole of ethanol, etc. The present reaction scheme is similar to the lumped kinetic model, which accounts for the global formation of higher oxygenates suggested by Tronconi et al.[83]

The power law model was used for the reaction between CO and $H_2$ on the catalyst surface, because this model is simple and widely used to predict the reaction rate for the higher alcohols synthesis reaction.[84,85] A reversible kinetic expression was used for the methanol synthesis and the WGS reaction. Ideal gas behaviour was assumed with WGS reaction, whereas the non-ideal behavior of methanol was considered.[89] Ethanol, higher alcohols, and hydrocarbon formations were represented using irreversible kinetic expressions.

The plug-flow reactor was used in the kinetic study of the higher alcohols synthesis reaction over the alkali-promoted trimetallic Co—Rh—Mo catalyst supported on MWCNTs. As discussed in the previous section, the catalyst particle size in the range of 147-210 μm was selected to eliminate the external and internal mass-transfer resistances and the reactor was regarded as isothermal. Differential mole balance equations were used and were solved by using ode45 routines in MATLAB, and, simultaneously, the sum of the squares function was minimized by using fminsearch. The kinetic parameters were estimated by fitting the experimental data in the sum of the squares function and minimizing the errors. The residual error values obtained at 275, 300, 325, and 350° C. are 0.0954, 0.0335, 0.0874, and 0.0395, respectively. Arrhenius plots are drawn for obtaining activation energies and frequency factors from the kinetic parameters, and the values shown in Table 18. FIGS. 35 to 39 show the fit between observed values and the predicted model values of methanol, ethanol, higher alcohols, hydrocarbons, and carbon dioxide, respectively. The $R^2$ values by the models show a good fit with the experimental results.

It was observed that the CO conversion, hydrocarbon formation rate, and the WGS reaction rate increased monotonically with an increased temperature, whereas, methanol formation decreased monotonically with an increased temperature from 275 to 350° C. A maxima is observed in ethanol and higher alcohols formation at 330° C. As shown in Table 16, the activation energy of hydrocarbons and carbon dioxide were higher than that of the alcohols. This is because the hydrocarbon formation rate and the water gas shift reaction rate both increased at higher temperatures. The activation energy of alcohols is observed in the following order: methanol<ethanol<higher alcohols. This explains that an increasing temperature favors the conversion of lower molecular-weight alcohols to higher alcohols. Christensen et al.[85] explained that an increased temperature favors the high CO surface coverage on the catalyst which favors the improved rate of the CO insertion step and yields chain growth. This is an uncommon behavior for such chain growth reactions.

Table 19 compares the activation energies for methanol, ethanol, higher alcohols, and hydrocarbons obtained over the alkali-promoted trimetallic Co—Rh—Mo catalyst supported on MWCNTs to those of values from available literature. The increase in activation energy with the alcohol carbon number was in agreement with the literature.[85] The activation energies of ethanol and higher alcohols obtained over the Co—Rh—Mo—K/MWCNT catalyst were low compared to those values reported in the literature. Low activation energies of alcohols might be possible because of the structural modification of Mo species with the promotion of K, Co, and Rh, which favor the formation of small particles uniformly dispersed inside and outside the straight pores of the MWCNTs support. This explains that the Co—Rh—Mo—K/MWCNT catalyst performance is better compared to that of the catalysts that have been studies so far and are available in the open literature.

Example 6

Deactivation Studies of Alkali-Modified Trimetallic Co—Rh—Mo Sulfided Catalysts for Higher Alcohols Synthesis from Synthesis Gas Materials and Methods
(a) Preparation of Catalysts Both commercial catalyst supports, MWCNTs (M.K. Nano, surface area-178 $m^2/g$ and pore volume-0.54 cc/g) and activated carbon (Aldrich, surface area-655 $m^2/g$ and pore volume-0.93 cc/g), were treated with 30% $HNO_3$ reflux at 100° C. overnight and washed with distilled water several times, followed by drying at 120° C. for 6 h. The support, MWCNTs has a surface area of 220 $m^2/g$ and pore volume of 0.66 cc/g, whereas, the activated carbon support exhibits a surface area of 676 $m^2/g$ and pore volume of 0.97 cc/g. Ammonium heptamolybdate tetrahydrate (AHM), potassium carbonate, cobalt acetate tetrahydrate, and rhodium chloride hydrate were used as precursors for Mo, K, Co, and Rh, respectively. The catalysts were prepared by conventional incipient wetness method, as described in the previous Examples.

(b) Characterization of Fresh and Spent Catalysts

The morphology of both the fresh and spent catalysts was characterized by transmission electron microscopy (TEM) investigations, using a Philips CM20 (100 kV) transmission electron microscope equipped with a NARON energy-dispersive spectrometer with a germanium detector.

The content of Mo, Co, and Rh of the oxide catalysts were determined using a Perkin-Elmer ELAN 5000 inductively coupled plasma mass spectroscopy (ICP-MS) instrument.

The surface area, pore volume, and average pore diameter of fresh catalysts in oxide and sulfide forms, as well as the spent catalysts were measured by $N_2$-physisorption at 77 K using a Micromeritics ASAP 2000. Approximately 0.2 g of sample was used for each analysis. The moisture and other adsorbed gases present in the sample were removed before analysis by degassing the sample at 200° C. for 2 h under 66.7 Pa (500 mm Hg). The sample was then evacuated at 2.67 Pa (20 μm Hg) before $N_2$ adsorption.

The carbon monoxide uptake on the fresh and used catalysts was measured using the Micromeritics ASAP 2000 instrument. Prior to the CO chemisorption measurement 0.2 g of sample was sulfided in situ, using 10 mole % $H_2S$ in $H_2$ at 400° C. for 4 h. The sample was then evacuated at 120° C. until the static pressure remained less than $6.6 \times 10^{-4}$ Pa. Chemisorption was performed by passing pulses of CO over the sample to measure the total gas uptake at 35° C. The CO uptake (μmole/g of cat.) measured from CO chemisorption is equivalent to the number of active metal atoms that are accessible to the reactant molecules. The stoichiometric coefficient (CO to metal ratio) of 1 was used, and the extent of reduction was assumed to be 100% in metal dispersion calculations.

Powder X-ray diffraction (XRD) analysis patterns of oxide and sulfide forms of both the fresh and spent catalysts were recorded on a Rigaku X-ray diffraction instrument with nickel filtered Cu Kα radiation (λ=0.1541 nm). Each sample was scanned at a rate of 0.05°/s, with 2θ varying from 10 to 80°. To obtain the XRD patterns in sulfided form, the catalysts were first sulfided for 6 h at 450° C., at a heating rate of 2° C./min using a gaseous mixture containing 10 mole % $H_2S$ in $H_2$ at a flow rate of 50 ml/min. After sulfidation, the catalysts were cooled to room temperature in a flow of He and the sample was transferred to sample holders under protection of He.

To study the reducibility of the fresh and spent catalysts, temperature programmed reduction (TPR) profiles of the catalysts were performed. For each analysis, approximately 0.2 g of sample was used, which was first purged in 50 cm$^3$ (STP)/min flow of He at 170° C. to remove traces of water, and then cooled to 40° C. The TPR of each sample was performed using a 10 mole % $H_2$ in Ar stream at a flow rate of 50 cm$^3$ (STP)/min and a heating ramp rate of 10° C./min from 40° C. to 650° C. Hydrogen consumption was monitored by a thermal conductivity detector (TCD) attached to a Micromeritics AutoChem II chemisorption analyzer. During the analysis the effluent gas was passed through a cold trap placed before the TCD in order to remove water from the exit stream of the reactor.

The amount of carbon deposition after 720 h of continuous higher alcohols synthesis was analyzed by performing thermogravimetric analysis (TGA) of fresh and spent catalyst using a Perkin-Elmer thermogravimetric (TG) differential thermal analyzer (DTA) under air flow of 40 ml/min. The samples were heated in a platinum sample holder from room temperature to 600° C. with a heating rate of 5° C./min.

(c) Catalytic Durability Studies

The catalytic durability studies for conversion of synthesis gas to higher alcohols were performed using the feed gas mixture CO (40 mole %), $H_2$ (50 mole %), and Ar (10 mole %) in a single-pass tubular downflow fixed-bed reactor under the reaction conditions of 330° C., 9.1 MPa (1320 psig), and 3.8 m$^3$ (STP)/(kg of cat.)/h over a period of 720 h. The detailed description about the high pressure reaction set up used in this study is as discussed in the previous examples. Prior to the reaction, the catalyst was reduced and sulfided, for 6 h at 450° C. at a heating rate of 2° C./min using a gas mixture containing 10 mole % $H_2S$ in $H_2$ at a flow rate of 50 ml/min. The product gas was separated into gas and liquid phases inside the condensers at 0° C. and reaction pressure. The liquid products were collected from the cold traps every 12 h during the first 2 days and then obtained after every 24 h. The sulfur content of the liquid product obtained at different time intervals was measured using the combustion-fluorescence technique of the ASTM 5463 method. The instrumental error for S analysis was approximately ±3%, based on analyzing standard solutions of known composition. The liquid products were analyzed with a Varian 3400 gas chromatograph equipped with a capillary column and a flame ionization detector (FID). The gaseous products were analyzed online on a Shimadzu gas chromatograph through a sampling valve for every 1 h. The results obtained were within the experimental error of ±2.5%.

After 720 h of the higher alcohols synthesis, the flow of synthesis gas was switched off, and the catalyst was re-sulfided and reduced in a flow rate of 50 ml/min of 10 mole % $H_2S$ in $H_2$ at 450° C. for 6 h. The higher alcohols synthesis was again carried out under the same conditions, as discussed above for 24 h. The temperature of the reactor was lowered to room temperature and the catalytic bed was treated by helium flow for 3 h at room temperature to washout the $H_2S$ and synthesis gas present inside the reactor. The catalyst was then passivated with pulses of dry air to stop further oxidation. The spent catalyst was removed from the reactor and characterized extensively.

Results and Discussion (a) Characterization of Fresh and Spent Catalysts

TEM images of the fresh and spent alkali-modified trimetallic Co—Rh—Mo catalysts supported on MWCNTs were recorded and shown as FIGS. 40*a* and 40*b*, respectively. The tubular morphology of the grapheme layers make MWCNTs a different support compared to activated carbon. The TEM image of the fresh MWCNT-supported catalyst (FIG. 40*a*) revealed that the metal species are well dispersed both inside the carbon nanotubes and on the outside of the tube walls in the particle size range of 1 to 5 nm. FIG. 40*b* shows that sintering occurs on the particles located on the outer surface of the MWCNTs, whereas the size of the particles inside the tubes is almost similar to that of the fresh catalyst. The π-electron density creates a deviation in the concave inner and convex outer surface of the graphite layers, leading to an electron-deficient interior and an electron-enriched exterior surface.[86] This results in a strong interaction of metal species with the support on the particles located on the inner surface of the MWCNTs, compared to their outer layers. The little or no mobility of the particles inside the tubes prevents the occurrence of sintering.[87]

FIGS. 41*a* and 41*b* show the TEM images of fresh and spent Co—Rh—Mo—K catalysts supported on activated carbon. Some of the metal species are inside the pores and a considerable amount of agglomerates are formed on the surface of the microporous activated carbon support (FIG. 41*a*). The TEM image of the spent catalyst (FIG. 41*b*) shows the formation of large agglomerates, resulting from the large sintering rate of metal species on the catalyst. Iranmahboob et al.[36] explained that agglomeration of cobalt and sulfur takes place after exposure to synthesis gas on the catalyst surface, leading to the formation of square-like planes of cubic crystallites ($Co_9S_8$). These results confirm that the agglomeration of catalytic species is high on the activated carbon support compared to that of MWCNTs.

Table 20 presents the Co, Rh, and Mo contents of the fresh and spent catalysts measured by ICP-MS, along with the targeted compositions. Due to the hygroscopic nature of precursors, the measured contents of the catalysts are slightly low compared to targeted values. Deviation in the targeted and measured metal contents is high over the activated carbon-based catalysts compared to the MWCNT-supported catalysts, indicating that the concentration of metal particles is not uniform on this support. ICP analyses revealed that the metal content of the spent catalysts was close to that of the fresh catalysts.

Results of the textural characteristics such as surface area, total pore volume, and average pore diameter obtained over the fresh, sulfided, and spent catalysts are given in Table 20. The MWCNT-supported alkali-promoted trimetallic Co—Rh—Mo catalyst showed a BET surface area of 68 m$^2$/g and a total pore volume of 0.24 cm$^3$/g. Upon sulfidation of this catalyst, the BET surface area and pore volume increased to 79 m$^2$/g and 0.29 cm$^3$/g, respectively. After 720 h of higher alcohols synthesis, both the catalyst BET surface area and pore volume decreased to 71 m$^2$/g and 0.26 cm$^3$/g, respectively. After impregnating the metal species, a drastic fall in surface area was observed over the activated carbon-supported catalyst. The activated carbon-supported alkali-promoted trimetallic catalyst showed a BET surface area and pore volume of 97 m$^2$/g and 0.16 cm$^3$/g, respectively. These results suggest that pore blocking of the activated carbon by the metal species is high compared to that of MWCNTs, due to the microporous nature of the activated carbon support.

Similar to the MWCNT-supported catalyst, sulfidation of the activated carbon-supported Co—Rh—Mo—K catalyst improved both the BET surface area and pore volume. Sulfidation causes reduction in particle size of the metal species that decreases the blocking extent of the support, resulting in improved BET surface area and pore volume. After 720 h over the spent activated carbon-supported catalyst, a BET surface area of 85 m$^2$/g and pore volume of 0.10 cm$^3$/g were observed. From these results, it is clear that sintering of the metal species and pore blockage due to coke deposition during higher alcohols synthesis is high on the activated carbon-supported catalyst, causing a large decrease in both BET surface area and pore volume, compared to that of the MWCNT-supported catalyst.

Table 20 also gives the results of the CO chemisorption measurements. The CO uptake on the fresh alkali-modified Co—Rh—Mo trimetallic catalysts supported on MWCNTs and activated carbon was 237 and 137 µmole/(g of cat.), respectively. The MWCNT-supported catalyst outperformed the activated carbon-supported catalyst, confirming that the support plays an important role on CO hydrogenation capability. Metal dispersions observed on the alkali-modified trimetallic catalysts supported on MWCNTs and activated carbon were 48% and 28%, respectively. MWCNTs have the advantage of well-defined hollow interiors and uniform straight pores with a large pore size, providing uniform distribution of metal species to obtain high dispersion on the support. The CO uptake value and metal dispersion for the spent catalyst supported on MWCNTs are slightly lower (7% and 6%, respectively) than that of the fresh catalyst. The spent catalyst supported on activated carbon was found to be 43% less in both CO uptake value and dispersion of metal species compared to that of the fresh catalyst. As mentioned earlier, sintering of metal species and pore blockage due to coke deposition might be responsible for low metal dispersions of the spent catalyst supported on activated carbon.

Figure 42:
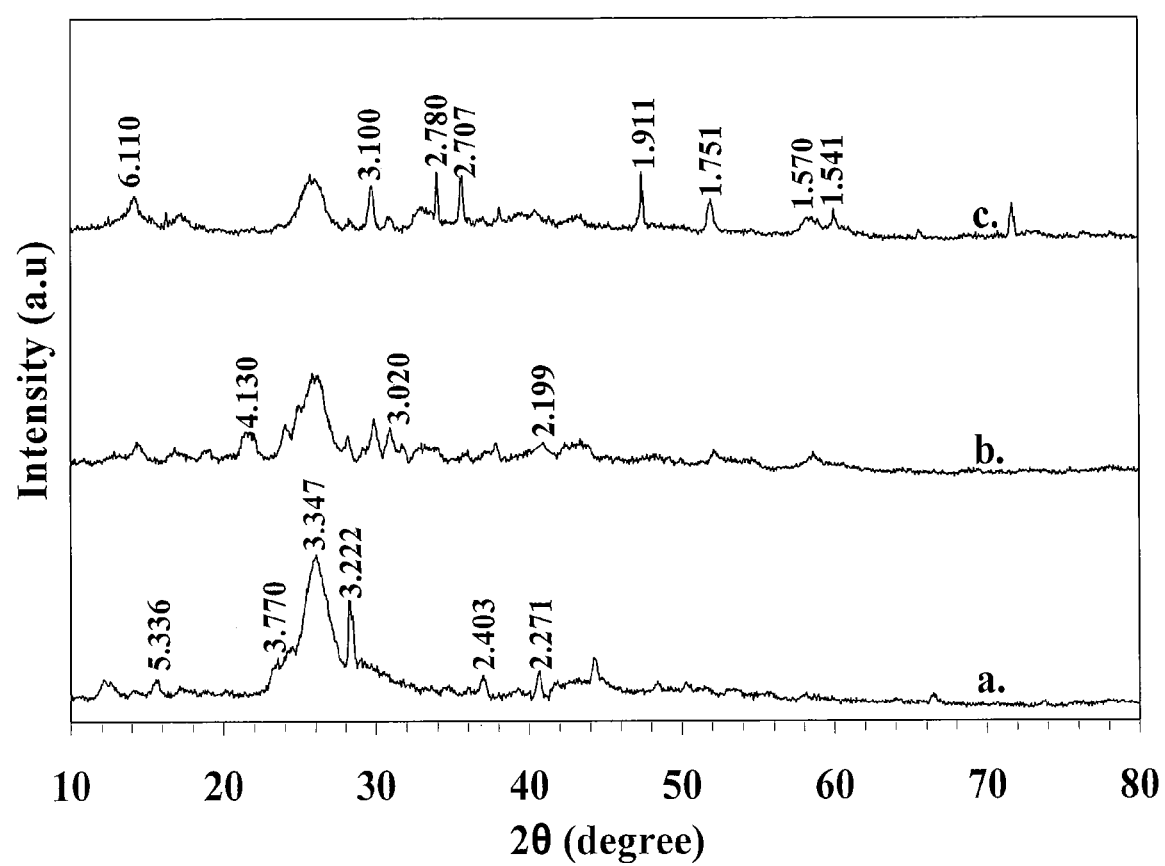
FIG. 42 shows XRD patterns of an exemplary MWCNT-supported catalyst; a. Fresh catalyst, b. Sulfided catalyst, c. Spent catalyst.
Figure 43:
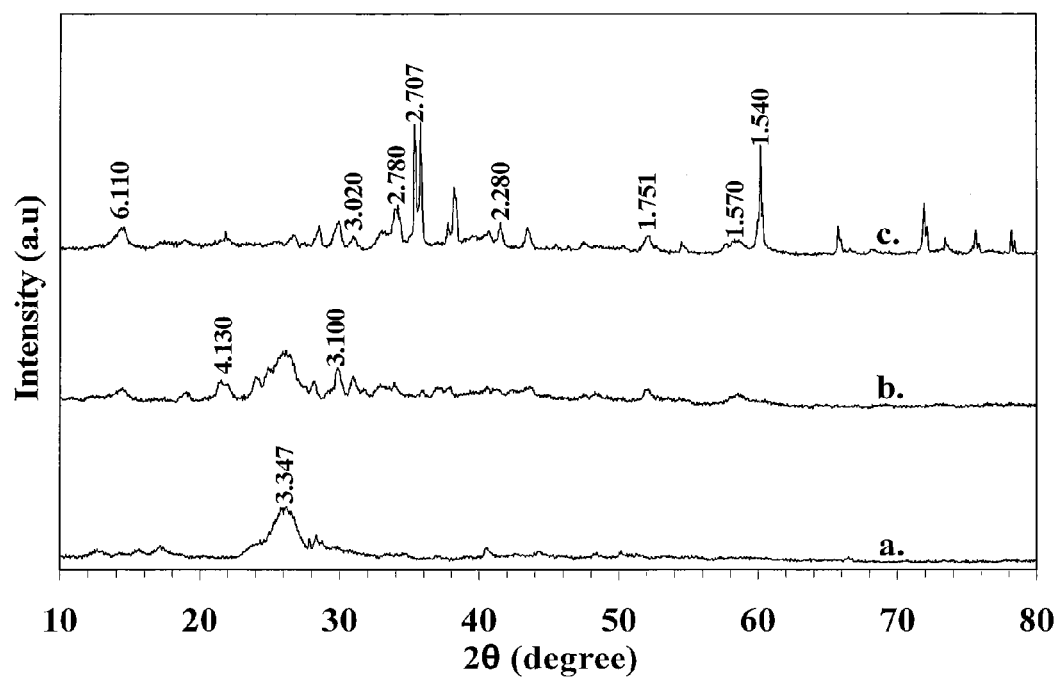
FIG. 43 shows XRD patterns of an exemplary activated carbon-supported catalyst; a. Fresh catalyst, b. Sulfided catalyst, c. Spent catalyst.

FIGS. 42 and 43 show the XRD patterns of the MWCNTs and activated carbon-supported alkali-modified trimetallic Co—Rh—Mo catalysts measured in oxidized and sulfided form, together with the spent catalysts after 720 h of higher alcohols synthesis. The JCPDS chemical spectra data bank was used to detect the most probable phases present in the samples, and the results of the possible crystal phases with their corresponding reflection planes are given in Table 19. The reflections of the graphite phase are observed at d spacing of 3.347 in both the MWCNTs and activated carbon supports.[88] The characteristic reflections corresponding to the crystalline structure of MoO$_3$ are observed at 2θ value of 40.2° in the XRD patterns of the oxidized form of catalysts supported on MWCNTs and activated carbon.[89] Peaks corresponding to the characteristic reflections of different K—Mo—O phases, such as KMo$_4$O$_6$ (d-spacing of 5.366 and 2.403), K$_2$Mo$_7$O$_{20}$ (d-spacing of 3.770), and K$_2$Mo$_2$O$_7$ (d-spacing of 3.222) are also observed.[90,91,92]

The formation of MoS$_2$ crystallites are observed at d-spacing of 6.110, 2.707, 2.199, and 1.570 in the XRD pattern of the sulfided catalysts (FIGS. 42b and 43b). The characteristic reflections of the K—Mo—S species are observed at d-spacing of 3.100, 3.020, and 2.780. The peak corresponding to the characteristic of bulk Co$_9$S$_8$ particles is observed at d-spacing of 1.751. XRD patterns of the spent catalysts supported on MWCNTs and activated carbon are shown in FIGS. 42c and 43c, respectively. There is no significant change in the intensity of the peaks corresponding to the K—Mo—S mixed phases, but increased peak intensities of the MoS$_2$ and Co$_9$S$_8$ phases were observed. These results confirm that sintering of metal sulfide crystallites such as MoS$_2$ and Co$_9$S$_8$ takes place upon exposure to the synthesis gas, leading to the agglomeration of these species on the support. Compared to the MWCNT-supported spent catalyst (FIG. 42c), a significant increase in peak intensity for the MoS$_2$ and Co$_9$S$_8$ species is noted in the spent catalyst supported on activated carbon (FIG. 43c), indicating that particle size increased with time on stream for 720 h. This may be due to the sintering of metallic particles during the reaction, as a result of the poor interaction between metal particles and the support.

Figure 44:
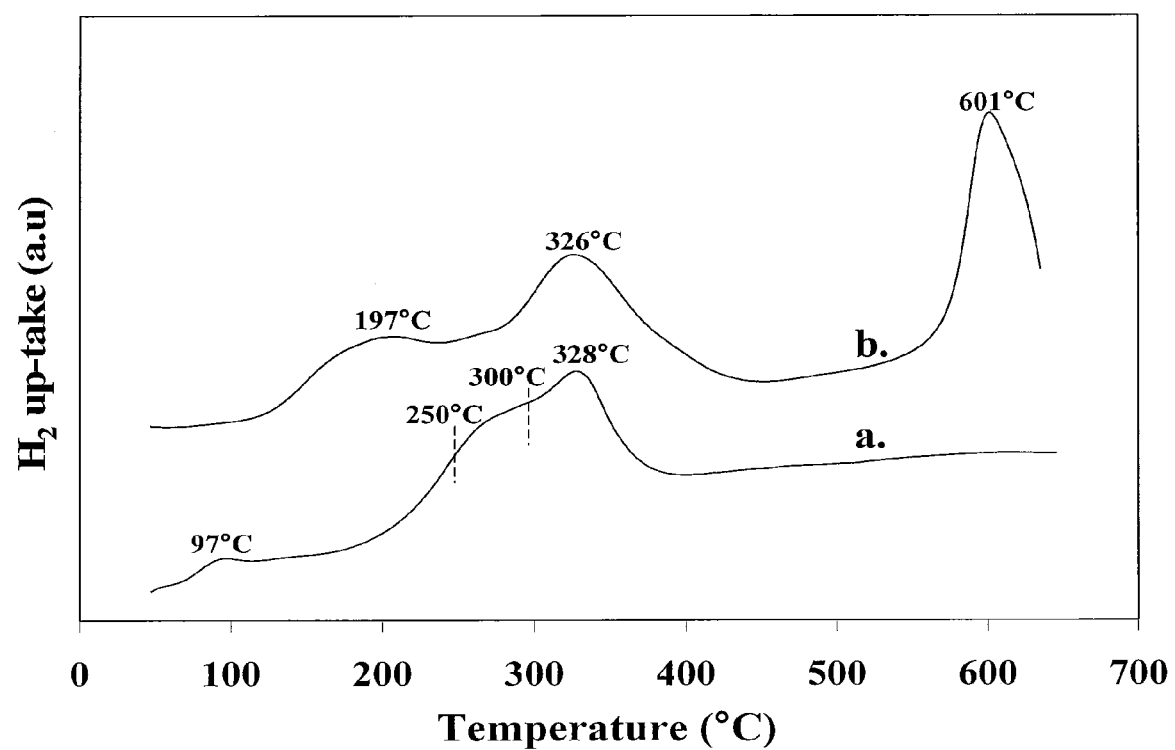
FIG. 44 shows $H_2$-TPR profiles of an exemplary MWCNT-supported catalyst; a. Fresh catalyst, b. Spent catalyst.
Figure 45:
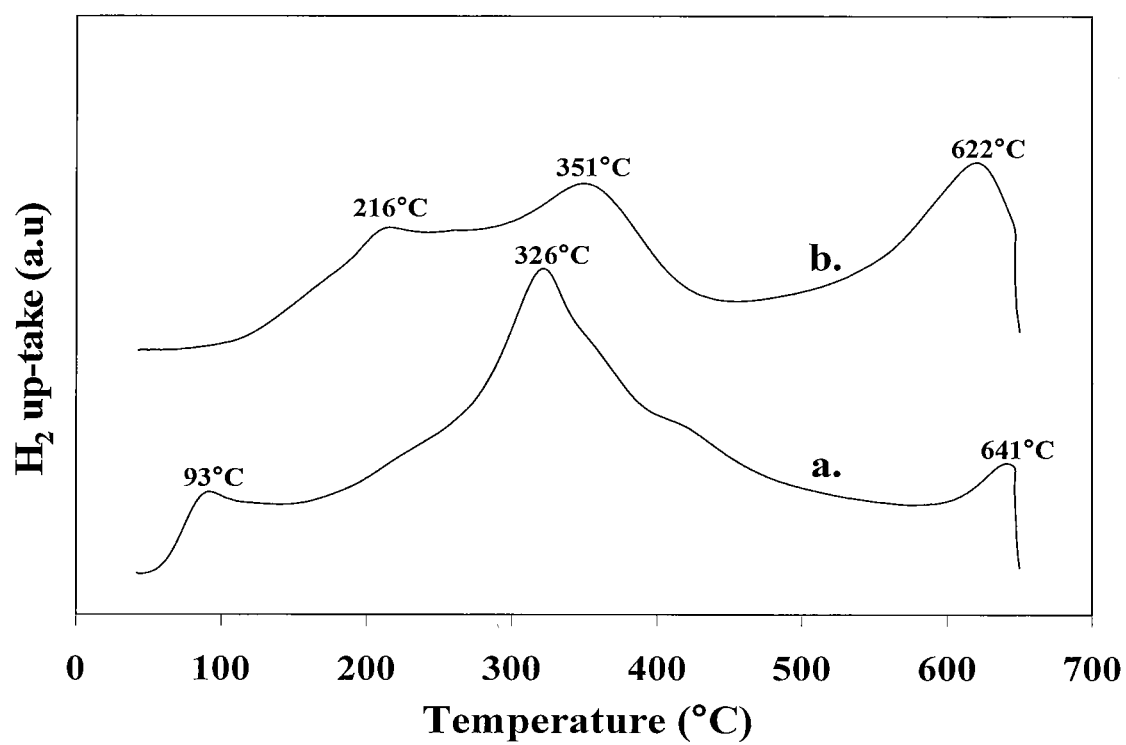
FIG. 45 shows $H_2$-TPR profiles of an exemplary activated carbon-supported catalyst; a. Fresh catalyst, b. Spent catalyst.

The activation of the fresh and spent alkali-modified trimetallic Co—Rh—Mo catalysts supported on MWCNTs and activated carbon in a hydrogen atmosphere was proven by TPR experiments and shown in FIGS. 44 and 45, respectively. The H$_2$-TPR studies of the fresh catalyst supported on MWCNTs (FIG. 44a) reveal the main reduction peak at 328° C., due to the complete reduction of bulk MoO$_3$ species to lower oxidation state. A shoulder peak in the temperature range 250-300° C. is due to the reduction of bulk CoO$_3$-related species. A small peak attributed to the reduction of Rh species is noted in the temperature range 97° C. Over the spent catalyst supported on MWCNTs (FIG. 44b), the reduction of Mo species took place in two different steps; first the reduction of octahedral coordinated Mo (Mo$^{+6}$) species to tetrahedral coordinated Mo (Mo$^{+4}$) species occurs at 326° C., followed by the reduction of Mo$^{+4}$ species to a lower oxidation state at 601° C. The peak corresponding to the reduction of Co species shifted to a lower temperature of 197° C., indicating that the easier reduction of the cobalt occurred in the spent catalyst compared to the fresh. The easier reduction of Co species can be explained by the formation larger particles on the outer surface of the nanotubes, which is evident from TEM image of the spent catalyst supported on MWCNTs (FIG. 40b). No peaks corresponding to the reduction of Rh species were present, indicating that Rh exists in completely reduced form over the spent catalyst. These results coupled with the XRD pattern (FIG. 42c) confirm that the sintering of Co species is high after exposure of synthesis gas on the catalyst surface, whereas the Mo and Rh species are quite stable with little or no sintering over the alkali-promoted trimetallic Co—Rh—Mo catalyst supported on MWCNTs.

Two main reduction peaks are observed in the TPR studies of the fresh activated carbon-supported alkali-modified trimetallic Co—Rh—Mo catalyst (FIG. 45a), with the low temperature reduction peak appearing around 321° C. and the high temperature peak around 640° C. No peak is observed representing the reduction of Co species, but the small peak at 94° C. represents the reduction of Rh species. The peak representing the reduction of $Mo^{+6}$ to $Mo^{+4}$ oxidation state shifted to higher temperatures over the spent catalyst supported on activated carbon (FIG. 45b). These results indicate that the interaction of Mo species occurred with the activated carbon support after the catalyst was exposed to synthesis gas. Compared to the fresh catalyst, an extra peak was observed at 216° C. representing the presence of Co species over the spent catalyst supported on activated carbon. As seen from the TEM image (FIG. 41b) and XRD patterns (FIG. 43c) of the spent catalyst, agglomeration of metal species were found to be high on the surface of activated carbon, due to the sintering of active phases.

Figure 46:
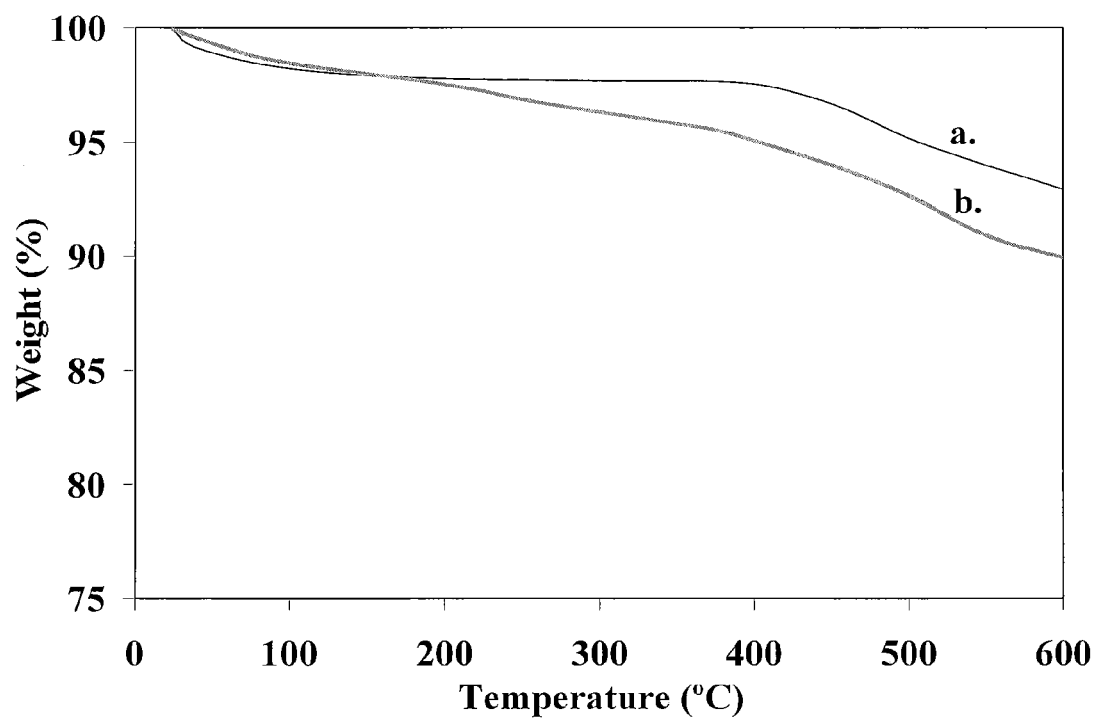
FIG. 46 shows TG profiles of an exemplary MWCNT-supported catalyst; a. Fresh catalyst, b. Spent catalyst.
Figure 47:
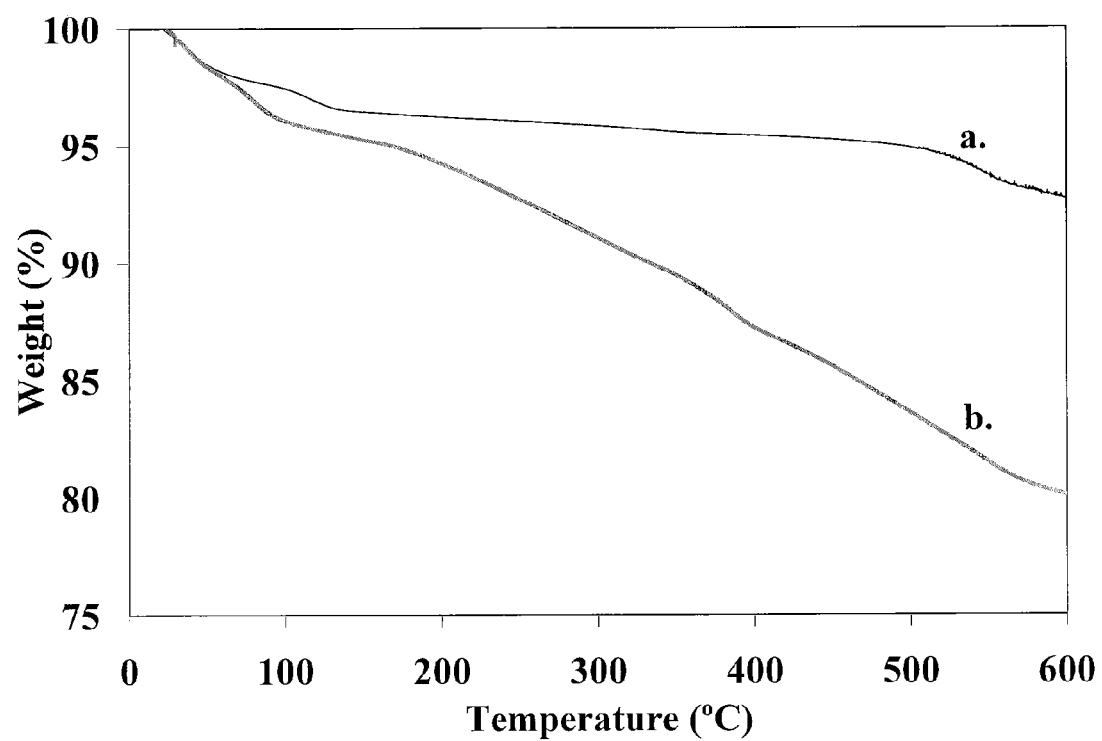
FIG. 47 shows TG profiles of an exemplary activated carbon-supported catalyst; a. Fresh catalyst, b. Spent catalyst.

The thermo-gravimetric (TG) profiles of the temperature-programmed oxidation (TPO) in air of the fresh and spent catalysts supported on MWCNTs are shown in FIG. 46. The slight weight loss over the catalysts occurring at around 100° C. was probably resulted from the evaporation of moisture. The weight loss over the MWCNT-supported spent catalyst (FIG. 46b) in the range of 100 to 400° C. might be due to the oxidization of S species. However, the carbon deposits were oxidized at around 450-600° C. (FIGS. 46a and 46b). The TG profiles of the fresh and spent catalysts supported on activated carbon revealed that activated carbon support is more susceptible to coke formation and deactivation (FIGS. 47a and 47b). These result confirmed that coke deposition is high on the activated carbon-supported catalyst compared to that of the catalyst supported on MWCNTs.

Catalytic Durability Studies

Figure 48:
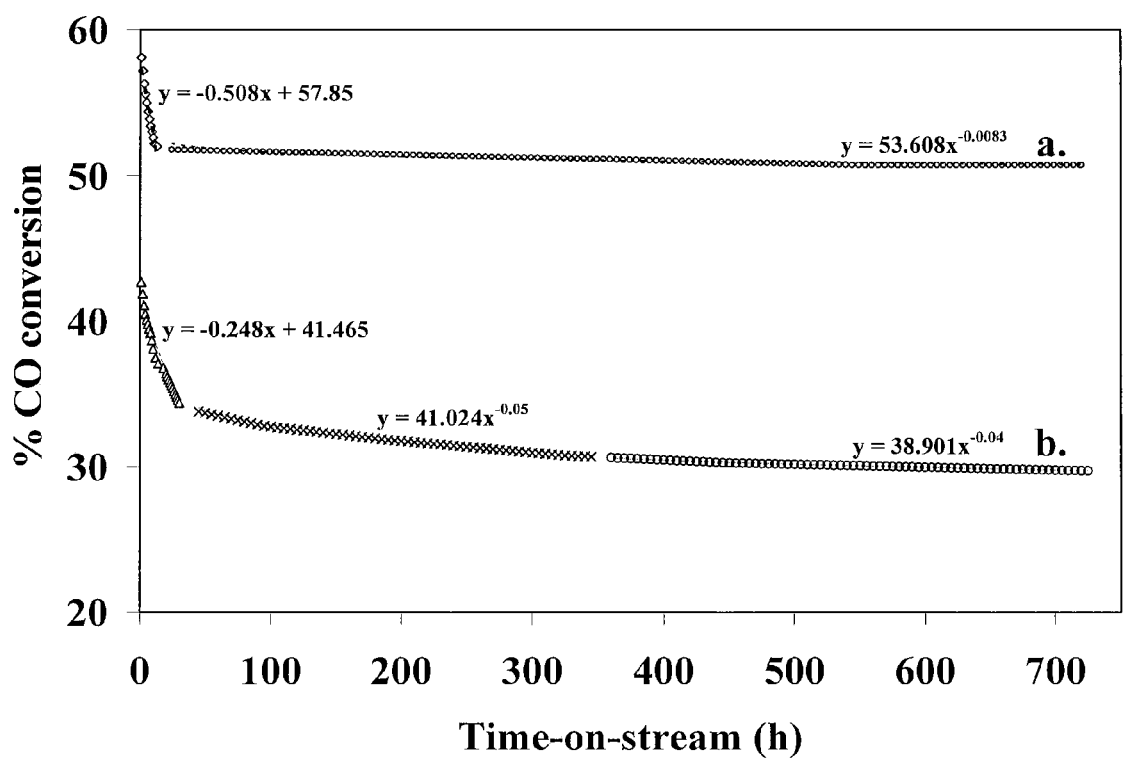
FIG. 48 shows % CO conversion with time-on-stream; a. an exemplary MWCNT-supported catalyst, b. an exemplary activated carbon-supported catalyst (wt. of the cat.=2 g, P=9.1 MPa, T=330° C., GHSV=3.8 m$^3$ (STP)/h/(kg of cat.)/h, $H_2$ to CO molar ratio=1.25).

The sulfided alkali-promoted trimetallic Co—Rh—Mo catalysts supported on MWCNTs and activated carbon were tested for the synthesis of higher alcohols from synthesis gas under similar conditions of 330° C., 9.1 MPa (1320 psig), and 3.8 m³ (STP)/(kg of cat.)/h. The profiles of % CO conversion as functions of time on stream for 720 h, with a synthesis gas feed containing 40 mole % CO, 50 mole % $H_2$, and 10 mole % Ar obtained over alkali-modified trimetallic Co—Rh—Mo catalysts supported on MWCNTs and activated carbon are shown in FIGS. 48a and 48b, respectively. Over the MWCNT-supported catalyst, two different deactivation steps are observed; the % CO conversion dropped by 10% (from 58% to 52%) during the first 12 h and remained almost constant with % CO conversion dropping by only 1.9% for the remaining time-on-stream of higher alcohols synthesis. Three different deactivation steps are distinguishable over the activated carbon-supported catalyst (1) during the first 36 h, the % CO conversion dropped by 21% (from 43% to 34%); (2) during 36 to 350 h, the % CO conversion dropped by 9% (from 34% to 31%); and (3) during 350 to 720, the % CO conversion dropped by 3% and almost reached a plateau region.

Figure 49:
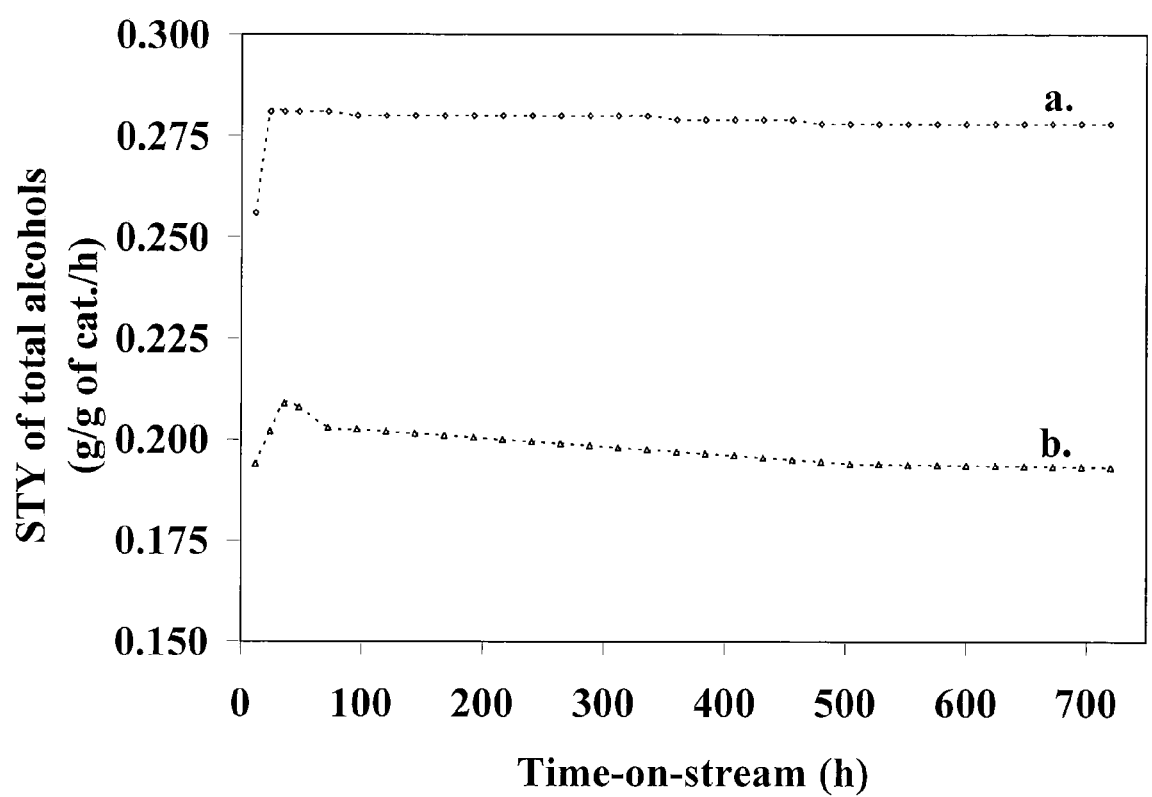
FIG. 49 shows total alcohols STY with time-on-stream; a. an exemplary MWCNT-supported catalyst, b. an exemplary activated carbon-supported catalyst (wt. of the cat.=2 g, P=9.1 MPa, T=330° C., GHSV=3.8 m$^3$ (STP)/h/(kg of cat.)/h, $H_2$/CO molar ratio=1.25).

FIGS. 49a and 49b present the total alcohols STY changes with time on stream of continuous higher alcohols synthesis for a period of 720 h obtained over alkali-modified trimetallic Co—Rh—Mo catalysts supported on MWCNTs and activated carbon, respectively. In Table 20, the alcohols formation rate values evaluated after reaction periods of 12, 24 and 720 h, which refer to the catalyst weights, surface area and active sites under the hypothesis of differential reactor are reported. The total alcohols STY increased from 0.256 g/(g of cat.)/h after a 12 h reaction period to 0.281 g/(g of cat.)/h after 24 h over the MWCNT-supported catalyst and remained almost constant over the remaining reaction time (FIG. 49a). The STY of total alcohols over the activated carbon-supported catalyst, increased from 0.194 to 0.209 g/(g of cat.)/h for samples collected from 12 to 36 h of time-on-stream, and decreased slowly to 0.193 g/(g of cat.)/h before it leveled off (FIG. 49b).

Figure 50:
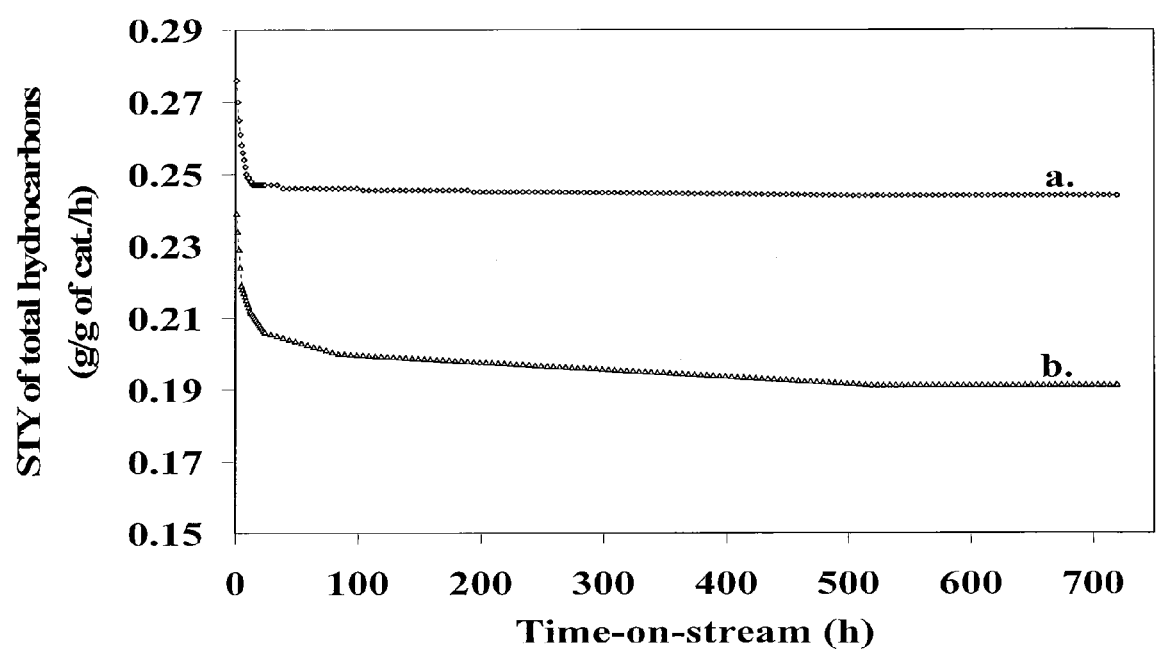
FIG. 50 shows total hydrocarbons STY with time-on-stream; a. an exemplary MWCNT-supported catalyst, b. an exemplary activated carbon-supported catalyst (wt. of the cat.=2 g, P=9.1 MPa, T=330° C., GHSV=3.8 m$^3$ (STP)/h/(kg of cat.)/h, $H_2$/CO molar ratio=1.25).

The change in total hydrocarbon STY with time-on-stream for a continuous reaction time of 720 h over the alkali-modified trimetallic catalysts supported on MWCNTs and activated carbon are given in FIGS. 50a and 50b, respectively. FIG. 50a shows that during the first 12 h reaction time, the total hydrocarbon STY decreased from 0.276 to 0.249 g/(g of cat.)/h and remained almost steady state in the next 710 h over the catalyst supported on MWCNTs. A rapid decrease in the STY of total hydrocarbons from 0.239 to 0.206 g/(g of cat.)/h occurred during the first 30 h of time-on-stream and then slowly leveled off to a constant value of 0.191 g/(g of cat.)/h (FIG. 50b).

Figure 51:
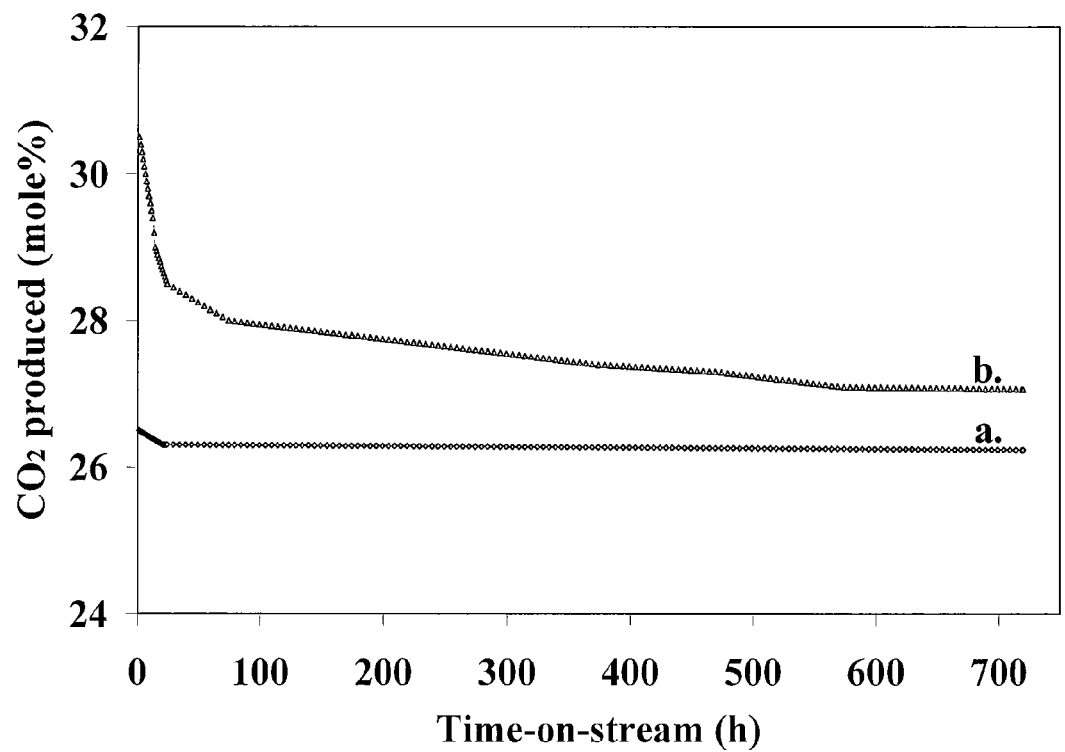
FIG. 51 shows water-gas-shift reaction rate with time-on-stream; a. an exemplary MWCNT-supported catalyst, b. an exemplary activated carbon-supported catalyst (wt. of the cat.=2 g, P=9.1 MPa, T=330° C., GHSV=3.8 m³ (STP)/h/(kg of cat.)/h, $H_2$/CO molar ratio=1.25).

The $CO_2$ produced in the reactor during 720 h of continuous operation over the MWCNTs and activated carbon-supported catalysts are reported in FIGS. 51a and 51b, respectively. The water-gas-shift (WGS) reaction rate was almost constant during the entire reaction period over the MWCNT-supported catalyst, whereas over the catalyst supported on activated carbon a drastic fall was noticed in the WGS reaction for first 30 h and then slowly leveled off to a constant value due to pore blockage of the support due to the sintering of catalyst species.

Regeneration of the spent catalyst at 450° C. increased the % CO conversion from 51 to 56% and over the catalysts supported on MWCNTs and activated carbon it increased from 29 to 36%, respectively. The total activity recovery over the MWCNTs and activated carbon-supported catalysts after regeneration is close to the total activity loss during the first deactivation step (about 10% and 19%, respectively). The addition of Co(Rh) to $MoS_2$ catalysts leads to the formation of active phase Co(Rh)—Mo—S that has a dual promotion effect of enhancing the activity by increasing S-vacancies and reducing the deposition of coke due to the improved hydrogenation rate of the coke ingredients.[93] The catalyst deactivation that occurred after the first step is due to the sintering of metal sulfide species on the support, which is an irreversible process.[94] Baghalha et al.[95] observed the loss of the Co—Mo—S active phase during hydrodesulfurization of a naphtha stream that caused about 19% of permanent catalyst activity deactivation during the first deactivation step. The present results demonstrate that the permanent loss of the active phase was negligible over the alkali-promoted trimetallic catalyst for higher alcohols synthesis and the recoverable activity loss can be assigned to the loss of unstable sulfur ions from the edges of metal sulfide crystallites. This study revealed that MWCNT is a novel catalyst support to decrease sintering, metal support interaction and coke formation during catalytic process.

Table 21 compares the activities of sulfided 4.5 wt % Co, 1.5 wt % Rh, 15 wt % Mo and 9 wt % K supported on MWCNTs and activated carbon with those of other catalysts discussed in the literature. The catalyst with the highest activity from each work was selected for comparison purposes. This table indicates that the sulfides alkali-modified Co—Rh—Mo catalysts in the present work perform better than those reported in the literature.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE APPLICATION

[1] Anderson, R. B. *The Fischer-Tropsch Synthesis*, Academic Press Inc., Orlando, 1984.

[2] Mandavi, V.; Peyrovi, M. H.; Synthesis of $C_1$-$C_6$ alcohols over copper/cobalt catalysts: Investigation of the influence of preparative procedures on the activity and selectivity of Cu—$Co_2O_3$/ZnO—$Al_2O_3$ catalyst. *Catal. Commun.* 2006, 7, 542-549.

[3] McCutchen, M. S. Synthesis of higher alcohols from carbon monoxide and hydrogen in a slurry reaction, Ph.D. Dissertation, North Carolina State University, Raleigh, N.C., 1992.

[4] Doan, P. T. Characterization of Cu—Co—C—K catalysts, M.Sc. Dissertation, Mississippi State University, Starkville, Mich., 2001.

[5] Iranmahboob, J. Formation of ethanol and higher alcohols from syngas, Ph.D. Dissertation, Mississippi State University, Starkville, Mich., 1999.

[6] Smith, K. J.; Anderson, R. B. The higher alcohol synthesis over promoted copper/zinc oxide catalysts. *Can. J. Chem. Eng.* 1983, 61, 40-45.

[7] Sugier, A.; Freund, E. *Process of manufacturing alcohols and more particularly saturated linear primary alcohols from synthesis gas*. U.S. Pat. No. 4,291,126, Sep. 22, 1981.

[8] Murchison, C. B.; Murdick, D. A. *Process for producing C2-C4 hydrocarbons from carbon monoxide and hydrogen*. U.S. Pat. No. 4,151,190, Apr. 24, 1979.

[9] Smith, K. J.; Herman, R. G.; Klier, K. Kinetic modelling of higher alcohol synthesis over alkali-Promoted Cu/ZnO and $MoS_2$ Catalysts. *Chem. Eng. Sci.* 1990, 45, 2639-2646.

[10] Li, Z.; Fu, Y.; Bao, J.; Jiang, M.; Hu, T.; Liu, T.; Xie, Y.-N. Effect of cobalt promoter on Co—Mo—K/C catalysts used for mixed alcohol synthesis. *Appl. Catal., A* 2001, 220, 21-30.

[11] Woo, H. C.; Park, K. Y. Mixed alcohols synthesis from carbon monoxide and dihydrogen over potassium-promoted molybdenum carbide catalysts. *Appl. Catal., A* 1991, 75, 267-280.

[12] Te, M.: Lowenthal, E. E.; Foley, H. C. Comparative study of $Rh/Al_2O_3$ and Rh—$Mo/Al_2O_3$ catalysts. *Chem. Eng. Sci.* 1994, 49, 4851-4859.

[13] Sudhakar, C.; Bhore, N. A.; Bischoff, K. B.; Manogue, W. H.; Mills, G. A. Molybdena enhanced $Rh/Al_2O_3$ catalysts. In *Proceedings of the 10th Meeting of the Catalysis Society of North America*, San Diego, Calif., 1987.

[14] Li, Z.-R.; Fu, Y.-L.; Jiang, M. Structures and performance of Rh—Mo—$K/Al_2O_3$ catalysts used for mixed alcohol synthesis from synthesis gas. *Appl. Catal., A* 1999, 187, 187-198.

[15] Foley, H. C.; Hong, A. J.; Brinen, J. S.; Allard, L. F.; Garratt-Reed, A. J. Bimetallic catalysts comprised of dissimilar metals for the reduction of carbon monoxide with hydrogen. *Appl. Catal., A* 1990, 61, 351-375.

[16] Shen, J. Y.; Matsuzaki, T.; Hanaoka, T.; Takeuchi, K.; Sugi, Y. The promoter function of molybdenum in $Rh/Mo/SiO_2$ catalysts for CO hydrogenation. *Catal. Lett.* 1994, 28, 329-339.

[17] Decanio, E. C.; Storm, D. A. Carbon monoxide adsorption by K/Co/Rh/Mo/$Al_2O_3$ higher alcohols catalysts. *J. Catal.* 1991, 132, 375-387.

[18] Gang, L.; Zhang, C. F.; Chang, Y.; Zhu, Z.; Ni, Y.; Cheng, L.; Yu, F. Synthesis of mixed alcohols from CO2 contained syngas on supported molybdenum sulfide catalysts. *Appl. Catal., A* 1997, 150, 243-252.

[19] Qi, H.; Li, D.; Yang, C.; Ma, Y.; Li, W.; Sun, Y.; Zhong, B. Nickel and manganese co-modified K/MoS2 catalyst: high performance for higher alcohols synthesis from CO hydrogenation. *Catal. Commun.* 2003, 4, 339-342.

[20] Sun, M.; Nelsona, A. E.; Adjaye, J. On the incorporation of nickel and cobalt into $MoS_2$-edge structures. *J. Catal.* 2004, 226, 32-40.

[21] Harris, S.; Chianelli, R. R. Catalysis by transition metal sulfides: A theoretical and experimental study of the relation between the synergic systems and the binary transition metal sulfides. *J. Catal.* 1986, 98, 17-31.

[22] Murchison, C. B.; Murdick, D. A. *Process for producing olefins from carbon monoxide and hydrogen*. U.S. Pat. No. 4,199,522, Apr. 22, 1980.

[23] Tatsumi, T.; Muramatsu, A.; Fukunaga, T.; Tominaga, H. Nickel promoted molybdenum catalysts for synthesis of mixed alcohols. In *Proc. 9th Intern. Congr. Catal.*; Phillips, M. J., Ternan, M., Eds.; The Chemical Institute of Canada: Ottawa, 1988; Vol. 2, p 618.

[24] Fujumoto, A.; Oba, T. Synthesis of C1-C7 alcohols from synthesis gas with supported cobalt catalysts. *Appl. Catal., A* 1985, 13, 289-319.

[25] Santiesteban, J. G.; Bogdan, C. E.; Herman, R. G.; Klier, K. Mechanism of $C_1$-$C_4$ alcohol synthesis over alkali/$MoS_2$ and alkali/Co/$MoS_2$ catalysts. In *Proc. 9th Intern. Congr. Catal.*; Phillips, M. J., Ternan, M., Eds.; The Chemical Institute of Canada: Ottawa, 1988; Vol. 2, p 561.

[26] Wong, S. F.; Stromville, N.Y.; Storm, D. A.; Montvale, N.J.; Patel, M. S. *Catalyst and method for producing lower aliphatic alcohols*. U.S. Pat. No. 4,983,638, Jan. 8, 1991.

[27] Li, X.; Feng, L.; Zhang, L.; Dadyburjor, D. B.; Kugler, E. L. Alcohol synthesis over pre-reduced activated carbon-supported molybdenum-based catalysts. *Molecules* 2003, 8, 13-30.

[27] Iranmahboob, J.; Toghiani, H.; Hill, D. O. Dispersion of alkali on the surface of Co—MoS2/clay catalyst: a comparison of K and Cs as a promoter for synthesis of alcohol. *Appl. Catal., A* 2003, 247, 207-218.

[29] Li, Z.; Jiang, M.; Bian, G.; Fu, Y.; Wei, S. Effect of rhodium modification on structures of sulfided Rh—Mo—K/Al2O3 catalysts studied by XAFS. *J. Synch. Radiat.* 1999, 6, 462-464.

[30] Kohl, A.; Linsmeier, C.; Taglauer, E.; Knozinger, H. Influence of support and promoter on the catalytic activity of $Rh/VO_x/SiO_2$ model catalysts. *Phys. Chem. Chem. Phys.* 2001, 3, 4639-4643.

[31] Wang, Y.; Li, J.; Mi, W. Probing study of Rh catalysts on different supports in CO hydrogenation. *React. Kinet. Catal. Lett.* 2002, 76, 141-150.

[32] Xua, R.; Yanga, C.; Wei, W.; Li, W.-H.; Suna, Y.-H.; Hu, T.-D. Fe-modified CuMnZrO2 catalysts for higher alcohols synthesis from syngas. *J. Mol. Catal. A: Chem.* 2004, 221, 51-58.

33. Zurita, M. J. P.; Cifarelli, M.; Cubeiro, M. L.; Goldwasser, J. A. M.; Pietri, E.; Garcia, L.; Aboukais, A.; Lamonier, J.-F. Palladium-based catalysts for the synthesis of alcohols. *J. Mol. Catal. A: Chem.* 2003, 206, 339-351.

34. Ryndin, Y. A.; Hicks, R. F.; Bell, A. T. Effects of metal-support interactions on the synthesis of methanol over palladium. *J. Catal.* 1981, 70, 287-297.

35. Kogelbauer, A.; Goodwin, J. G.; Oukaci, R. Ruthenium promotion of $Co/Al_2O_3$ Fischer-Tropsch catalysts. *J. Catal.* 1996, 160, 125-133.

36. Concha, B. E.; Bartholomew, G. L.; Bartholomew, C. H. CO hydrogenation on supported molybdenum catalysts: Effects of support on specific activities of reduced and sulfided catalysts. *J. Catal.* 1984, 89, 536-541.

37. Murchison, C. B.; Conway, M. N.; Steven, R. R.; Quarderer, G. J. Mixed alcohols from syngas over molybdenum catalysts. In *Proceedings of the Ninth International Congress on Catalyst*; 1998; Vol. 2, p 626.

38. Duchet, J. C.; van Oers, E. M.; de Beer, V. H. J.; Prins, R. Carbon supported sulfide catalysts. *J. Catal.* 1983, 80, 386-402.

39. Zaman, M.; Khodadi, A.; Mortazavi, Y. Fischer-Tropsch synthesis over cobalt dispersed on carbon nanotubes-based supports and activated carbon. *Fuel Process. Technol.* 2009, 90, 1214-1219.

40. Rodriquez-Reinoso, F. The role of carbon materials in heterogeneous catalysis. *Carbon* 1998, 36, 159-175.

41. Eswaramoorthi, I.; Sundaramurthy, V.; Das, N.; Dalai, A. K.; Adjaye, J. Application of multi-walled carbon nanotubes as efficient support to NiMo hydrotreating catalyst. *Appl. Catal., A* 2008, 339, 187-195.

42. Xiaoming, M.; Guodong, L.; Hongbin, Z. Co—Mo—K sulfide-based catalyst promoted by multiwalled carbon nanotubes for higher alcohol synthesis from syngas. *Chin. J. Catal.* 2006, 27, 1019-1027.

43. Surisetty, V. R.; Tavasoli, A.; Dalai, A. K. Synthesis of higher alcohols from syngas over alkali promoted MoS2 catalysts supported on multi-walled carbon nanotubes. *Appl. Catal. A* 2009, 365, 243-251.

44. Moronta, A.; Troconis, M. E.; Gonzalez, E.; Moran, C.; Sanchez, J.; Gonzalez, A.; Quinonez, J. Dehydrogenation of ethylbenzene to styrene catalyzed by Co, Mo and CoMo catalysts supported on natural and aluminum-pillared clays: Effect of the metal reduction. *Appl. Catal., A* 2006, 310, 199-204.

45. Jiang, M.; Bian, G.-Z.; Fu, Y.-L. Effect of the K—Mo interaction in K—MoO3/γ-Al2O3 catalysts on the properties for alcohol synthesis from syngas. *J. Catal.* 1994, 146, 144-154.

46. Calafata, A.; Vivas, F.; Brito, J. L. Effects of phase composition and of potassium promotion on cobalt molybdate catalysts for the synthesis of alcohols from CO2 and H2. *Appl. Catal., A* 1998, 172, 217-224.

47. Fu, Y.-L.; Fujimoto, K.; Lin, P.; Omata, K.; Yu, Y. Effect of calcination conditions of the oxidized precursor on the structure of a sulfided K—Mo/γ-Al2O3 catalyst for mixed alcohol synthesis. *Appl. Catal., A* 1995, 126, 273-285.

48. Pan, X.; Fan, Z.; Chen, W.; Ding, Y.; Luo, H.; Bao, X. Enhanced ethanol production inside carbon-nanotube reactors containing catalytic particles. *Nat. Mater.* 2007, 6, 507-511.

49. Berge, P. J. V.; van de Loosdrecht, J.; Barradas, S.; van der Kraan, A. M. Oxidation of cobalt based Fischer-Tropsch catalysts as a deactivation mechanism. *Catal. Today* 2000, 58, 321-334.

50. Feng, L.; Li, X.; Dadyburjor, D. B.; Kugler, E. L. A temperature-programmed-reduction study on alkali-promoted, carbon-supported molybdenum catalysts. *J. Catal.* 2000, 190, 1-13.

51. Noronha, F. B.; Baldanza, M. A. S.; Schmal, M. CO and NO Adsorption on Alumina-Pd—Mo Catalysts: Effect of the Precursor Salts. *J. Catal.* 1999, 188, 270-280.

52. Surisetty, V. R.; Dalai, A. K.; Kozinski, J. Synthesis of higher alcohols from synthesis gas over Co-promoted alkali-modified $MoS_2$ catalysts supported on MWCNTs. *Appl. Catal., A General* 2010, 385 (1-2), 153-162.

53. Surisetty, V. R.; Dalai, A. K.; Kozinski, J. Effect of Rh promoter on MWCNT-supported alkali-modified $MoS_2$ catalysts for higher alcohols synthesis from CO hydrogenation. *Appl. Catal. A,* 2010, 381, 282-288.

54. Surisetty, V. R.; Dalai, A. K.; Kozinski, J. Alkali-promoted trimetallic Co—Rh—Mo sulfide catalysts for higher alcohols synthesis from synthesis gas: Comparison of MWCNT and activated carbon supports. *Ind. Eng. Chem. Res.* 2010, 49, 6956-6963.

55. Surisetty, V. R.; Dalai, A. K.; Kozinski, J. Intrinsic reaction kinetics of higher alcohols synthesis from synthesis gas over sulfided alkali-promoted Co—Rh—Mo trimetallic catalyst supported on MWCNTs. *Energy & Fuels* 2011, 25(2), 580-590.

56. Bhusan, B., Ed. *Springer handbook of nanotechnology,* 2nd ed., Springer: New York, 2007.

57. Eswaramoorthi, I.; Sundaramurthy, V.; Dalai, A. K. Partial oxidation of methanol for hydrogen production over carbon nanotubes supported Cu—Zn catalysts. *Appl. Catal., A* 2006, 313, 22-34.

58. Pan, X.; Fan, Z.; Chen, W.; Ding, Y.; Luo, H.; Bao, X. Enhanced ethanol production inside carbon-nanotube reactors containing catalytic particles. *Nat. Mater.* 2007, 6, 507-511.

59. Berge, P. J. V.; van de Loosdrecht, J.; Barradas, S.; van der Kraan, A. M. Oxidation of cobalt based Fischer-Tropsch catalysts as a deactivation mechanism. *Catal. Today* 2000, 58, 321-334.

60. Kogelbauer, A.; Goodwin, J. G.; Oukaci, R. Ruthenium promotion of $Co/Al_2O_3$ Fischer-Tropsch catalysts. *J. Catal.* 1996, 160, 125-133.

61. Rodriguez, J. A.; Chaturbedi, S.; Hanson, C. J.; Albornoz, A.; Brito, J. L. Reaction of $H_2$ and $H_2S$ with $CoMoO_4$ and $NiMoO_4$: TPR, XANES, Time-resolved XRD, and molecular-orbital studies. *J. Phys. Chem. B* 1999, 103, 770-781.

62. Zubavichus, Y. V.; Slovokhotov, Y. L.; Schilling, P. J.; Tittsworth, R. C.; Golub, A. S.; Protzenko, G. A.; Novikov, Y. N. X-ray absorption fine structure study of the atomic and electronic structure of molybdenum disulfide intercalation compounds with transition metals. *Inorg. Chim. Acta* 1998, 280, 211-218.

63. Guay, D.; Divigalpitiya, W. M. R.; Bdlanger, D.; Feng, X. H. Chemical bonding in restacked single-layer $MoS_2$ by X-ray absorption spectroscopy. *Chem. Mater.* 1994, 6, 614-619.

64. Hay, S. J.; Metson, J. B.; Hyland, M. M. Sulfur speciation in aluminum smelting anodes. *Ind. Eng. Chem. Res.* 2004, 43, 1690-1700.

65. Aritani, H.; Tanaka, T.; Funabiki, T.; Yoshida, S. Study of the local structure of molybdenum-magnesium binary oxides by means of Mo $L_3$-edge XANES and UV-Vis spectroscopy. *J. Phys. Chem.* 1996, 100, 19495-19501.

66. Topsoe, H.; Clausen, B. S.; Topsoe, N.Y.; Pederson, E. Recent basic research in hydrodesulfurization catalysis. *Ind. Eng. Chem. Fundam.* 1986, 25, 25-36.

67. Rouquerol, J.; Avnir, D; Fairbridge, C. W.; Everett, D. H.; Haynes, J. H.; Pernicone, N.; et al. Recommendations for the characterization of porous solids. *Pure Appl. Chem.* 1994, 66, 1739-1758.
68. Azevedo, D. C. S.; Araujo, J. C. S.; Bastos-Neto, M.; Torres, A. E. B.; Jaguaribe, E. F.; Cavalcante, C. L. Microporous activated carbon prepared from coconut shells using chemical activation with zinc chloride. *Micropor. Mesopor. Mat.* 2007, 100, 361-364.
69. Huang, Z.-D.; Bensch, W.; Kienle, L.; Fuentes, S.; Alonso, G.; Ornelas, C. SBA-15 as support for $MoS_2$ and $Co$—$MoS_2$ catalysts derived from thiomolybdate complexes in the reaction of HDS of DBT. *Catal. Lett.* 2008, 122, 57-67.
70. Vradman, L.; Landau, M. V.; Herskowitz, M.; Ezersky, V.; Talianker, M.; Nikitenko, S.; et al. High loading of short $WS_2$ slabs inside SBA-15: promotion with nickel and performance in hydrodesulfurization and hydrogenation. *J. Catal.* 2003, 213, 163-175.
71. Kumaran, G. M.; Garg, S.; Soni, K.; Kumar, M.; Sharma, L. D.; Dhar, G. M.; et al. Effect of Al-SBA-15 support on catalytic functionalities of hydrotreating catalysts: I. Effect of variation of Si/Al ratio on catalytic functionalities. *Appl. Catal., A* 2006, 305, 123-129.
72. Li, Z.-R.; Fu, Y.-L.; Jiang, M.; Hu, T.-D.; Liu, T.; Xie Y.-N. Active carbon supported Mo—K catalysts used for alcohol synthesis. *J. Catal.* 2001, 199, 155-161.
73. Jiang, M.; Bian, G.-Z.; Fu, Y.-L. Effect of the K—Mo interaction in K—$MoO_3$/γ-$Al_2O_3$ catalysts on the properties for alcohol synthesis from syngas. *J. Catal.* 1994, 146, 144-154.
74. Calafata, A.; Vivas, F.; Brito, J. L. Effects of phase composition and of potassium promotion on cobalt molybdate catalysts for the synthesis of alcohols from $CO_2$ and $H_2$, *Appl. Catal., A* 1998, 172, 217-224.
75. Fu, Y.-L.; Fujimoto, K.; Lin, P.; Omata, K.; Yu, Y. Effect of calcination conditions of the oxidized precursor on the structure of a sulfided K—Mo/γ-$Al_2O_3$ catalyst for mixed alcohol synthesis. *Appl. Catal., A* 1995, 126, 273-285.
76. Taguchi, G. *System of experimental design. Quality Resources*, Kraus and Americans Supplier Institute (eds): USA, 1991.
77. Bolboaca, S. D.; Jantschi, L. Design of experiments: Useful orthogonal arrays for number of experiments from 4 to 16. *Entropy* 2007, 9, 198-232.
78. Fogler, H. S. *Elements of Chemical Reaction Engineering*, Prentice Hall PTR, USA, 3$^{rd}$ ed., 1999.
79. Butt, J. B. *Reaction Kinetics and Reactor Design*, USA, 2$^{nd}$ ed., 2000.
80. Frössling N. The evaporation of falling drops. *Gerlands Beitr. Geophys.* 1938, 52, 170-216.
81. Beretta, A.; Micheli, E.; Tagliabue, L.; Tronconi, E. Development of a process for higher alcohol production via synthesis gas. *Ind. Eng. Chem. Res.* 1998, 37, 3896-3908.
82. Tronconi, E.; Forzatti, P.; Pasquon, I. I. An investigation of the thermodynamic constraints in higher alcohol synthesis over Cs-promoted ZnCr-oxide catalyst. *J. Catal.* 1990, 124, 376-390.
83. Tronconi, E.; Ferlazzo, N.; Pasquon, I. Synthesis of alcohols from carbon oxides and hydrogen. *Ind. Eng. Chem. Res.* 1987, 26, 2122-2129.
84. Gunturu, A. K.; Kugler, E. L.; Cropley, J. B.; Dadyburjor, D. B. A kinetic model for the synthesis of high-molecular-weight alcohols over a sulfided Co—K—Mo/C catalyst. *Ind. Eng. Chem. Res.* 1998, 37, 2107-2115.
85. Christensen, J. M.; Mortensen, P. M.; Trane, R.; Jensen, P. A.; Jensen, A. D. Effects of $H_2S$ and process conditions in the synthesis of mixed alcohols from syngas over alkali-promoted cobalt-molybdenum sulfide. *Appl. Catal. A,* 2009, 366, 29-43.
86. Chen, W.; Fan, Z.; Pan, X.; Bao, X. Effect of confinement in carbon nanotubes on the activity of Fischer-Tropsch iron Catalyst, *J. Am. Chem. Soc,* 2008, 130, 9414-9419.
87. Tavasoli, A.; Tre'panier, M.; Dalai, A. K.; Abatzoglou, N. Effects of confinement in carbon nanotubes on the activity, selectivity, and lifetime of Fischer-Tropsch Co/carbon nanotube catalysts. *J. Chem. Eng. Data* 2010, 55(8), 2757-2763.
88. Eswaramoorthi, I.; Sundaramurthy, V.; Das, N.; Dalai, A. K.; Adjaye, J. Application of multi-walled carbon nanotubes as efficient support to NiMo hydrotreating catalyst. *Appl. Catal. A* 2008, 339, 187-195.
89. Li, Z.; Fu, Y.; Jiang, M.; Hu, T.; Liu, T.; Xie, Y. Active carbon supported Mo—K catalysts used for alcohol synthesis. *J. Catal.* 2001, 199, 155-161.
90. Jiang, M.; Bian, G-Z.; Fu, Y-L. Effect of the K—Mo interaction in K—$MoO_3$/γ-$Al_2O_3$ catalysts on the properties for alcohol synthesis from syngas. *J. Catal.* 1994, 146, 144-154.
91. Calafata, A.; Vivas, F.; Brito, J. L.; Effects of phase composition and of potassium promotion on cobalt molybdate catalysts for the synthesis of alcohols from $CO_2$ and $H_2$, *Appl. Catal., A* 1998, 172, 217-224.
92. Fu, Y-L.; Fujimoto, K.; Lin, P.; Omata, K.; Yu, Y. Effect of calcination conditions of the oxidized precursor on the structure of a sulfided K—Mo/γ-$Al_2O_3$ catalyst for mixed alcohol synthesis. *Appl. Catal. A* 1995, 126, 273-285.
93. Vogelaar, B. M.; Steiner, P.; van der Zijden, P. F.; van Langeveld, A. D.; Eijsbouts, S.; Moulijn, J. A. Catalyst deactivation during thiophene HDS: The role of structural sulfur. *Appl. Catal., A.* 2007, 318, 28-36.
94. Ratnasamy, P.; Sivasanker, S. Structural chemistry of Co—Mo-alumna catalysts. *Cat. rev.* 1980, 22, 401-429.
95. Baghalha, M.; Hoseini, S. M. Long-term deactivation of a commercial CoMo/γ-$Al_2O_3$ catalyst in hydrodesulfurization of a naphtha stream. *Ind. Eng. Chem. Res.* 2009, 48, 3331-3340.

TABLE 1

| Catalyst | Targeted composition (wt %) | | | | Measured composition (wt %) | | | BET surface area ($m^2/g$) | Total pore volume (cc/g) | Average pore diameter (nm) | CO uptake (μmole/g of cat.) | Dispersion of metals (%) |
|---|---|---|---|---|---|---|---|---|---|---|---|---|
| | K | Mo | Rh | Co | Mo | Rh | Co | | | | | |
| Acid Treated MWCNT | — | — | — | — | — | — | — | 220 | 0.66 | 10.9 | — | — |
| Acid Treated AC | — | — | — | — | — | — | — | 676 | 0.97 | 1.9 | — | — |
| Rh—Mo—K/ MWCNTs | 9 | 15 | 1.5 | — | 14.4 | 1.3 | — | 77 | 0.30 | 17.7 | 135 | 39.5 |

TABLE 1-continued

| Catalyst | Targeted composition (wt %) K | Targeted composition (wt %) Mo | Targeted composition (wt %) Rh | Targeted composition (wt %) Co | Measured composition (wt %) Mo | Measured composition (wt %) Rh | Measured composition (wt %) Co | BET surface area (m²/g) | Total pore volume (cc/g) | Average pore diameter (nm) | CO uptake (μmole/g of cat.) | Dispersion of metals (%) |
|---|---|---|---|---|---|---|---|---|---|---|---|---|
| 4.5 wt % Co—Rh—Mo—K/MWCNT | 9 | 15 | 1.5 | 4.5 | 14.3 | 1.2 | 4.2 | 68 | 0.24 | 17.9 | 237 | 47.8 |
| 6 wt % Co—Rh—Mo—K/MWCNT | 9 | 15 | 1.5 | 6.0 | 14.1 | 1.3 | 5.7 | 59 | 0.20 | 18.3 | 245 | 44.8 |
| 4.5 wt % Co—Rh—Mo—K/AC | 9 | 15 | 1.5 | 4.5 | 13.7 | 0.8 | 3.8 | 97 | 0.16 | 7.2 | 137 | 27.7 |
| 6 wt % Co—Rh—Mo—K/AC | 9 | 15 | 1.5 | 6.0 | 13.9 | 0.9 | 5.1 | 83 | 0.11 | 7.9 | 144 | 26.3 |

TABLE 2

| Crystal phase | 2θ | d-spacing | Reflection plane h k l |
|---|---|---|---|
| Oxidized form of catalysts: | | | |
| Graphite (C) | 26.6° | 3.347 | 1 1 1 |
| $MoO_3$ | 40.2° | 2.271 | 1 5 0 |
| $KMo_4O_6$ | 16.0° | 5.336 | 1 1 0 |
| $K_2Mo_2O_7$ | 19.4° | 4.689 | 1 1 0 |
| $K_2Mo_7O_{20}$ | 23.6° | 3.770 | 1 0 2 |
| $K_2Mo_2O_7$ | 28.5° | 3.222 | 0 0 2 |
| $K_2Mo_2O_7$ | 29.8° | 2.956 | 0 1 2 |
| $K_2Mo_2O_7$ | 30.9° | 2.845 | 2 1 0 |
| $KMo_4O_6$ | 37.1° | 2.403 | 4 0 0 |
| $K_2Mo_7O_{20}$ | 53.8° | 1.700 | 0 10 4 |
| Sulfided form of catalysts: | | | |
| $MoS_2$ | 14.6° | 6.110 | 0 0 3 |
| $MoS_2$ | 33.4° | 2.707 | 1 0 1 |
| $MoS_2$ | 40.9° | 2.199 | 0 1 5 |
| $MoS_2$ | 58.9° | 1.570 | 1 1 0 |
| $K_{0.4}MoS_2$ | 21.5° | 4.130 | 0 0 4 |
| $KMo_3S_3$ | 28.7° | 3.100 | 1 1 1 |
| $K_2MoS_4$ | 29.9° | 3.020 | 3 0 1 |
| $K_2MoS_4$ | 31.5° | 2.780 | 3 0 2 |
| $Co_9S_8$ | 52.4 | 1.751 | 4 4 0 |

TABLE 3

| CATALYST | CO CONVERSION (%) | PRODUCT STY (G/(G OF CAT.)/H) TOTAL ALCOHOLS | PRODUCT STY (G/(G OF CAT.)/H) TOTAL HYDROCARBONS | $CO_2$ PRODUCED (MOLE %) | ALCOHOL SELECTIVITY (WT %) METHANOL | ALCOHOL SELECTIVITY (WT %) ETHANOL | ALCOHOL SELECTIVITY (WT %) HIGHER ALCOHOLS |
|---|---|---|---|---|---|---|---|
| RH—MO—K/MWCNT | 40.1 | 0.211 | 0.332 | 34.6 | 5.4 | 16.0 | 24.6 |
| 4.5 WT % CO—RH—MO—K/MWCNT | 45.2 | 0.244 | 0.251 | 21.7 | 6.7 | 20.1 | 31.4 |
| 6 WT % CO—RH—MO—K/MWCNT | 48.9 | 0.235 | 0.293 | 18.9 | 5.9 | 18.5 | 27.8 |
| 4.5 WT % CO—RH—MO—K/AC | 31.2 | 0.167 | 0.188 | 25.7 | 11.6 | 9.1 | 18.8 |
| 6 WT % CO—RH—MO—K/AC | 35.3 | 0.155 | 0.231 | 20.2 | 9.8 | 8.3 | 15.9 |

(wt. of the cat. = 2 g, P = 8.3 MPa, T = 320° C., GHSV = 3.6 m³ (STP)/(kg of cat.)/h, $H_2$ to CO molar ratio = 1)

TABLE 4

| Catalyst | Sample A Co—Mo—K/AC | Sample B Rh—Mo—K/$Al_2O_3$ | Sample C Co—Mo—K/Co decorated MWCNTs | Sample D Co—Rh—Mo—K/MWCNTs |
|---|---|---|---|---|
| Temperature (K) | 330 | 327 | 340 | 330 |
| $H_2$/CO molar ratio | 2.0 | 2.0 | 1.0 | 1.0 |
| Pressure (MPa) | 5.0 | 4.0 | 5.0 | 8.3 |
| CO conversion (%) | 14.3 | 4.4 | 12.6 | 48.6 |
| STY of alcohols (g/(g of cat./h)) | 0.199* | 0.062** | 0.154 | 0.261 |

TABLE 5

| Catalyst | CO conversion (%) | Product STY (g/(g of cat.)/h) Total alcohols | Product STY (g/(g of cat.)/h) Total Hydrocarbons | CO$_2$ produced (mole %) | Alcohol Selectivity (wt %) Methanol | Alcohol Selectivity (wt %) Ethanol | Alcohol Selectivity (wt %) Higher alcohols |
|---|---|---|---|---|---|---|---|
| Mo—K/MWCNT | 29.1 | 0.12 | 0.19 | 23.5 | 9.3 | 6.2 | 13.8 |
| Co—Mo—K/MWCNT | 46.9 | 0.26 | 0.39 | 36.5 | 6.2 | 18.8 | 30.6 |
| Rh—Mo—K/MWCNT | 47.3 | 0.26 | 0.37 | 39.7 | 6.0 | 19.6 | 30.9 |
| Co—Rh—Mo—K/MWCNT | 51.2 | 0.29 | 0.29 | 28.0 | 6.7 | 25.7 | 39.4 |
| Co—Rh—Mo/MWCNT | 64.8 | 0.05 | 0.83 | 36.2 | 2.2 | 1.1 | 1.8 |
| Co—Rh—Mo K/AC | 35.6 | 0.19 | 0.22 | 31.6 | 13.1 | 12.6 | 22.8 |

(wt. of the cat. = 2 g, P = 9.1 MPa, T = 330° C., GHSV = 3.8 m$^3$ (STP)/(kg of cat.)/h, H$_2$ to CO molar ratio = 1.25)

TABLE 6

| Catalyst | BET surface area (m$^2$/g) | Total pore volume (cc/g) | Average pore diameter (nm) |
|---|---|---|---|
| Mo—K/MWCNT | 109 | 0.41 | 14.9 |
| Co—Mo—K/MWCNT | 89 | 0.36 | 15.7 |
| Rh—Mo—K/MWCNT | 86 | 0.35 | 16.0 |
| Co—Rh—Mo—K/MWCNT | 79 | 0.29 | 16.7 |
| Co—Rh—Mo/MWCNT | 68 | 0.23 | 17.8 |
| Co—Rh—Mo—K/AC | 111 | 0.21 | 6.4 |

TABLE 7

| Crystal phase | 2θ | d-spacing | Reflection plane h k l |
|---|---|---|---|
| Graphite (C) | 26.6° | 3.35 | 1 1 1 |
| MoS$_2$ | 14.6° | 6.11 | 0 0 3 |
| MoS$_2$ | 33.4° | 2.71 | 1 0 1 |
| MoS$_2$ | 40.9° | 2.20 | 0 1 5 |
| MoS$_2$ | 58.9° | 1.57 | 1 1 0 |
| K$_{0.4}$MoS$_2$ | 21.5° | 4.13 | 0 0 4 |
| KMo$_3$S$_3$ | 28.7° | 3.10 | 1 1 1 |
| K$_2$MoS$_4$ | 29.9° | 3.02 | 3 0 1 |
| K$_2$MoS$_4$ | 31.5° | 2.78 | 3 0 2 |
| Co$_9$S$_8$ | 52.4 | 1.75 | 4 4 0 |

TABLE 8

| Catalyst Support | Pure support $S_{BET}$ (m$^2$/g) | Pure support $S_{me}$ (m$^2$/g) | Pure support $V_{tot}$ (cc/g) | Pure support $V_{me}$ (cc/g) | Pure support D (nm) | Pure support % Me | Catalyst $S_{BET}$ (m$^2$/g) | Catalyst $S_{me}$ (m$^2$/g) | Catalyst BE | Catalyst $V_{tot}$ (cc/g) | Catalyst $V_{me}$ (cc/g) | Catalyst D (nm) | Catalyst % Me |
|---|---|---|---|---|---|---|---|---|---|---|---|---|---|
| AC-Darco | 658 | 197 | 0.93 | 0.35 | 1.95 | 38 | 97 | 41 | 0.79 | 0.16 | 0.08 | 7.21 | 50 |
| AC-RX$_3$ extra | 1249 | 483 | 0.66 | 0.31 | 1.58 | 47 | 292 | 140 | 0.67 | 0.34 | 0.19 | 4.61 | 56 |
| AC-Fluid coke | 245 | 161 | 0.17 | 0.13 | 2.81 | 76 | 127 | 87 | 0.26 | 0.10 | 0.08 | 3.03 | 80 |
| AC-CGP super | 1739 | 1534 | 1.33 | 1.25 | 3.07 | 94 | 816 | 642 | 0.33 | 0.60 | 0.57 | 3.92 | 95 |
| MWCNTs | 188 | 162 | 0.53 | 0.52 | 11.34 | 98 | 68 | 59 | 0.48 | 0.24 | 0.24 | 17.91 | 100 |

$S_{BET}$—BET surface area;
$S_{me}$—Mesopore surface area;
$V_{tot}$—Total pore volume;
$V_{me}$—Mesoporous volume;
D—Average pore diameter;
% Me—Percentage of mesoporosity; and
BE—Blocking extent of the pores of the support due to metal loading

TABLE 9

| Catalyst support | CO uptake (μmole/g of cat.) | Total number of metal atoms present in the sample (μmole/g of cat) | Dispersion of metals (%) |
|---|---|---|---|
| AC-Darco | 137 | 495 | 27.7 |
| AC-RX$_3$ extra | 140 | 495 | 28.3 |
| AC-Fluid coke | 161 | 495 | 32.6 |
| AC-CGP super | 195 | 495 | 39.4 |
| MWCNT | 237 | 495 | 47.9 |

TABLE 10

| Catalyst support | CO conversion (%) | Product STY (g/(g of cat.)/h) Total alcohols | Product STY (g/(g of cat.)/h) Total hydrocarbons | $CO_2$ produced (mole %) | Alcohol Selectivity (wt %) Methanol | Alcohol Selectivity (wt %) Ethanol | Alcohol Selectivity (wt %) Higher alcohols |
|---|---|---|---|---|---|---|---|
| AC-Darco | 35.6 | 0.141 | 0.204 | 28.2 | 13.2 | 8 | 11.7 |
| AC-$RX_3$ extra | 39.6 | 0.154 | 0.217 | 27.3 | 13.7 | 8.3 | 12.1 |
| AC-Fluid coke | 41.8 | 0.187 | 0.253 | 26.3 | 14.3 | 8.7 | 12.7 |
| AC-CGP super | 44.5 | 0.202 | 0.275 | 25.0 | 14.4 | 9 | 13.1 |
| MWCNT | 52.4 | 0.296 | 0.345 | 18.4 | 17.8 | 11.7 | 16.8 |

(wt. of the cat. = 2 g, P = 8.3 MPa, T = 330° C., GHSV = 3.6 m$^3$ (STP)/(kg of cat.)/h, $H_2$/CO molar ratio = 2)

TABLE 11

| Model | Quality of fit ($R^2$ Value) |
|---|---|
| Methanol STY | 0.993 |
| (Ethanol STY)$^{0.5}$ | 0.981 |
| (Higher alcohols STY)$^{0.5}$ | 0.980 |
| (Total alcohols STY)$^{0.5}$ | 0.982 |
| Hydrocarbons STY | 0.971 |
| $CO_2$ STY | 0.954 |
| (Methanol selectivity)$^{0.5}$ | 0.987 |
| (Ethanol selectivity)$^{0.5}$ | 0.975 |
| Higher alcohols selectivity | 0.943 |
| Total alcohols selectivity | 0.860 |

TABLE 12 p-value of model after insignificant factors excluded

| Coefficient of determination | (Methanol selectivity)$^{0.5}$ | (Ethanol selectivity)$^{0.5}$ | Higher alcohols selectivity | Total alcohols selectivity |
|---|---|---|---|---|
| $R^2$ | 0.986 | 0.976 | 0.943 | 0.860 |
| Adjusted $R^2$ | 0.978 | 0.959 | 0.923 | 0.809 |
| Predicted $R^2$ | 0.960 | 0.905 | 0.876 | 0.741 |

TABLE 13

| $H_2$/CO (moles/moles) | 1 | 1.5 | 2 |
|---|---|---|---|
| Repetitions # | 4* | 3* | 3* |
| Ethanol STY (g/(g of cat.)/h) | 0.148, 0.150, 0.151, 0.154 | 0.126, 0.128, 0.124 | 0.116, 0.114, 0.115 |
| Ethanol selectivity (wt %) | 25.8, 26.1, 26.6, 25.7 | 19.5, 20.1, 19.1 | 9.6, 9.1, 9.6 |
| Repetitions # | 2** | 2** | 2** |
| Ethanol STY (g/(g of cat.)/h) | 0.151, 0.152 | 0.122, 0.127 | 0.113, 0.119 |
| Ethanol selectivity (wt %) | 26.5, 26.7 | 18.8, 19.7 | 9.5, 10.2 |
| t - value | | | |
| Ethanol STY (g/(g of cat.)/h) | 0.39 | 0.29 | 0.42 |
| Ethanol selectivity (wt %) | 1.78 | 0.63 | 1.23 |
| p - value | | | |
| Ethanol STY (g/(g of cat.)/h) | 0.358 | 0.287 | 0.351 |
| Ethanol selectivity (wt %) | 0.075 | 0.287 | 0.153 |

(T = 330° C., P = 1320 psig (9.1 Mpa), and GHSV = 3.8 m$^3$ (STP)/(kg of cat./h))
*experiments were repeated using same catalyst;
**experiments were repeated using freshly loaded catalyst every time

TABLE 14

| Run | T (° C.) | P (psi) | GHSV (m$^3$ (STP)/(kg of cat.)/h) | $H_2$/CO (moles/moles) |
|---|---|---|---|---|
| Set-1 | | | | |
| 14 | 350 | 1000 | 3.6 | 0.5 |
| 13 | 350 | 800 | 4.2 | 1.0 |
| 1 | 275 | 800 | 2.4 | 0.5 |
| 11 | 325 | 1200 | 2.4 | 1.0 |
| 15 | 350 | 1200 | 3.0 | 2.0 |
| 2 | 275 | 1000 | 3.0 | 1.0 |
| 12 | 325 | 1400 | 3.0 | 0.5 |
| 5 | 300 | 800 | 3.0 | 1.5 |
| 8 | 300 | 1400 | 3.6 | 1.0 |
| 4 | 275 | 1400 | 4.2 | 2.0 |
| 9 | 325 | 800 | 3.6 | 2.0 |
| 6 | 300 | 100 | 2.4 | 2.0 |
| 3 | 275 | 1200 | 3.6 | 1.5 |
| 10 | 325 | 1000 | 4.2 | 1.5 |
| 7 | 300 | 1200 | 4.2 | 0.5 |
| 16 | 350 | 1400 | 2.4 | 1.5 |
| CP | 315 | 1100 | 3.3 | 1.25 |
| Set-2 | | | | |
| 1 | 320 | 1200 | 3.6 | 1.25 |
| 3 | 320 | 1400 | 4.0 | 1.25 |
| 5 | 330 | 1300 | 4.0 | 1.25 |
| 4 | 330 | 1200 | 3.8 | 1.25 |
| 6 | 330 | 1400 | 3.6 | 1.25 |
| 7 | 340 | 1200 | 4.0 | 1.25 |
| 8 | 340 | 1300 | 3.6 | 1.25 |
| 2 | 320 | 1300 | 3.8 | 1.25 |
| 9 | 320 | 1400 | 3.8 | 1.25 |

TABLE 15

| Particle size range (μm) | Targeted composition (wt %) K | Targeted composition (wt %) Mo | Targeted composition (wt %) Rh | Targeted composition (wt %) Co | Measured composition (wt %) Mo | Measured composition (wt %) Rh | Measured composition (wt %) Co |
|---|---|---|---|---|---|---|---|
| 707-841 | 9 | 15 | 1.5 | 4.5 | 14.0 | 1.4 | 4.3 |
| 420-500 | 9 | 15 | 1.5 | 4.5 | 14.1 | 1.3 | 4.1 |
| 210-297 | 9 | 15 | 1.5 | 4.5 | 14.0 | 1.1 | 4.1 |
| 147-210 | 9 | 15 | 1.5 | 4.5 | 14.3 | 1.2 | 4.2 |

TABLE 16

| Particle size range (μm) | $d_p$ (mm) | $k_c$ (m/s) | δ (mm) |
|---|---|---|---|
| T = 275° C. | | | |
| 707-841 | 0.774 | 3.62 * 10$^{-4}$ | 0.142 |
| 420-500 | 0.460 | 5.21 * 10$^{-4}$ | 0.099 |
| 210-297 | 0.254 | 8.06 * 10$^{-4}$ | 0.064 |
| 147-210 | 0.179 | 1.05 * 10$^{-4}$ | 0.049 |

TABLE 16-continued

| Particle size range (μm) | $d_p$ (mm) | $k_c$ (m/s) | δ (mm) |
|---|---|---|---|
| T = 300° C. | | | |
| 707-841 | 0.774 | $3.65 * 10^{-4}$ | 0.144 |
| 420-500 | 0.460 | $5.25 * 10^{-4}$ | 0.100 |
| 210-297 | 0.254 | $8.13 * 10^{-4}$ | 0.065 |
| 147-210 | 0.179 | $1.06 * 10^{-4}$ | 0.049 |
| T = 325° C. | | | |
| 707-841 | 0.774 | $3.69 * 10^{-4}$ | 0.146 |
| 420-500 | 0.460 | $5.32 * 10^{-4}$ | 0.101 |
| 210-297 | 0.254 | $8.24 * 10^{-4}$ | 0.065 |
| 147-210 | 0.179 | $1.08 * 10^{-4}$ | 0.050 |
| T = 350° C. | | | |
| 707-841 | 0.774 | $3.72 * 10^{-4}$ | 0.147 |
| 420-500 | 0.460 | $5.37 * 10^{-4}$ | 0.102 |
| 210-297 | 0.254 | $8.34 * 10^{-4}$ | 0.066 |
| 147-210 | 0.179 | $1.09 * 10^{-4}$ | 0.050 |

(wt. of the cat. = 2 g, P = 9.1 MPa, Flow rate = 120 ml/min, $H_2$/CO molar ratio = 1.25)

TABLE 17

| Flow rate (ml/min) | $k_c$ (m/s) | δ (mm) |
|---|---|---|
| 80 | $9.94 * 10^{-4}$ | 0.054 |
| 100 | $1.04 * 10^{-3}$ | 0.052 |
| 120 | $1.08 * 10^{-3}$ | 0.050 |
| 140 | $1.12 * 10^{-3}$ | 0.048 |
| 80 | $9.94 * 10^{-4}$ | 0.054 |
| 100 | $1.04 * 10^{-3}$ | 0.052 |
| 120 | $1.08 * 10^{-3}$ | 0.050 |
| 140 | $1.12 * 10^{-3}$ | 0.048 |

(wt. of the cat. = 2 g, T = 325° C., P = 9.1 MPa (1320 psig), $H_2$/CO molar ratio = 1.25, average particle size = 0.179 mm)

TABLE 18

| Parameter | Value |
|---|---|
| $k_{CH_3OH}^0$ | $1.502 * 10^{-4}$ |
| $k_{C_2H_5OH}^0$ | $3.511 * 10^{-2}$ |
| $k_{HA}^0$ | $1.837 * 10^3$ |
| $k_{HC}^0$ | $3.270 * 10^4$ |
| $k_{CO_2}$ | $2.928 * 10^2$ |
| $E_{CH_3OH}$ | 35 |
| $E_{C_2H_5OH}$ | 57 |
| $E_{HA}$ | 94 |
| $E_{HC}$ | 112 |
| $E_{CO_2}$ | 103 |
| a | 0.871 |
| b | 1.898 |
| c | 0.765 |
| d | 1.237 |
| e | 0.356 |
| f | 1.023 |
| g | 0.124 |
| h | 1.132 |
| i | 1.118 |
| j | 0.012 |
| k | 1.232 |
| l | 0.234 |

$k_i^0$ units depend on the kinetic expression obtained for the corresponding $r_i$ which is expressed as mole/(kg of cat.)/h; units of E, are in kJ/mole.

TABLE 19

| Reference | A | B | C | D |
|---|---|---|---|---|
| Catalyst | Sulfided Co—Mo—K/C* | Co—Mo—K/C | Cs/$MoS_2$ | Co—Rh—Mo—K/MWCNTs |
| Conditions | P = 100 bar, $H_2$/CO = 1.01 | P = 40-70 bar, $H_2$/CO = 0.5-2.0 | P = 82.7 bar, $H_2$/CO = 0.96 | P = 55.2-96.5 bar, $H_2$/CO = 0.5-2.0 |
| Methanol | 49 | 117.7**** | 68 | 35 |
| Ethanol | 76 | 38.3 | 94.9 | 57 |
| Higher alcohols | 109** | 97.9** | 98.5** | 94 |
| Hydrocarbons | 118*** | 106.5 | — | 112 |

TABLE 20

| Catalyst | Targeted composition (wt %) | | | | Measured composition (wt %) | | | BET surface area ($m^2$/g) | Total pore volume (cc/g) | Average pore diameter (nm) | CO uptake (μmole/g of cat.) | Dispersion of metals (%) |
|---|---|---|---|---|---|---|---|---|---|---|---|---|
| | K | Mo | Rh | Co | Mo | Rh | Co | | | | | |
| Fresh catalyst supported on MWCNT | 9 | 15 | 1.5 | 4.5 | 14.3 | 1.2 | 4.2 | 68 | 0.24 | 17.9 | — | — |
| Sulfided catalyst supported on MWCNT | 9 | 15 | 1.5 | 4.5 | — | — | — | 79 | 0.29 | 16.7 | 237 | 47.8 |
| Spent catalyst supported on MWCNT | 9 | 15 | 1.5 | 4.5 | 14.1 | 1.3 | 4.0 | 71 | 0.26 | 17.4 | 221 | 44.7 |
| Fresh catalyst supported on AC | 9 | 15 | 1.5 | 4.5 | 13.7 | 0.8 | 3.8 | 97 | 0.16 | 7.2 | — | — |
| Sulfided catalyst supported on AC | 9 | 15 | 1.5 | 4.5 | — | — | — | 111 | 0.21 | 6.4 | 137 | 27.7 |
| Spent catalyst supported on AC | 9 | 15 | 1.5 | 4.5 | 13.8 | 0.6 | 3.4 | 85 | 0.10 | 8.1 | 78 | 15.8 |

TABLE 21

| Crystal phase | 2θ | d-spacing | Reflection plane h k l |
|---|---|---|---|
| Graphite (C) | 26.6° | 3.347 | 1 1 1 |
| $MoO_3$ | 40.7° | 2.271 | 1 5 0 |
| $KMo_4O_6$ | 15.8° | 5.336 | 1 1 0 |
| $K_2Mo_7O_{20}$ | 23.6° | 3.770 | 1 0 2 |
| $K_2Mo_2O_7$ | 28.5° | 3.222 | 0 0 2 |
| $KMo_4O_6$ | 37.1° | 2.403 | 4 0 0 |
| $MoS_2$ | 14.6° | 6.110 | 0 0 3 |
| $MoS_2$ | 33.4° | 2.707 | 1 0 1 |
| $MoS_2$ | 40.9° | 2.199 | 0 1 5 |
| $MoS_2$ | 58.9° | 1.570 | 1 1 0 |
| $MoS_2$ | 60.0° | 1.541 | 0 0 3 |
| $K_{0.4}MoS_2$ | 21.5° | 4.130 | 0 0 4 |
| $KMo_3S_3$ | 28.7° | 3.100 | 1 1 1 |
| $K_2MoS_4$ | 29.9° | 3.020 | 3 0 1 |
| $K_2MoS_4$ | 31.1° | 2.780 | 3 0 2 |
| $Co_9S_8$ | 47.9° | 1.911 | 5 1 1 |
| $Co_9S_8$ | 52.4 | 1.751 | 4 4 0 |

The invention claimed is:

1. A process for producing higher alcohols from synthesis gas, the process comprising reacting the gas with a catalyst under conditions for the formation of higher alcohols, wherein the catalyst comprises the metals A, $M^1$, $M^2$ and $M^3$,
wherein A is an alkali metal;
$M^1$ is selected from Co, Ni and Fe;
$M^2$ is selected from Rh, Ru and Pd; and
$M^3$ is selected from Mo;
and the catalyst is supported on a support material comprising multiwalled carbon nanotubes (MWCNTs).

2. The process of claim 1, wherein the conditions for the formation of higher alcohols comprise a temperature of about 300° C. to about 350° C. a pressure of about 5.5 Mpa to about 10 MPa and a gas hourly space velocity (GHSV) of about 2.5 $m^3$ (STP)/(kg of cat)/h to about to about 4.5 $m^3$ (STP)/(kg of cat)/h.

3. The process of claim 2, wherein the synthesis gas comprises $H_2$ and CO in a molar ratio of $H_2$:C of about 1:1 to about 1.5:1.

4. The process of claim 1, wherein the catalyst is activated and sulfided in a single step prior to use to convert synthesis gas to higher alcohols.

5. The process of claim 4, wherein the catalyst is activated and sulfided by treatment with an $H_2S/H_2$ gas mixture, at a temperature of about 300° C. to about 550° C., at a heating rate of about 1-5° C./min, for about 2 to about 10 hours.

6. The process of claim 1, wherein the conditions for the formation of higher alcohols comprise a temperature of about 330° C., a pressure of about 8.0 MPa to about 9.0 MPa, and a gas hourly space velocity (GHSV) of about 3.8 $m^3$ (STP)/(kg of cat)/h.

7. The process of claim 3, wherein the synthesis gas comprises $H_2$ and CO in a molar ratio of $H_2$:CO of about 1.25:1.

8. The process of claim 5, wherein the catalyst is activated and sulfided by treatment with an $H_2S/H_2$ gas mixture comprising about 5 mole % to about 20 mole % $H_2S$ in $H_2$ gas, at a temperature of about 450° C., at a heating rate of about 2° C./min, for about 4 hours.

9. The process of claim 1, wherein the catalyst comprises the metals A, Co, Rh and Mo, wherein A is an alkali metal, and the catalyst is supported on multi-walled carbon nanotubes (MWCNTs).

10. The process of claim 1, wherein the alkali metal is K and is present in an amount of about 8 wt % to about 10 wt %.

11. The process of claim 1, wherein the alkali metal is K and is present in an amount of about 9 wt %.

12. The process of claim 1, wherein the catalyst comprises about 3.5 wt % to about 7 wt % Co; about 0.5 wt % to about 2.5 wt % Rh; and about 14 wt % to about 16 wt % Mo.

13. The process of claim 1, wherein the catalyst comprises about 9 wt % K, about 4.5 wt % Co, about 1.5 wt % Rh and about 15 wt % Mo, the remainder being primarily the carbon-based support.

14. The process of claim 1, wherein the catalyst is prepared by impregnation using an incipient wetness impregnation method.

15. The process claim 1, wherein the catalyst has an average particle size of about 140 μm to about 220 μm.

* * * * *

UNITED STATES PATENT AND TRADEMARK OFFICE
CERTIFICATE OF CORRECTION

PATENT NO. : 9,108,183 B2  
APPLICATION NO. : 13/457893  
DATED : August 18, 2015  
INVENTOR(S) : Ajay Kumar Dalai et al.

Page 1 of 1

It is certified that error appears in the above-identified patent and that said Letters Patent is hereby corrected as shown below:

In the claims  
Column 57, line 39, "$H_2$:C" should read --"$H_2$:CO"--.

Signed and Sealed this  
Twenty-ninth Day of March, 2016

Michelle K. Lee  
*Director of the United States Patent and Trademark Office*